(12) United States Patent
Solaja et al.

(10) Patent No.: US 6,906,098 B2
(45) Date of Patent: Jun. 14, 2005

(54) MIXED STEROIDAL 1,2,4,5-TETRAOXANE COMPOUNDS AND METHODS OF MAKING AND USING THEREOF

(75) Inventors: Bogdan Solaja, Belgrade (YU); Dejan M. Opsenica, Veljka (YU); Gabriella Pocsfalvi, Napoli (IT); Wilbur K. Milhous, Germantown, MD (US); Dennis E. Kyle, Fig Tree Pocket (AU)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/359,584

(22) Filed: Feb. 7, 2003

(65) Prior Publication Data

US 2004/0019200 A1 Jan. 29, 2004

Related U.S. Application Data

(60) Provisional application No. 60/356,633, filed on Feb. 9, 2002.

(51) Int. Cl.[7] ................... A61K 31/357; C07D 323/04
(52) U.S. Cl. .................. 514/452; 549/336; 546/195; 546/197; 548/526; 514/319; 514/321; 514/422
(58) Field of Search ................ 514/452, 319, 514/321, 422; 549/336; 546/195, 197; 548/526

(56) References Cited

U.S. PATENT DOCUMENTS

| | | |
|---|---|---|
| 3,003,000 A | 10/1961 | Milas |
| 3,116,300 A | 12/1963 | Braunwarth et al. |
| 3,879,420 A | 4/1975 | Story et al. |
| 3,880,882 A | 4/1975 | Story et al. |
| 3,925,417 A | 12/1975 | Story et al. |
| 3,925,421 A | 12/1975 | Story et al. |
| 3,960,897 A | 6/1976 | Story et al. |
| 5,578,637 A | 11/1996 | Lai et al. |
| 6,054,625 A | 4/2000 | Frenkel et al. |

FOREIGN PATENT DOCUMENTS

| | | |
|---|---|---|
| FR | 1175415 | 3/1959 |
| GB | 842922 | 7/1960 |
| JP | 2000-229965 | 8/2000 |
| JP | 2003104967 | 4/2003 |
| WO | WO 93/07119 | 4/1993 |

OTHER PUBLICATIONS

Solaja, B. et al.: Mixed steroidal 1, 2,4,5–tetraoxanes: Antimalarial and antibacterial activity. J. Med. Chem. vol. 45, pp. 3331–3336, 2002.*

Bertrand, et al., "Mass Spectrometry of Cyclic Organic Peroxides", Cyclic Organic Peroxides, vol. 33, No. 5, pp. 1931–1934, (1968).

Caglioti, et al., "Oxidation of N–Alkyl–N'–Tosylhydrazines to Hydroperoxides", Tetrahedron, vol. 34, pp. 135–139 (1978).

(Continued)

Primary Examiner—Charanjit S. Aulakh
(74) Attorney, Agent, or Firm—Elizabeth Arwine

(57) ABSTRACT

Disclosed herein are mixed steroidal tetraoxanes having the following structural formula 1

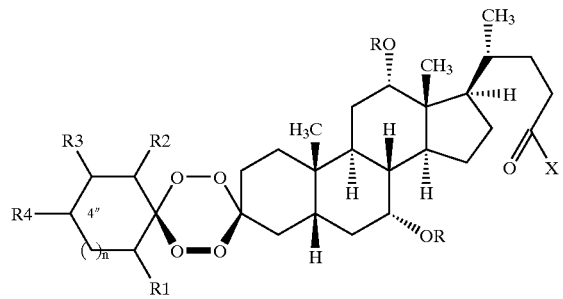

wherein n is 0, 1, 2, or 3; R is H; ethanoyl, propanoyl, or benzoyl; R1 is H, methyl, ethyl, or isopropyl; R2 is H, methyl, or ethyl; R3 is H, methyl, or ethyl; R4 is H, methyl, ethyl, tert-butyl, phenyl, p-hydroxyphenyl, p-methoxyphenyl, or p-nitrophenyl, or

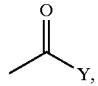

wherein Y is a $C_1$–$C_4$ straight or branched-chain alkoxy, or

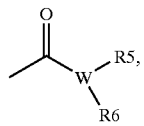

wherein W is N, R5 is hydrogen, methyl, ethyl, n-propyl, isopropyl, or methyl ethanoate 2-yl, and R6 is hydrogen, methyl, ethyl, or n-propyl, or R5 and R6 are part of a pyrrolidine or piperidine ring; X is a $C_1$–$C_4$ straight or branched-chain alkoxy, a primary amino, a N-alkylamino wherein the alkyl is a straight-chain alkyl groups containing from 1 to 4 carbon atoms, methyl ethanoate-2-yl, N-phenylamino, p-nitrophenyl, N,N-dimethylamino, N,N-diethylamino, N,N-di(n-propyl)amino, N-pyrrolidino, or N-piperidino as single compounds, and any mixture of all possible stereoisomers at C(4"). n may be 0, 1, 2, or 3, and methods of making and using thereof. As disclosed herein, the mixed steroidal tetraoxanes of the present invention exhibit antimalarial, antibacterial, and antiproliferative activity. Thus, as disclosed herein, the mixed steroidal tetraoxanes of the present invention may be used to treat, prevent, or inhibit malaria, bacterial infections, and diseases and disorders associated with cell proliferation in a subject.

57 Claims, 8 Drawing Sheets

OTHER PUBLICATIONS

Cremer, et al., "A General Definition of Ring Puckering Corrdinates", Journal of the American Chemical Society, 97:6, pp. 1354–1358 (1975).

Dong, et al., "Synthesis and Antimalarial Activity of 11 Dispiro–1,2,4,5–tetraoxane Analogues of WR 148999. 7,8, 15,16–Tetraoxadispiro [5.2.5.2] hexadecanes Substituted at the 1 and 10 Positions with Unsaturated and Polar Functional Groups", J. Med. Chem. (1999), 42, pp. 1477–1480.

Jefford, et al., "A New Method for the Synthesis of gem–Dihydroperoxides", Synthetic Communications, 20(17), pp. 2589–2596 (1990).

Jefford, et al., "Efficient Preparation of 1, 2, 3, 5–Tetroxanes from Bis(trimethylsilyl) Peroxide and Carbonyl Compounds", Communications, pp. 391–393 (1988).

Jefford, et al, "The Structure and Antimalarial Activity of Some 1,2,4–Trioxanes, 1,2,4,5–Tetroxanes, and Bicyclic Endoperoxides. Implications for the Mode of Action", Heterocycles, vol. 52, No. 3, pp. 1345–1352 (2000).

Kharasch, et al., "Structure of Peroxides Derived from Cyclohexanone and Hydrogen Peroxide", Institute of Organic Chemistry, the University of Chicago, vol. 23, pp. 1322–1326 (1958).

Kim, et al, Synthesis and Antimalarial Activity of Novel Medium–Sized 1,2,4,5–Tetraoxacycloalkanes, J. Med. Chem. (2001), 33, pp. 2357–2361.

Kim, et al, Synthetic methods for unsymmetrically–substituted 1,2,4,5–tetraoxanes and of 1,2,4,5,7–pentoxocanes, J. Chem. Soc., Perkin Trans 1, (1999), pp. 1867–1870.

Ledal, "Mass Spectrometric Investigations of Organic Peroxides", Tetrahedron Letters No. 41, pp. 3661–3664 (1969).

McCullough, et al., "Ketone–derived Peroxides, Part 1, Synthetic Methods", J. Chem. Research (S), 1980, 34.

McCullough, et al., "Methyl–Substituted Dispiro–1,2,4, 5–tetraoxanes: Corelations of Structural Studies with Antimalarial Activity", J. Med. Chem, 2000, 43, pp. 1246–1249.

McCullough, et al., "The synthesis and crystal structure analysis of novel macrocyclic peroxides", Tetrahedron Letters 42 (2001) pp. 5529–5532.

Milas, et al., "Studies in Organic Peroxides. XXIV. Preparation, Separation and Identification of Peroxides Derived from Diethyl Ketone and Hydrogen Peroxide", The Department of Chemistry, Massachusetts Institute of Technology, pp. 3361–3363 (1959).

Milas, et al., "Studies in Organic Peroxides. XXV. Preparation, Separation and Identification of Peroxides Derived from Methyl Ethyl Ketone and Hydrogen Peroxide", The Department of Chemistry, Massachusetts Institute of Technology, pp. 5824–5826, vol. 81 (1959).

Milas, et al., "Studies in Organic Peroxides. XXVI. Organic Peroxides Derived from Acetone and Hydrogen Peroxide", The Department of Chemistry, Massachusetts Institute of Technology, pp. 6461–6462, vol. 81 (1959).

Nonami, et al., "Synthesis, crystal structure and antimalarial activity of functionalized spiro–1,2,4,5–tetraoxacycloalkanes from unsaturated hydroperoxy peracetals", Tetrahedron Letters 41 (2000) pp. 4681–4684.

Opsenica, et al., "Cholic Acid Derivatives as 1,2,4,5–Tetraoxane Carriers: Structure and Antimalarial and Antiproliferative Activity", J. Med. Chem. (2000), 43, pp. 3274–3282.

Robertson, et al., "Diphenylmethyl Bishydroperoxide. An Anomalous Product from the Ozonolysis of Tetraphenylethylene" The Journal of Organic Chemistry, vol. 35, No. 2, pp. 545–547 (1970).

Sanderson, et al., "Macrocycles. The Synthesis and Thermal Decomposition of Some Disubstituted Dicyclohexylidene Diperoxides", Communications, pp. 159–161 (1975).

Todorovic, et al., "Steriodal geminal dehydroperoxides and 1,2,4,5–tetraoxanes: Structure determination and their antimalarial activity", Steroids, (1996), vol. 61, pp. 688–696.

Tsuchiya, et al., "Synthesis, Crystal Structure and Anti–Malarial Activity of Novel Spiro–1,2,4,5–Tetraoxacycloalkanes", Tetrahedron Letters 40 (1999) pp. 4077–4080.

Velluz, et al., Bishydroperoxydes steroids. II—Preparation et proprietes, Memoires Presentes A La Societe Chimique, pp. 879–882, (1957).

Vennerstrom, et al., "Synthesis and Antimalarial Activity of Sixteen Dispiro–1,2,4,5–tetraoxanes: Alkyl–Substituted 7,8, 15,16–Tetraoxadispiro [5.2.5.2] hexadecanes", J. Med. Chem. (2000), 43, pp. 2753–2758.

Vennerstrom, et al., "Dispiro–1,2,4,5–tetraoxanes: A New Class of Antimalarial Peroxides", J. Med. Chem. (1992), 35, pp. 3023–3027.

Warnant, et al., "No. 39—Bis–hydroperoxydes de quelques ceto–steroides", Memoires Presentes A La Societe Chimique, pp. 331–332, (1956).

2000 American Chemical Society, J. Med. Chem., Opsenica jm000952f Supporting Info, pp. 1–13.

International Search Report (Form PCT/ISA/210) issued for PCT/US03/03516 (Feb. 13, 2004).

* cited by examiner

|  | Time |  | Mean Optical Densities |  |  |  |  | Percent Growth |  |  |  |  |  |  |
|---|---|---|---|---|---|---|---|---|---|---|---|---|---|---|---|
|  |  |  |  |  | Log10 Concentration |  |  |  |  |  |  |  |  |  |  |
| Panel/Cell Line | Zero | Ctrl | -8.0 | -7.0 | -6.0 | -5.0 | -4.0 | -8.0 | -7.0 | -6.0 | -5.0 | -4.0 | GI50 | TGI | LC50 |
| Leukemia |  |  |  |  |  |  |  |  |  |  |  |  |  |  |  |
| CCRF-CEM | 0.183 | 0.960 | 0.968 | 0.933 | 0.853 | 0.319 | 0.204 | 101 | 97 | 86 | 18 | 3 | 3.37E-06 | >1.00E-04 | >1.00E-04 |
| HL-60(TB) | 0.482 | 2.159 | 1.838 | 1.776 | 1.720 | 0.293 | 0.325 | 81 | 77 | 74 | -39 | -33 | 1.62E-06 | 4.50E-06 | >1.00E-04 |
| K-562 | 0.102 | 0.756 | 0.799 | 0.746 | 0.770 | 0.293 | 0.162 | 107 | 99 | 102 | 29 | 9 | 5.18E-06 | >1.00E-04 | >1.00E-04 |
| MOLT-4 | 0.135 | 0.647 | 0.631 | 0.610 | 0.522 | 0.195 | 0.182 | 97 | 93 | 76 | 12 | 9 | 2.52E-06 | >1.00E-04 | >1.00E-04 |
| SR | 0.215 | 0.816 | 0.840 | 0.803 | 0.671 | 0.167 | 0.197 | 104 | 98 | 76 | -22 | -9 | 1.83E-06 | 5.92E-06 | >1.00E-04 |
| Non-Small Cell Lung Cancer |  |  |  |  |  |  |  |  |  |  |  |  |  |  |  |
| A549/ATCC | 0.519 | 2.225 | 2.204 | 2.205 | 1.945 | 0.863 | 0.416 | 99 | 99 | 84 | 20 | -20 | 3.39E-06 | 3.19E-05 | >1.00E-04 |
| EKVX | 0.775 | 1.648 | 1.666 | 1.432 | 1.542 | 0.751 | 0.490 | 102 | 75 | 88 | -3 | -37 | 2.61E-06 | 9.25E-06 | >1.00E-04 |
| HOP-62 | 0.293 | 0.981 | 0.994 | 0.972 | 0.936 | 0.467 | 0.394 | 102 | 99 | 93 | 25 | 15 | 4.34E-06 | >1.00E-04 | >1.00E-04 |
| HOP-92 | 0.223 | 0.551 | 0.625 | 0.568 | 0.544 | 0.289 | 0.215 | 122 | 105 | 98 | 20 | -4 | 4.11E-06 | 7.04E-05 | >1.00E-04 |
| NCI-H226 | 0.909 | 1.600 | 1.663 | 1.722 | 1.688 | 1.393 | 0.748 | 109 | 118 | 113 | 70 | -18 | 1.69E-05 | 6.28E-05 | >1.00E-04 |
| NCI-H23 | 0.463 | 0.926 | 0.911 | 0.925 | 0.905 | 0.379 | 0.250 | 97 | 100 | 95 | -18 | -46 | 2.51E-06 | 6.91E-06 | >1.00E-04 |
| NCI-H322M | 0.679 | 0.974 | 0.989 | 0.957 | 0.913 | 0.609 | 0.112 | 105 | 94 | 79 | -10 | -84 | 2.12E-06 | 7.67E-06 | 3.48E-05 |
| NCI-H460 | 0.206 | 1.414 | 1.369 | 1.358 | 1.283 | 0.320 | 0.179 | 96 | 95 | 89 | 9 | -13 | 3.10E-06 | 2.62E-05 | >1.00E-04 |
| NCI-H522 | 0.608 | 1.424 | 1.419 | 1.329 | 1.312 | 0.431 | 0.157 | 99 | 88 | 86 | -29 | -74 | 2.06E-06 | 5.59E-06 | 2.90E-05 |
| Colon Cancer |  |  |  |  |  |  |  |  |  |  |  |  |  |  |  |
| COLO 205 | 0.390 | 2.616 | 2.655 | 2.683 | 2.470 | 1.138 | 0.475 | 102 | 103 | 93 | 34 | 4 | 5.32E-06 | >1.00E-04 | >1.00E-04 |
| HCT-116 | 0.229 | 1.453 | 1.392 | 1.371 | 1.365 | 0.644 | 0.256 | 95 | 93 | 93 | 34 | 2 | 5.33E-06 | >1.00E-04 | >1.00E-04 |
| HCT-15 | 0.220 | 1.333 | 1.360 | 1.321 | 1.220 | 0.502 | 0.149 | 102 | 99 | 90 | 25 | -32 | 4.14E-06 | 2.75E-05 | >1.00E-04 |
| HT29 | 0.327 | 1.513 | 1.289 | 1.347 | 1.351 | 0.555 | 0.178 | 81 | 86 | 86 | 19 | -46 | 3.48E-06 | 1.98E-05 | >1.00E-04 |
| KM12 | 0.384 | 1.111 | 1.069 | 1.053 | 0.992 | 0.265 | 0.144 | 94 | 92 | 84 | -31 | -63 | 1.96E-06 | 5.36E-06 | 4.01E-05 |
| SW-620 | 0.231 | 1.109 | 1.119 | 0.991 | 0.981 | 0.418 | 0.194 | 101 | 87 | 85 | 21 | -16 | 3.56E-06 | 3.72E-05 | >1.00E-04 |

Figure 2

| Panel/Cell Line | Time Zero | Ctrl | Mean Optical Densities | | | | | Percent Growth | | | | | GI50 | TGI | LC50 |
|---|---|---|---|---|---|---|---|---|---|---|---|---|---|---|---|
| | | | -8.0 | -7.0 | -6.0 | -5.0 | -4.0 | -8.0 | -7.0 | -6.0 | -5.0 | -4.0 | | | |
| CNS Cancer | | | | | | | | | | | | | | | |
| SF-268 | 0.472 | 1.468 | 1.438 | 1.428 | 1.349 | 0.728 | 0.317 | 97 | 96 | 88 | 26 | -33 | 4.08E-06 | 2.74E-05 | >1.00E-04 |
| SF-295 | 0.423 | 1.490 | 1.413 | 1.459 | 1.408 | 0.644 | 0.337 | 93 | 97 | 92 | 21 | -20 | 3.89E-06 | 3.19E-05 | >1.00E-04 |
| SF-539 | 0.640 | 1.664 | 1.661 | 1.712 | 1.632 | 0.563 | 0.238 | 100 | 105 | 97 | -12 | -63 | 2.69E-06 | 7.75E-06 | 5.58E-05 |
| SNB-19 | 0.634 | 1.883 | 1.835 | 1.889 | 1.759 | 1.228 | 0.600 | 96 | 100 | 90 | 48 | -5 | 8.74E-06 | 7.89E-05 | >1.00E-04 |
| SNB-75 | 0.632 | 1.398 | 1.506 | 1.474 | 1.468 | 0.954 | 0.498 | 114 | 110 | 109 | 42 | -21 | 7.61E-06 | 4.62E-05 | >1.00E-04 |
| U251 | 0.317 | 1.634 | 1.641 | 1.644 | 1.544 | 0.459 | 0.233 | 101 | 101 | 93 | 11 | -26 | 3.34E-06 | 1.94E-05 | >1.00E-04 |
| Melanoma | | | | | | | | | | | | | | | |
| LOX IMVI | 0.523 | 2.488 | 2.433 | 2.434 | 2.319 | 0.514 | 0.378 | 97 | 97 | 91 | -2 | -28 | 2.78E-06 | 9.58E-06 | >1.00E-04 |
| MALME-3M | 0.618 | 1.011 | 0.984 | 0.901 | 0.930 | 0.598 | 0.168 | 93 | 72 | 79 | -3 | -73 | 2.27E-06 | 9.14E-06 | 4.70E-05 |
| M14 | 0.385 | 1.089 | 1.101 | 1.067 | 1.086 | 0.727 | 0.309 | 102 | 97 | 100 | 49 | -20 | 9.37E-06 | 5.12E-05 | >1.00E-04 |
| SK-MEL-2 | 0.787 | 1.466 | 1.419 | 1.462 | 1.531 | 0.694 | 0.241 | 93 | 99 | 109 | -12 | -69 | 3.09E-06 | 7.98E-06 | 4.59E-05 |
| SK-MEL-28 | 0.834 | 2.030 | 2.047 | 2.140 | 1.860 | 1.393 | 0.353 | 101 | 109 | 86 | 47 | -58 | 8.26E-06 | 2.80E-05 | 8.44E-05 |
| SK-MEL-5 | 0.473 | 1.732 | 1.684 | 1.567 | 1.457 | 0.654 | 0.151 | 96 | 87 | 78 | 14 | -68 | 2.76E-06 | 1.49E-05 | 6.03E-05 |
| UACC-257 | 0.434 | 0.946 | 0.977 | 0.933 | 0.932 | 0.601 | 0.191 | 106 | 97 | 97 | 33 | -56 | 5.38E-06 | 2.33E-05 | 8.56E-05 |
| UACC-62 | 0.986 | 2.395 | 2.426 | 2.573 | 2.628 | 1.342 | 0.329 | 102 | 113 | 117 | 25 | -67 | 5.36E-06 | 1.88E-05 | 6.59E-05 |
| Ovarian Cancer | | | | | | | | | | | | | | | |
| IGROV1 | 0.263 | 0.942 | 0.883 | 0.886 | 0.240 | 0.052 | 0.102 | 91 | 92 | -9 | -80 | -61 | 2.60E-07 | 8.18E-07 | 3.76E-06 |
| OVCAR-3 | 0.390 | 1.121 | 1.038 | 0.997 | 0.976 | 0.522 | 0.181 | 89 | 83 | 80 | 18 | -54 | 3.06E-06 | 1.79E-05 | 8.91E-05 |
| OVCAR-4 | 0.916 | 2.149 | 2.250 | 2.158 | 2.013 | 1.309 | 0.489 | 108 | 101 | 89 | 32 | -47 | 4.81E-06 | 2.55E-05 | >1.00E-04 |
| OVCAR-5 | 0.157 | 0.589 | 0.591 | 0.590 | 0.579 | 0.242 | 0.146 | 101 | 100 | 98 | 20 | -7 | 4.09E-06 | 5.47E-05 | >1.00E-04 |
| SK-OV-3 | 0.769 | 1.448 | 1.449 | 1.402 | 1.366 | 1.152 | 0.292 | 100 | 93 | 88 | 56 | -62 | 1.13E-05 | 2.99E-05 | 7.91E-05 |

Figure 2 cont.

| | | Mean Optical Densities | | | | | Percent Growth | | | | | | |
|---|---|---|---|---|---|---|---|---|---|---|---|---|---|
| | Time | | | Log10 Concentration | | | | | | | | | |
| Panel/Cell Line | Zero | Ctrl | -8.0 | -7.0 | -6.0 | -5.0 | -4.0 | -8.0 | -7.0 | -6.0 | -5.0 | -4.0 | GI50 | TGI | LC50 |
| Renal Cancer | | | | | | | | | | | | | | | |
| 786-0 | 0.213 | 1.025 | 1.050 | 0.954 | 1.013 | 0.507 | 0.311 | 103 | 91 | 99 | 36 | 12 | 6.01E-06 | >1.00E-04 | >1.00E-04 |
| A498 | 1.081 | 1.759 | 1.735 | 1.752 | 1.708 | 1.455 | 0.443 | 96 | 99 | 92 | 55 | -59 | 1.11E-05 | 3.04E-05 | 8.34E-05 |
| ACHN | 0.384 | 1.692 | 1.670 | 1.717 | 1.664 | 0.666 | 0.075 | 98 | 102 | 98 | 22 | -81 | 4.23E-06 | 1.62E-05 | 5.02E-05 |
| CAKI-1 | 0.658 | 1.571 | 1.502 | 1.559 | 1.466 | 0.917 | 0.217 | 92 | 99 | 88 | 28 | -67 | 4.36E-06 | 1.98E-05 | 6.62E-05 |
| RXF 393 | 0.626 | 1.040 | 1.035 | 1.029 | 0.991 | 0.689 | 0.235 | 99 | 97 | 88 | 15 | -62 | 3.33E-06 | 1.57E-05 | 6.91E-05 |
| SN12C | 0.417 | 1.372 | 1.439 | 1.467 | 1.431 | 0.739 | 0.210 | 107 | 110 | 106 | 34 | -50 | 5.97E-06 | 2.54E-05 | >1.00E-04 |
| TK-10 | 0.723 | 0.945 | 0.951 | 0.928 | 0.904 | 0.551 | 0.111 | 103 | 92 | 81 | -24 | -85 | 1.99E-06 | 5.94E-06 | 2.70E-05 |
| UO-31 | 0.395 | 1.520 | 1.505 | 1.458 | 1.477 | 0.078 | 0.095 | 99 | 95 | 96 | -80 | -76 | 1.83E-06 | 3.51E-06 | 6.73E-06 |
| Prostate Cancer | | | | | | | | | | | | | | | |
| DU-145 | 0.261 | 1.064 | 1.017 | 1.003 | 0.945 | 0.492 | 0.146 | 94 | 92 | 85 | 29 | -44 | 4.20E-06 | 2.48E-05 | >1.00E-04 |
| Breast Cancer | | | | | | | | | | | | | | | |
| MCF7 | 0.211 | 1.044 | 1.001 | 1.062 | 1.004 | 0.371 | 0.180 | 95 | 102 | 95 | 19 | -15 | 3.93E-06 | 3.68E-05 | >1.00E-04 |
| NCI/ADR-RES | 0.374 | 0.975 | 0.967 | 0.974 | 0.900 | 0.413 | 0.229 | 99 | 100 | 88 | 6 | -39 | 2.90E-06 | 1.39E-05 | >1.00E-04 |
| MDA-MB-231/ATCC | 0.437 | 1.068 | 1.142 | 1.130 | 1.167 | 0.839 | 0.404 | 112 | 110 | 116 | 64 | -8 | 1.56E-05 | 7.83E-05 | >1.00E-04 |
| HS 578T | 0.597 | 1.431 | 1.471 | 1.443 | 1.292 | 0.858 | 0.624 | 105 | 101 | 83 | 31 | 3 | 4.36E-06 | >1.00E-04 | >1.00E-04 |
| MDA-MB-435 | 0.599 | 1.964 | 1.908 | 1.902 | 1.748 | 0.799 | 0.272 | 96 | 95 | 84 | 15 | -55 | 3.10E-06 | 1.63E-05 | 8.58E-05 |
| BT-549 | 0.602 | 1.563 | 1.530 | 1.529 | 1.491 | 0.827 | 0.451 | 97 | 97 | 93 | 23 | -25 | 4.12E-06 | 3.04E-05 | >1.00E-04 |
| T-47D | 0.310 | 1.221 | 1.125 | 1.145 | 1.037 | 0.722 | 0.493 | 89 | 92 | 80 | 45 | 20 | 7.26E-06 | >1.00E-04 | >1.00E-04 |

MIXED STEROIDAL 1,2,4,5-TETRAOXANE COMPOUNDS AND METHODS OF MAKING AND USING THEREOF

CROSS REFERENCE TO RELATED APPLICATIONS

This application claims the benefit of U.S. Provisional Patent Application No. 60/356,633 filed 9 Feb. 2002, which names Bogdan A. Solaja, Gabriella Pocsfalvi, Dennis E. Kyle, Dejan Opsenica, and Wilbur K. Milhous as joint inventors and is herein incorporated by reference in its entirety.

ACKNOWLEDGMENT OF GOVERNMENT SUPPORT

This invention was made by employees of the United States Army. The government has rights in the invention.

BACKGROUND OF THE INVENTION

1. Field of the Invention

The present invention relates to steroidal mixed tetraoxanes and to processes for the production thereof. In a preferred embodiment, the present invention relates to cycloalkyl-spiro-1,2,4,5-tetraoxacyclohexane-spiro-cholic acids and derivatives thereof, which are active against chloroquine-resistant malaria. The present invention also relates to gem-dihydroperoxides of cholic acids and derivatives thereof, and 1,1-dihydroperoxy(susbstituted) cycloalkanes.

2. Description of the Related Art

The current global situation with respect to malaria indicates that about two billion people are exposed to the disease and of these 400 million people are already infected. See Trigg, P. I., and A. V. Kondrachine (1998) The Current Global Malaria Situation, Chapter 2, p. 11–22, in MALARIA PARASITE BIOLOGY, PATHOGENESIS AND PROTECTION. Ed. I. W. Sherman, ASM Press, Washington, D.C. Each year between 100 to 200 million new cases of infection are reported and approximately 1 to 2 million people die due to malaria. The situation is rapidly worsening mainly due to non-availability of effective drugs and development of drug resistance of a large number of non-immune people in areas where malaria is frequently transmitted. See White, N. J. (1998) Br. Med. Bull. 54:703–715.

In an increasingly wide geographic area, both *Plasmodium falciparum* and *Plasmodium vivax* have been developing resistance to chloroquine, the most successful antimalarial drug in the past several decades. Mefloquine and doxycycline, the two other frontline drugs for the treatment and prevention of malaria are becoming increasingly ineffective. See Vroman, J. A. et al. (1999) Curr. Pharm. Design 5:101–138. Artemisinin analogs such as artesunate and arteether were later introduced that are found to be quite effective, particularly against drug-resistant *P. falciparum* but observations of drug-induced and dose-related neurotoxicity in animals have raised concern about the safety of these compounds for human use. See Bhattachajee, A. K. and J. M. Karle (1999) Chem. Res. Toxicol. 12: 422–428.

1,2,4,5-tetraoxane compounds have been found to exhibit antimalarial activity. See Vennerstrom, J. L., et al. (1992) J. Med. Chem. 35:3023–3027, WO93/07119, and Todorović, N. M., et al. (1996) Steroids 61:688–696. Unfortunately, the 1,2,4,5-tetraoxane compounds of the prior art are made by timely, complicated, and expensive methods, and also exhibit poor solubility under physiological conditions.

Therefore, a need still exists for a new class of tetraoxane compounds and compositions that may be used for treating, preventing, or inhibiting malaria and drug resistant malaria.

SUMMARY OF THE INVENTION

The present invention provides mixed steroidal tetraoxanes and methods of making and using thereof.

In some embodiments, the present invention provides a compound having the following structural formula 1

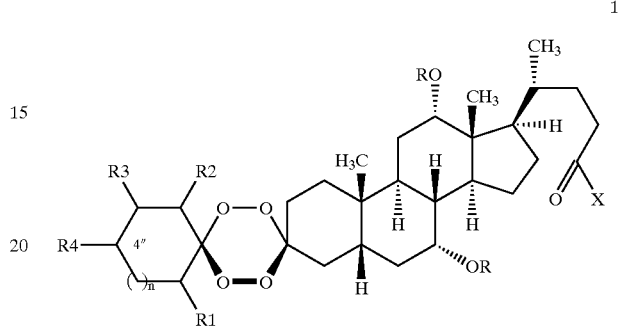

wherein
n is 0, 1, 2, or 3;
R is H; ethanoyl, propanoyl, or benzoyl;
R1 is H, methyl, ethyl, or isopropyl;
R2 is H, methyl, or ethyl;
R3 is H, methyl, or ethyl;
R4 is H, methyl, ethyl, tert-butyl, phenyl, p-hydroxyphenyl, p-methoxyphenyl, or p-nitrophenyl, or

wherein Y is a $C_1$–$C_4$ straight or branched-chain alkoxy, or

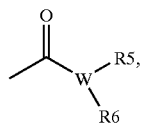

wherein W is N, R5 is hydrogen, methyl, ethyl, n-propyl, isopropyl, or methyl ethanoate 2-yl, and R6 is hydrogen, methyl, ethyl, or n-propyl, or R5 and R6 are part of a pyrrolidine or piperidine ring;
X is a $C_1$–$C_4$ straight or branched-chain alkoxy, a primary amino, a N-alkylamino wherein the alkyl is a straight-chain alkyl groups containing from 1 to 4 carbon atoms, methyl ethanoate-2-yl, N-phenylamino, p-nitrophenyl, N,N-dimethylamino, N,N-diethylamino, N,N-di(n-propyl)amino, N-pyrrolidino, or N-piperidino as single compounds, and any mixture of all possible stereoisomers at C(4"). n may be 0, 1, 2, or 3. In some preferred embodiments, R is ethanoyl. In some preferred embodiments, R1 is H, R2 is H, and R3 is H. In some embodiments, R4 is attached to ring carbon of (R)-configuration or (S)-configuration. In some embodiments, R4 is H, methyl, ethyl, phenyl, tert-butyl, n-propyl, orethoxycarbonyl. In some embodiments, X is hydroxy, methoxy, primary amino, N-methylamino, N-ethylamino, N-(n-propyl)amino, or N-(methyl ethanoate-2-yl)amino.

In some embodiments, the present invention provides a compound having the following structural formula 2

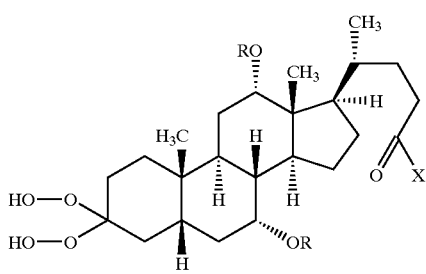

wherein
R is H, ethanoyl, propanoyl, or benzoyl;
X is a $C_1$–$C_4$ straight or branched-chain alkoxy, primary amino, N-alkylamino wherein the alkyl is a straight-chain alkyl group containing from 1 to 4 carbon atoms, methyl ethanoate-2-yl, N-phenylamino, p-nitrophenyl, N,N-dimethylamino, N,N-diethylamino, N,N-di(n-propyl)amino, N-pyrrolidino, or N-piperidino.

In some embodiments, the present invention provides a compound having the following structural formula 4

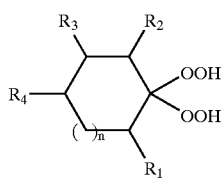

wherein
n is 0, 1, 2, or 3;
R1 is H;
R2 is H;
R3 is H;
R4 is H, a straight or branched-chain alkyl group containing from 1 to 3 carbon atoms, phenyl which may be substituted by one or more substituents selected from the group consisting of halogen, hydroxy, $C_1$–$C_2$ alkoxy, $C_1$–$C_2$ alkyl, nitro or $CF_3$; or

wherein Y is a $C_1$–$C_4$ straight or branched-chain alkoxy, or

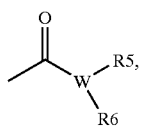

wherein W is N; R5 is hydrogen, a $C_1$–$C_4$ straight or branched-chain alkyl, a $C_1$–$C_4$ straight or branched-chain alkyl ethanoate 2-yl, ethanoic acid 2-yl, or phenyl which may be substituted by one or more substituents selected from the group consisting of halogen, $C_1$–$C_2$ alkoxy, $C_1$–$C_2$ alkyl or $CF_3$; and R6 is hydrogen, a $C_1$–$C_4$ straight or branched-chain alkyl, or R5 and R6 are part of a pyrrolidine or piperidine ring.

In some embodiments, the present invention provides mixture of two or more compounds of the present invention. In preferred embodiments, the mixtures comprise at least one pair of stereoisomers of one of the compounds in the mixture.

In some embodiments, the present invention provides a pharmaceutical composition comprising at least one compound of the present invention and a pharmaceutically acceptable carrier.

In some embodiments, the present invention provides a method of treating, preventing, or inhibiting a disease or disorder associated with a bacterial infection, a protozoal infection, or cell proliferation in a subject which comprises administering to the subject a therapeutically effect amount of at least one compound of the present invention or a mixture of the present invention. In preferred embodiments, the bacterial infection is caused by an organism belonging to *Mycobacterium*, preferably *Mycobacterium tuberculosis*. In preferred embodiments, the protozoal infection is caused by a *Plasmodium* parasite, preferably, *P. falciparum, P. vivax, P. ovale*, or *P. malariae*. In some embodiments, the *Plasmodium* parasite is resistant to an antimalarial drug such as quinine, mefloquine, primaquine, hydroxychloroquine, sulfadoxine, doxycycline, chloroquine, or pyrimethamine.

In some preferred embodiments, the disease or disorder associated with cell proliferation is cancer, papillomas, acute and chronic inflammation, rheumatoid arthritis, psoriasis, atherosclerosis, diabetic retinopathy, chronic obstructive pulmonary disorder, tuberculosis, chronic cholecystitis, osteoarthritis, rheumatic carditis, bronchiectasis, Hashimoto's thyroiditis, inflammatory bowel diseases such as ulcerative colitis and Crohn's disease, silicosis, or the like. In preferred embodiments, the cancer is leukemia, CNS cancer, renal cancer, non-small cell lung cancer, melanoma, prostate cancer, colon cancer, ovarian cancer, or breast cancer.

In some embodiments, the present invention provides a method for making a compound having the structural formula 1 which comprises reacting a compound having the following structural formula 2

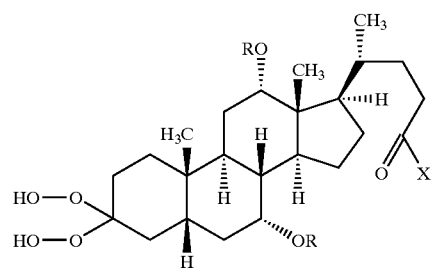

wherein

R is H, ethanoyl, propanoyl, or benzoyl;
X is a $C_1$–$C_4$ straight or branched-chain alkoxy, primary amino, N-alkylamino wherein the alkyl is a straight-chain alkyl group containing from 1 to 4 carbon atoms, methyl ethanoate-2-yl, N-phenylamino, p-nitrophenyl, N,N-dimethylamino, N,N-diethylamino, N,N-di(n-propyl)amino, N-pyrrolidino, or N-piperidino with a compound having the structural formula 3

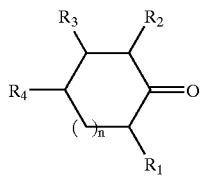

wherein
n is 0, 1, 2, or 3;
R1 is H;
R2 is H;
R3 is H;
R4 is a straight or branched-chain alkyl containing from 1 to 3 carbon atoms, phenyl which may be substituted by one or more substituents selected from the group consisting of halogen, hydroxy, $C_1$–$C_2$ alkoxy, $C_1$–$C_2$ alkyl, nitro or $CF_3$; or

wherein Y is all $C_1$–$C_4$ straight or branched-chain alkoxy, or

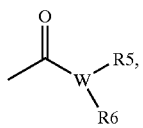

wherein W is N; R5 is hydrogen, a $C_1$–$C_4$ straight or branched-chain alkyl, a $C_1$–$C_4$ straight or branched-chain alkyl ethanoate 2-yl, ethanoic acid 2-yl, phenyl which may be substituted by one or more substituents selected from the group consisting of halogen, $C_1$–$C_2$ alkoxy, $C_1$–$C_2$ alkyl or $CF_3$; and R6 is hydrogen, a $C_1$–$C_4$ straight or branched-chain alkyl, or R5 and R6 are part of a pyrrolidine or piperidine ring, in a solvent.

In preferred embodiments, the solvent is toluene, benzene, ether, THF, $CH_3CN$, $CH_2Cl_2$, or mixtures thereof, preferably $CH_2Cl_2$. In preferred embodiments, the reaction is conducted at a temperature range of about −35° C. to about 10° C. for about 3 to about 240 minutes, preferably about 0° C. for about 15 minutes. In some embodiments, a catalyst is used. Preferably, the catalyst is sulfuric acid dissolved in $CH_3CN$.

In some embodiments, the present invention provides a method for making a compound having the structural formula 1 which comprises reacting compound having the following structural formula 4

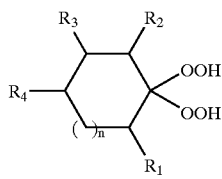

wherein
n is 0, 1, 2, or 3;
R1 is H;
R2 is H;
R3 is H;
R4 is H, a straight or branched-chain alkyl group containing from 1 to 3 carbon atoms, phenyl which may be substituted by one or more substituents selected from the group consisting of halogen, hydroxy, $C_1$–$C_2$ alkoxy, $C_1$–$C_2$ alkyl, nitro or $CF_3$; or

wherein Y is a $C_1$–$C_4$ straight or branched-chain alkoxy, or

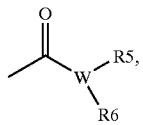

wherein W is N; R5 is hydrogen, a $C_1$–$C_4$ straight or branched-chain alkyl, a $C_1$–$C_4$ straight or branched-chain alkyl ethanoate 2-yl, ethanoic acid 2-yl, or phenyl which may be substituted by one or more substituents selected from the group consisting of halogen, $C_1$–$C_2$ alkoxy, $C_1$–$C_2$ alkyl or $CF_3$; and R6 is hydrogen, a $C_1$–$C_4$ straight or branched-chain alkyl, or R5 and R6 are part of a pyrrolidine or piperidine ring
with a compound of the structural formula 5

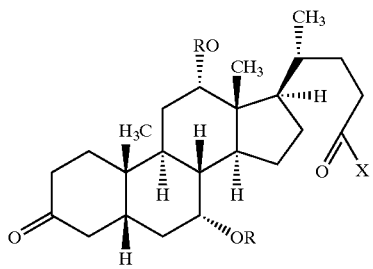

wherein R are each independently H, ethanoyl, propanoyl, or benzoyl;
X is a $C_1$–$C_4$ straight or branched-chain alkoxy, primary amino, N-alkylamino wherein the alkyl is a straight-chain alkyl group containing from 1 to 4 carbon atoms, methyl ethanoate-2-yl, N-phenyl amino, p-nitrophenyl, N,N-dimethylamino, N,N-diethylamino, N,N-di(n-propyl) amino, N-pyrrolidino, or N-piperidino, in a solvent.

In preferred embodiments, the solvent is toluene, benzene, ether, THF, $CH_3CN$, $CH_2Cl_2$, or mixtures thereof, preferably $CH_2Cl_2$. In preferred embodiments, the reaction is conducted at a temperature range of about −35° C. to about 10° C. for about 3 to about 240 minutes, preferably about 0° C. for about 15 minutes. In some embodiments, a catalyst is used. Preferably, the catalyst is sulfuric acid dissolved in $CH_3CN$.

In some embodiments, the present invention provides a method for making the compound having the structural formula 1 which comprises reacting the compound having the structural formula 1 with LiOH, NaOH, or KOH in a solvent mixture of $CH_2Cl_2$-MeOH, or $CH_2Cl_2$-EtOH at about 20 to about 25° C., or in a solvent mixture of i-PrOH—$H_2O$ (1-9:9-1, v/v) at about 79° C. for for about 10 to about 60 minutes, cooling to room temperature, diluting with water and a non-reacting organic solvent, and water layer acidifying to pH 2 with diluted HCl. In preferred embodiments, the non-reacting organic solvent is $CH_2Cl_2$.

In some embodiments, the present invention provides a method for making the compound having the structural formula 1 which comprises reacting the acid of the compound having the structural formula 1 with $ClCO_2Et$ in the presence of an organic base and then adding ammonia, primary amine, secondary amine, or an ammonium salts thereof and tertiary base. In preferred embodiments, the organic base is $Et_3N$, in $CH_2Cl_2$.

In some embodiments the present invention provides a method for making a compound having the structural formula 2 which comprises reacting a compound having the structural formula 5

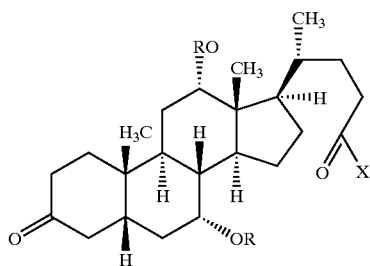

5 wherein R are each independently H, ethanoyl, propanoyl, or benzoyl;

X is a $C_1$–$C_4$ straight or branched-chain alkoxy, primary amino, N-alkylamino wherein the alkyl is a straight-chain alkyl group containing from 1 to 4 carbon atoms, methyl ethanoate-2-yl, N-phenyl amino, p-nitrophenyl, N,N-dimethylamino, N,N-diethylamino, N,N-di(n-propyl) amino, N-pyrrolidino, or N-piperidino, with a ten molar excess of a water solution comprising 30% $H_2O_2$ in a $CH_3CN$—$CH_2Cl_2$ (1-9:9-1 v/v) solvent mixture, in the presence of about 1 to 11 μl of concentrated HCl, at about 0 to about 30° C., for about 30 to about 480 minutes, extracting with $CH_2Cl_2$, and then neutralizing with a saturated solution of $NaHCO_3$.

In some embodiments, the present invention provides a method for making a compound having the structural formula 4 which comprises reacting a compound having the structural formula 3

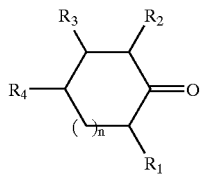

3 wherein
n is 0, 1, 2, or 3;
R1 is H;
R2 is H;
R3 is H;
R4 is a straight or branched-chain alkyl containing from 1 to 3 carbon atoms, phenyl which may be substituted by one or more substituents selected from the group consisting of halogen, hydroxy, $C_1$–$C_2$ alkoxy, $C_1$–$C_2$ alkyl, nitro or $CF_3$; or

wherein Y is all $C_1$–$C_4$ straight or branched-chain alkoxy, or

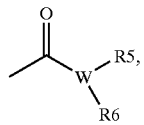

wherein W is N; R5 is hydrogen, a $C_1$–$C_4$ straight or branched-chain alkyl, a $C_1$–$C_4$ straight or branched-chain alkyl ethanoate 2-yl, ethanoic acid 2-yl, phenyl which may be substituted by one or more substituents selected from the group consisting of halogen, $C_1$–$C_2$ alkoxy, $C_1$–$C_2$ alkyl or $CF_3$; and R6 is hydrogen, a $C_1$–$C_4$ straight or branched-chain alkyl, or R5 and R6 are part of a pyrrolidine or piperidine ring, with a ten molar excess of a water solution of 30% $H_2O_2$ in a $CH_3CN$—$CH_2Cl_2$ (1-9:9-1 v/v) solvent mixture, in the presence of about 1 to about 11 μl of concentrated HCl, at about 0 to about 30° C., for about 30 to about 480 minutes, extracting with $CH_2Cl_2$, and neutralizing with a saturated solution of $NaHCO_3$.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein:

FIG. 1 shows 9 graphs representing the dose response curves obtained for compound 1C44 for the given cancer cell lines.

FIG. 2 shows a table which provides the does reponse data for compound 1C44 for the given cancer cell lines.

DETAILED DESCRIPTION OF THE INVENTION

Figure 1A:
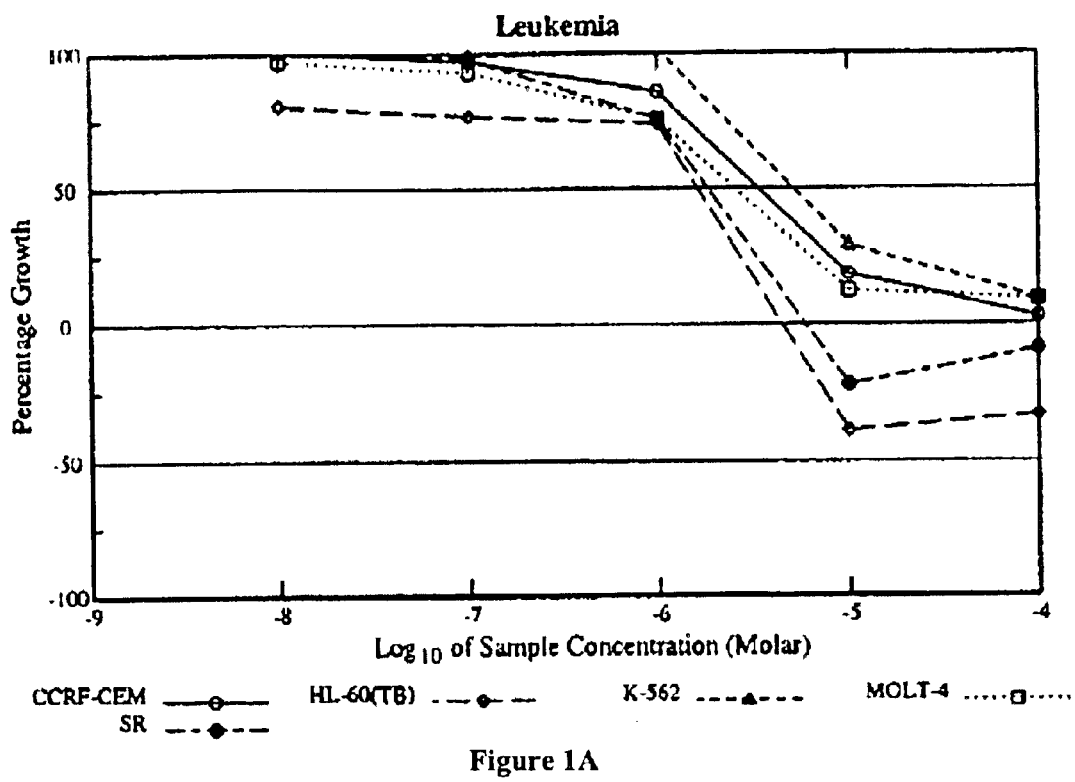
FIG. 1A shows the leukemia cell lines.

Dispiro-1,2,4,5-tetraoxacycloalkane (tetraoxane) compounds are a class of organic compounds that comprise two spirocycloalkyl carbons linked with two peroxide bridges. In general, dispirocycloalkyl-substituted tetraoxane compounds may comprise two identical spirocycloalkyl frameworks (bis(spirocycloalkyl)tetraoxanes), or of two different spirocycloalkyl frameworks (mixed tetraoxanes).

A 1,2,4,5-tetraoxacyclohexane (tetraoxane) ring (or moiety) as follows:

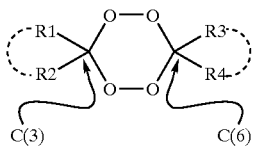

can be substituted at carbons C(3) and C(6). The substituents may be identical (R1=R2=R3=R4), or non-identical (R1≠R2≠R3≠R4). The substituents may form a ring (R1, R2 one ring, and R3, R4 another, dotted lines).

As used herein, tetraoxane compounds having all identical substituents are referred to as "bis-substituted tetraoxane" compounds. "Bis-substituted tetraoxane" compounds also include those where the rings are identical. However, one may have non-identical substituents joined to C(3) and C(6). That situation may occur where:

a. R1≠R2≠R3≠R4, or (R1=R2) ≠(R3≠(R4) or (R1=R2) ≠R3=R4)

b. non-identity of the rings or substituents, e.g.,

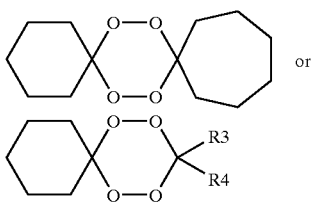

c. non-identity of the rings (substituents in general) may occur due to different substitution pattern on the attached rings, e.g.,

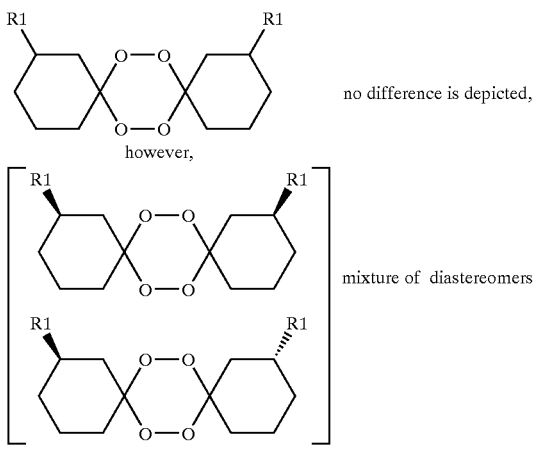

See e.g. Opsenica, et al. (2000) J. Med. Chem. 43: 3274–3282, which is herein incorporated by reference. Two "bis-substituted tetraoxane" compounds may have the same steroidal substituent (a part of a steroid moiety: in this case the cholic acid residue) joined through the spiro carbon with the tetraoxane ring (tetraoxane ring carbons C(3) and C(6)), however, the cholic acid residues may be joined in two different ways, thereby giving rise to two diastereomers.

Some chemists use "unsymmetrically substituted 1,2,4,5-tetroxanes" and "unsymmetrical tetraoxane" to refer to tetraoxane compounds substituted at C(3) and C(6) with non-identical substituents. See e.g. Kim et al. (1999) J. Chem. Soc., Perkin Trans. 1867–1870 and International Patent Application No. WO 93/07119, which are herein incorporated by reference. However, a whole tetraoxane molecule (a 1,2,4,5-tetraoxacyclohexane moiety together with given substituents at C(3) and C(6)) can possess elements of symmetry, for example, compound 8 disclosed in Opsenica, et al. (2000) is C2 symmetrical.

Therefore, as used herein, a "mixed" tetraoxane compound refers to a compound possessing the tetraoxane moiety substituted with different substituents at C(3) and C(6). As used herein, "mixed steroidal 1,2,3,5-tetraoxane" compounds refers to a tetraoxacyclohexane ring having a steroidal substituent joined through the spiro carbon and therein the tetraoxacyclohexane ring is further substituted through the opposite spiro carbon with various cycloalkyl substituents.

Bis(spirocycloalkyl)tetraoxanes may be obtained in peroxyacetalization reaction from a ketone and $H_2O_2$, in the presence of an acid catalyst in the solvents such as EtOH, $CH_2Cl_2$, $CH_3CN$. See Kbarasch, M. S. et al. (1958) J. Org. Chem. 23:1322–1326; Sanderson, J. R. et al. (1975) Synthesis 159–161; McCullough, K. J. et al. (1980) J. Chem. Research (S) 34; McCullogh, K. J. et al. (2000) J. Med. Chem. 43:1246–1249; Vennerstrom, J. L. et al. (1992) J. Med. Chem. 35:3023–3027; Vennerstrom, J. L. et al. (2000) J. Med. Chem. 43:2753–2758; and Dong, Y. et al. (1999) J. Med. Chem. 42:1477–1480, which are herein incorporated by reference.

Generally, the acid catalysts used were $HClO_4$ and $H_2SO_4$. Bis-steroidal tetraoxanes of cholestane series have been prepared from 5α- or 5β-cholestan-3-ones and 30% $H_2O_2$ in THF (or benzene-EtOH mixture) in the presence of 37% HCl, or concentrated $H_2SO_4$. See Todorovic, N. M. et al. (1996) Steroids 61:688–696, which is herein incorporated by reference. Bis-steroidal tetraoxanes have been synthesized from 3-oxo cholic acid derivatives. See Opsenica, D. et al. (2000) J. Med. Chem. 43:3274–3282, which is herein incorporated by reference. 30% $H_2O_2$ in toluene and $H_2SO_4$ as catalyst were used for alkyl 3-oxo-7α,12α-diacetoxy-5β-cholan-24-oates, while the tetraoxanes of corresponding 24-amides were prepared using an anhydrous variant of this reaction. See Jefford, C. W. et al. (1988) Synthesis 391–393, which is herein incorporated by reference. The processes for preparation of bis(spirocycloalkyl)tetraoxanes have been disclosed in several patents. See e.g. U.S. Pat. No. 3,116,300, which is herein incorporated by reference. The products obtained, however, were purely characterized not taking into account the possibility of contamination with the corresponding tricycloalkylidene peroxides.

U.S. Pat. Nos. 3,880,882 and 3,925,417 discloses and claims that mixed tetraoxanes can be prepared by decomposition of mixed tricycloalkylidene peroxides, however, the products were purely characterized usually using indirect methods, and often were obtained as impure products not suitable for intended purpose of present disclosure. In addition to the methods described in above given patents, mixed tetraoxanes may also be prepared by coupling of a 1,1-dihydroperoxide to a ketone or aldehyde. Kim et al. for the first time synthesized mixed tetraoxanes starting with enol ethers of formyl alkanes to obtain in the first step a 1,1-dihydroperoxide. See Kim, H. S., et al. (1999) J. Chem. Soc., Perkin Trans. 1867–1870, which is herein incorporated by reference. The method of preparation embraced the ozonolysis of enol ethers of formyl alkanes in dry etheral extract of $H_2O_2$. Such obtained 1,1-dihydroperoxide was in the next step protected as bis-TMS ether using BSA. Bis-TMS ether in the third, TMSOTf-catalyzed, step reacted with a ketone to give mixed tetraoxanes in 2–23% overall yield.

As disclosed herein, the compounds of the present invention may be prepared using a simple procedure by coupling the desired ketone to a gem-dihydroperoxide, which in turn is prepared from a different ketone in a simple manner. This method is easier, less complicated, and more economical as compared to the method of Kim, H. S., et al. (1999). Specifically, the method of making the tetraoxane compounds of the present invention is simple as it uses the commercial ca. 30% $H_2O_2$ (water solution) and provides high yields of gem-dihydroperoxides unlike Warnant, J. et al. who used a $H_2O_2$ solution in absolute solvents. See Warnant, J. et al. (1957) Bull. Soc. Chim. France 331–332; Velluz, L. et al. (1957) Bull. Soc. Chim. France 879–882; UK Patent Specification 842,922 (14 Jun. 1957), which are herein incorporated by reference. Additionally, the method of making the tetraoxane compounds of the present invention provides new coupling conditions of gem-dihydroperoxides to ketones which utilizes simple reagents and conditions and allows two different substituents that can be modified in a selective manner, thereby allowing the preparation of greater number of mixed tetraoxane compounds.

As disclosed herein, the present invention provides cycloalkyl-spiro-1,2,4,5-tetraoxacyclohexane-spiro-cholic acids and derivatives thereof (hereinafter steroidal mixed tetraoxanes) having the following structural formula 1:

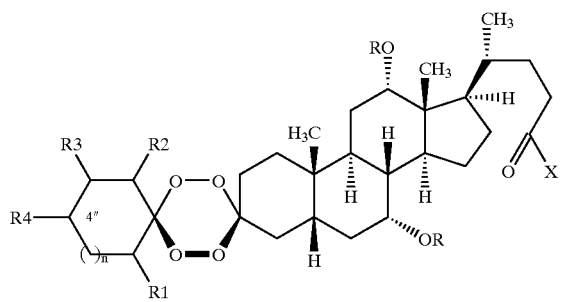

wherein n is 0, 1, 2, or 3;
R is H, ethanoyl, propanoyl, or benzoyl;
R1 is H, methyl, ethyl, or isopropyl;
R2 is H, methyl, or ethyl;
R3 is H, methyl, or ethyl;
R4 is H, methyl, ethyl, tert-butyl, phenyl, p-hydroxyphenyl, p-methoxyphenyl, or p-nitrophenyl, or

wherein Y is all $C_1$–$C_4$ straight or branched-chain alkoxy, or

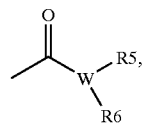

wherein W is N, R5 is hydrogen, methyl, ethyl, n-propyl, isopropyl, or methyl ethanoate 2-yl, and R6 is hydrogen; methyl, ethyl, or n-propyl, or R5 and R6 are part of a pyrrolidine or piperidine ring;

X is a $C_1$–$C_4$ straight or branched-chain alkoxy, a primary amino, a N-alkylamino wherein the alkyl is a straight-chain alkyl groups containing from 1 to 4 carbon atoms, methyl ethanoate-2-yl, or a N-phenylamino, p-nitrophenyl, N,N-dimethylamino, N,N-diethylamino, N,N-di(n-propyl)amino, N-pyrrolidino, or N-piperidino.

The present invention also provides the geminal dihydroperoxides used for production of steroidal mixed tetraoxanes, in particular, the gem-dihydroperoxides of cholic acid and derivatives thereof, and 1,1-dihydroperoxy (susbstituted)cycloalkanes.

The steroidal mixed tetraoxanes of this invention can be produced in accordance with Scheme 1.

Scheme 1

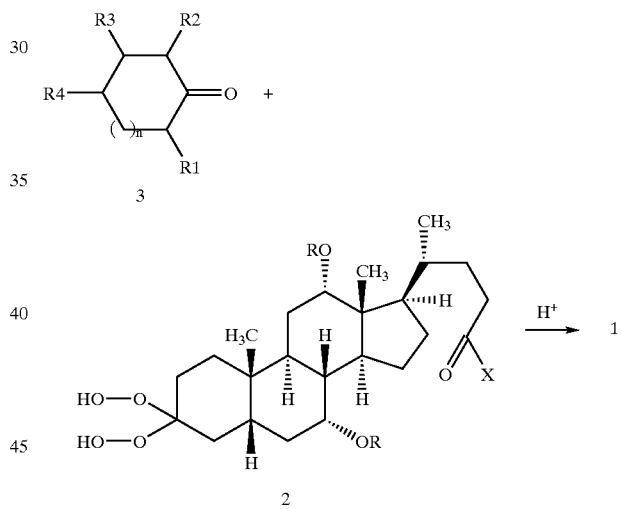

wherein n is 0, 1, 2, or 3;
R is H, ethanoyl, propanoyl, or benzoyl;
R1 is H, methyl, ethyl, or isopropyl;
R2 is H, methyl, or ethyl;
R3 is H, methyl, or ethyl;
R4 is H, methyl, ethyl, tert-butyl, phenyl, p-hydroxyphenyl, p-methoxyphenyl, or p-nitrophenyl, or

wherein Y is all $C_1$–$C_4$ straight or branched-chain alkoxy, or

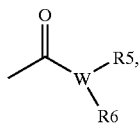

wherein W is N, R5 is hydrogen, methyl, ethyl, n-propyl, isopropyl, or methyl ethanoate 2-yl, and R6 is hydrogen; methyl, ethyl, or n-propyl, or R5 and R6 are part of a pyrrolidine or piperidine ring;

X is a $C_1$–$C_4$ straight or branched-chain alkoxy, a primary amino, a N-alkylamino wherein the alkyl is a straight-chain alkyl groups containing from 1 to 4 carbon atoms, methyl ethanoate-2-yl, or a N-phenylamino, p-nitrophenyl, N,N-dimethylamino, N,N-diethylamino, N,N-di(n-propyl)amino, N-pyrrolidino, or N-piperidino.

The steroidal gem-dihydroperoxides may be synthesized from corresponding ketones using anhydrous $H_2O_2$ solutions without catalyst or using 30% $H_2O_2$ with catalyst according to conventional methods known in the art. See Warnant, J. et al. (1957) Bull. Soc. Chim. France 331–332; Velluz, L. et al. (1957) Bull. Soc. Chim. France 879–882; UK Patent Specification 842,922 (14 Jun. 1957); and Todorović, N. M. et al. (1996) Steroids 61:688–696, which are herein incorporated by reference. In the first step a ketone may be transformed using the excess of 30% $H_2O_2$ and HCl as catalyst in $CH_3CN$—$CH_2Cl_2$ solvent mixture at 0–30° C., preferably 22° C., into gem-dihydroperoxide. In the second step, such prepared gem-dihydroperoxide may be coupled to a ketone, differing from the one used in the first step, in benzene, toluene, ether, THF, $CH_2Cl_2$, or their mixtures, preferably $CH_2Cl_2$, at −35° C.–+10° C., preferably 0° C., using as catalyst the sulfuric acid dissolved in $CH_3CN$.

Alternatively, in some cases the compounds of this invention can be prepared in accordance with Scheme 2:

Scheme 2

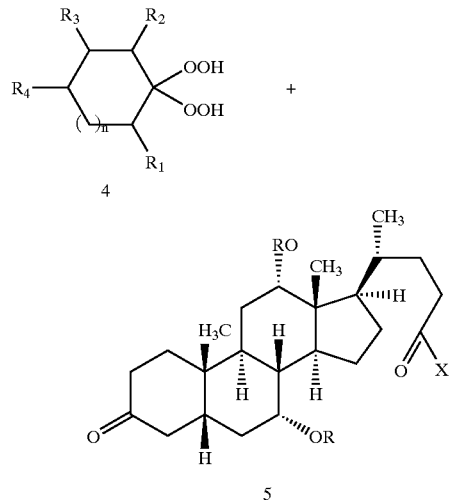

wherein n is 0, 1 and 3;
R is H; ethanoyl, propanoyl, or benzoyl;
R1 is H or alkyl wherein alkyl is methyl, ethyl, or isopropyl;
R2 is H, methyl, or ethyl;
R3 is H, methyl, or ethyl;
R4 is H, methyl, ethyl, phenyl, p-hydroxyphenyl, p-methoxyphenyl, p-nitrophenyl, or

wherein Y is all $C_1$–$C_4$ straight or branched-chain alkoxy, or

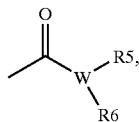

wherein W is N, R5 is hydrogen; methyl, ethyl, n-propyl, isopropyl, or methyl ethanoate 2-yl, and R6 is hydrogen; methyl, ethyl, or n-propyl, or R5 and R6 are part of a pyrrolidine or piperidine ring;

X is a $C_1$–$C_4$ straight or branched-chain alkoxy, a primary amino, a N-alkylamino wherein the alkyl denotes all straight-chain alkyl groups containing from 1 to 4 carbon atoms, methyl ethanoate-2-yl, or a N-arylamino wherein the aryl is phenyl, p-nitrophenyl, N,N-dimethylamino, N,N-diethylamino, N,N-di(n-propyl)amino, N-pyrrolidino, or N-piperidino.

As provided herein, the mixed tetraoxanes of the present invention may be prepared in two steps. In the first step a ketone is transformed using an excess of about 30% $H_2O_2$ and HCl as catalyst in $CH_3CN$—$CH_2Cl_2$ solvent mixture at about 0 to about 30° C., preferably at about 22° C., into gem-dihydroperoxide. In the second step, such prepared gem-dihydroperoxide was coupled to a ketone, differing from the one used in the first step, in benzene, toluene, ether, THF, $CH_2Cl_2$, or their mixtures, preferably in $CH_2Cl_2$, at about −35° C. to about +10° C., preferably about 0° C., using as catalyst the sulfuric acid dissolved in $CH_3CN$.

Specifically, some of the mixed tetraoxanes of the present invention were synthesized according to the following synthetic Scheme 3:

Scheme 3

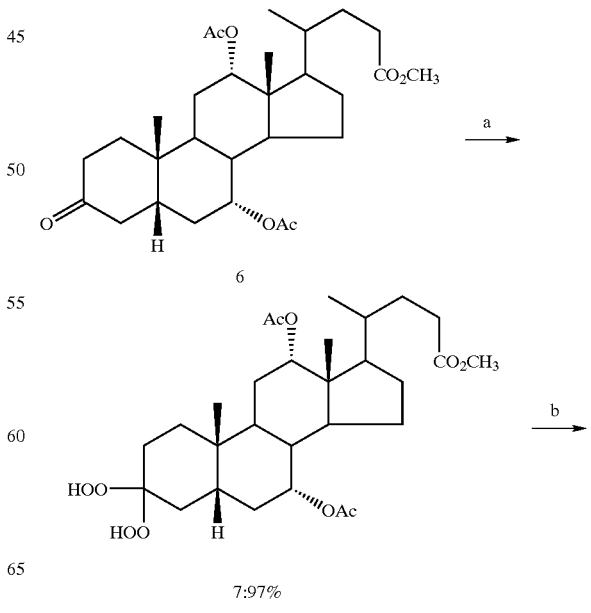

-continued

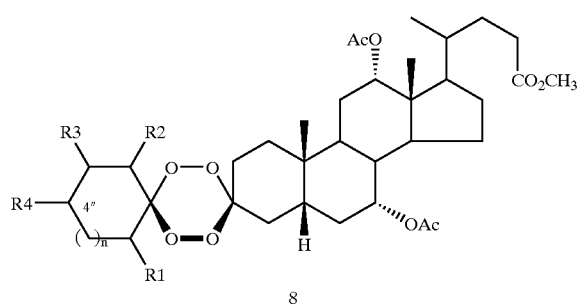

8 a) 30% H₂O₂, HCl, CH₂Cl₂, CH₃CN;
b) ketone, CH₂Cl₂, 0° C., H₂SO₄, CH₃CN

KETONE

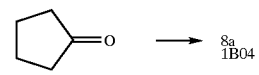 → 8a 1B04

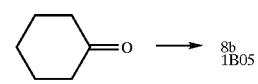 → 8b 1B05

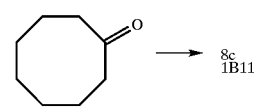 → 8c 1B11

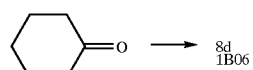 → 8d 1B06

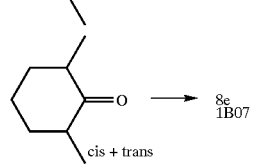 → 8e 1B07 cis + trans

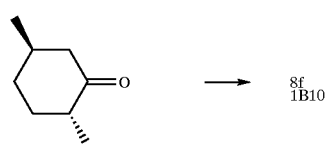 → 8f 1B10

(-)-menthone

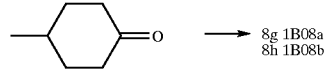 → 8g 1B08a
8h 1B08b

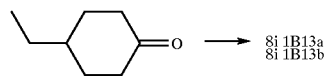 → 8i 1B13a
8i 1B13b

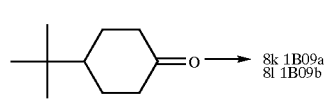 → 8k 1B09a
8l 1B09b

-continued

8a: R1 = R2 = R3 = R4 = H; n = 0; 26%
8b:                         n = 1; 31%
8c:                         n = 3; 34%
n = 1
8d: R1 = CH₃, R2 = R3 = R4 = H; 38%
8e: 1 = R2 = CH₃, R2 = R4 = H; 25%
8f: R1 = i-Pr, R3 = CH₃, R2 = R4 = H; 19%
8g: R4 = (4"R) CH₃, R1 = R2 = R3 = H; 12%
8h: R4 = (4"S) CH₃, R1 = R2 = R3 = H; 12%
8i: R4 = (4"R or S) Et, R1 = R2 = R3 = H; 15%
8j: R4 = (4"S or R) Et, R1 = R2 = R3 = H; 12%
8k: R4 = (4"R or S) t-Bu, R1 = R2 = R3 = H; 11%
8l: R4 = (4"S or R) t-Bu, R1 = R2 = R3 = H; 28%

Methyl 3,3-dihydroperoxy-7α,12α-diacetoxy-5β-cholan-24-oate (7), was prepared in high yield by modification of the previously reported procedure, using 30% H₂O₂/CH₂Cl₂/CH₃CN reaction medium. See Todorović, N. M. et al. (1996) Steroids 61:688–696, and references cited therein, which are herein incorporated by reference. Crude 3,3-dihydroperoxide 7 was then treated with the corresponding ketone in the presence of sulfuric acid as catalyst, at 0° C., and the overall reaction time was ca. 15 min.

Simple ketones reacted well with gem-dihydroperoxide 7 affording mixed tetraoxanes 8a–8l. See Scheme 3. As expected, non-substituted cycloalkanones gave single products (8a–8c), while substituted precursors afforded diastereomeric mixtures. 4"-methyl-, 4"-ethyl- and 4"-t-butyltetraoxane mixtures were separated into corresponding diastereomers (8g, 8h; 8i, 8j and 8k, 8l, respectively); 2-methylcyclohexanone, 2,6-dimethylcyclohexanone ((cis+trans)-mixture), and (−)-menthone afforded non-resolvable diastereomeric mixtures 8d, 8e and 8f, respectively.

The configuration at C(4") in 8h was assigned by X-ray crystallographic structural analysis of the corresponding acid 9h and it appears to be S. See Spek, A. L. *PLUTON Program for molecular graphic* (1992) University of Utrecht, The Netherlands. The 6-membered 1,2,4,5-tetraoxane and methylcyclohexane rings adopted conformations very similar to chair forms: the puckering parameters being Q=0.646 Å, θ=3.5°, φ=315.5° for the first and Q=0.559 Å, θ=3.9°, φ=215.1° for the second. See Cremer, D., et al. (1975) J. Am. Chem. Soc. 97:1354–1358, which is herein incorporated by reference. The methyl substituent is in axial position. A hydrogen bond between the carboxylic group and one of the carbonyl function of a symmetry related molecule is observed: O25 . . . O29 (x, y−1,z)=2.700 (3) Å. The complete data, atomic parameters and geometry are given as supporting information. Consequently, it is reasonable to propose the (4"R)-configuration of the corresponding carbon in diastereomer 8g.

The coupling conditions afforded tetraoxanes in good yield (about 24 to about 39%), except in the case of menthone where α-isopropyl substituent lowers the yield even more than two methyls in 2,6-dimethylcyclohexanone.

Tetraoxanes possessing carboxylic acid termini render poor in vitro antimalarial activity as compared to corresponding esters. See Dong, Y., et al. (1999) J. Med. Chem. 42:1477–1480, which is herein incorporated by reference. Since it is feasible to anticipate that an ester moiety would easily hydrolyze in vivo, in order to secure a non-acidic protic group to facilitate the solubility in polar solvents, tetraoxanes 8b, 8d, and 8g–8j were further transformed into amide derivatives 10–11, 13–16, and 17–32, respectively, via mixed anhydrides an overall yield of about 53 to about 81% according to Scheme 4 as follows:

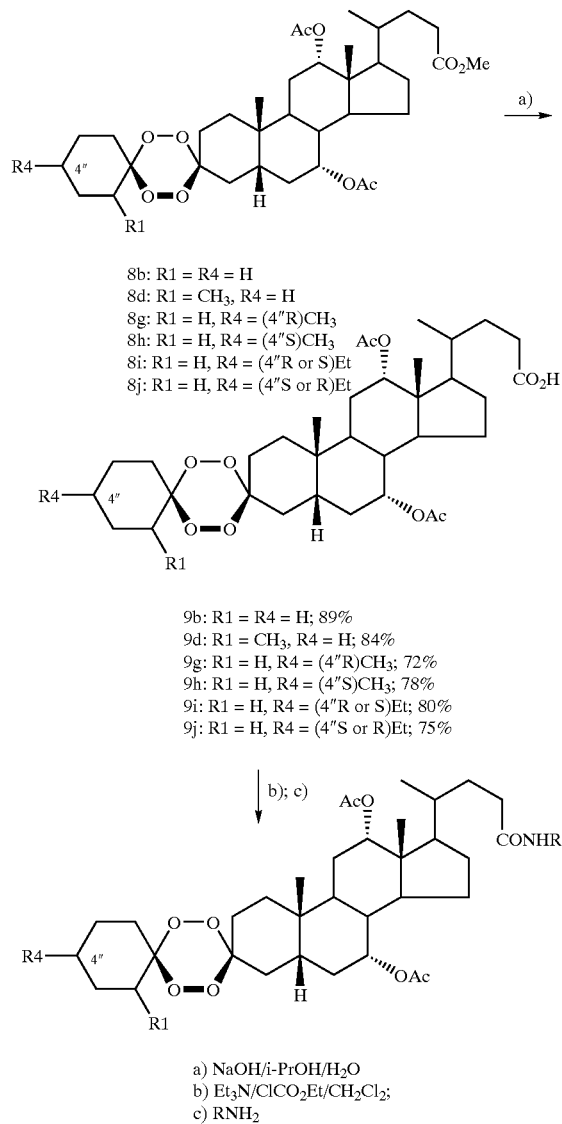

8b: R1 = R4 = H
8d: R1 = CH₃, R4 = H
8g: R1 = H, R4 = (4″R)CH₃
8h: R1 = H, R4 = (4″S)CH₃
8i: R1 = H, R4 = (4″R or S)Et
8j: R1 = H, R4 = (4″S or R)Et

9b: R1 = R4 = H; 89%
9d: R1 = CH₃, R4 = H; 84%
9g: R1 = H, R4 = (4″R)CH₃; 72%
9h: R1 = H, R4 = (4″S)CH₃; 78%
9i: R1 = H, R4 = (4″R or S)Et; 80%
9j: R1 = H, R4 = (4″S or R)Et; 75% a) NaOH/i-PrOH/H₂O
b) Et₃N/ClCO₂Et/CH₂Cl₂;
c) RNH₂

R1 = R4 = H
10:R = H; 89%. 11:R = nPr; 70%.
12:R = CH₂CO₂CH₃; 64%. R = CH₃, R4 = H
13:R = H; 68%.
14:R = CH₃; 64%. 15:R = Et; 96%.
16:R = nPr; 70%. R1 = H, R4 = (4R)CH₃
17:R = H; 74%
18:R = CH₃; 82%. 19:R = Et; 90%.
20:R = nPr; 74%. R1 = H,R4 = (4S)CH₃
21:R = H; 76%.
22:R = CH₃; 70%. 23:R = Et; 90%.
24:R = nPr; 70%. R1 = H, R4 = (4R or S)Et
25:R = H; 85%. 26:R = CH₃; 76%.
27:R = Et; 82%. 28:R = nPr; 79%.
  R1 = H, R4 = (4S or R)Et 29:R = H; 79%.
30:R = CH₃; 77%. 31:R = Et; 75%. 32:R = nPr; 77%.

Applying the mixed anhydride procedure on a compound with tetraoxane functionality opens a new approach to complex compounds of this type having significantly higher activity with respect to bis-steroidal tetraoxanes (vide infra). See Opsenica, D., et al. (2000) J. Med. Chem. 43:3274–3282, which is herein incorporated by reference.

While the reason for derivatization of the single products is obvious, the diastereomeric tetraoxane mixture 8d, obtained from racemic 2-methylcyclohexanone, was used for derivatization as a probe for testing the generality of the amide moiety effect on the activity observed earlier (vide infra).

Molecular masses of synthesized tetraoxanes were confirmed by using single-stage electrospray ionization (ESI) mass spectrometry in the positive ion mode. All analyzed compounds yield abundant molecular ion peaks by coordinating ammonium, sodium, and potassium ions ($[M+NH_4]^+$, $[M+Na]^+$ and $[M+K]^+$, respectively).

Alternatively, the mixed tetraoxanes of the present invention may be made according to the following Scheme 5:

Scheme 5

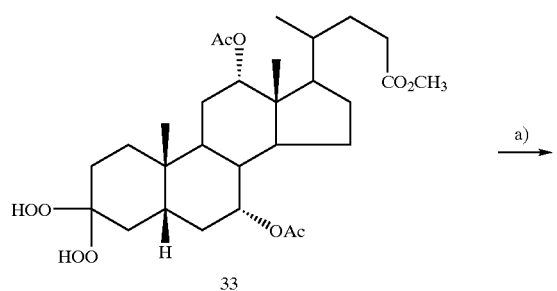

33 a) ketone, CH₂Cl₂, 0° C., H₂SO₄/CH₃CN
b) NaOH/i-PrOH/H₂O, 80° C.;
c) Et₃N/ClCO₂Et/CH₂Cl₂, RNH₂.

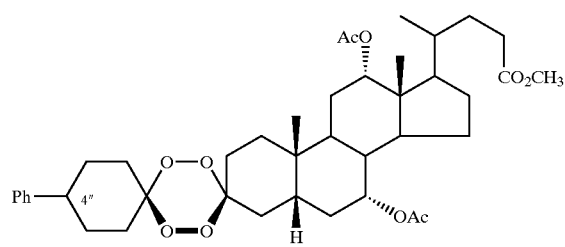
34 (4″R or S); 15%
b)
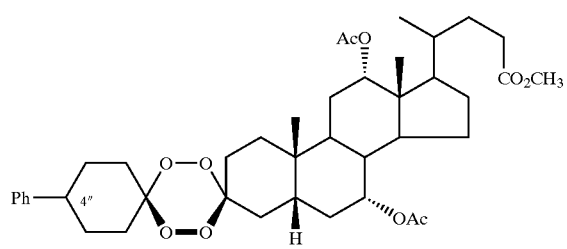
35 (4″S or R); 12%
b)
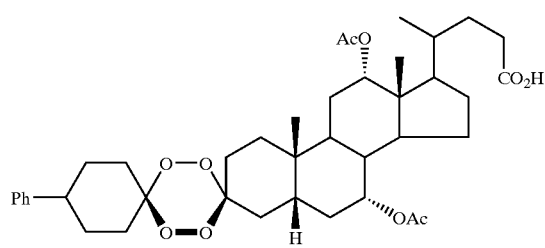
36 (4″R or S); 88%
c)
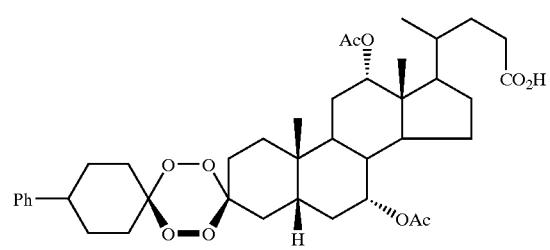
37 (4″S or R); 93%
c)
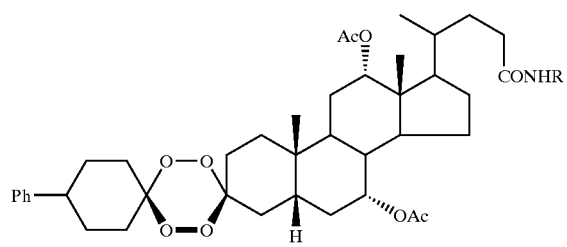
38: R = H; (4″R or S); 79%
40: R = Me; (4″R or S); 78%
42: R = Et; (4″R or S); 80%
44: R = n-Pr; (4″R or S); 76%
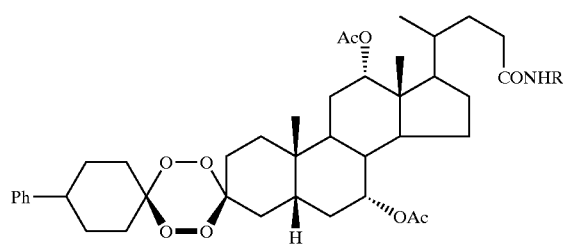
39: R = H; (4″S or R); 86%
41: R = Me; (4″S or R); 83%
43: R = Et; (4″S or R); 84%
45: R = n-Pr; (4″S or R); 78%

Therefore, the present invention provides a new and simple synthesis of dispirocycloalkyl-1,2,4,5-tetraoxacyclohexanes, a new generation of tetraoxanes with cholic acid derivatives as a carrier.

The mixed tetraoxanes of the present invention have valuable pharmaceutical properties. In particular, the steroidal mixed tetraoxanes, as provided in Example 56 and as shown in Table 1, exhibit excellent activity against malaria pathogens as provided in Table 2. In most cases their activity is higher against chloroquine-resistant strain than against chloroquine-susceptible strain.

TABLE 1

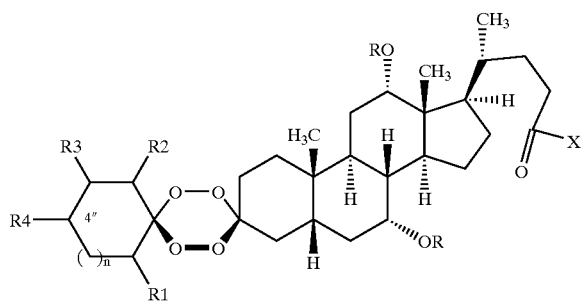

| | R | R1 | R2 | R3 | R4 | X | Comp. No. |
|---|---|---|---|---|---|---|---|
| n = 0 | Ethanoyl | H | H | H | H | $OCH_3$ | 8a/1B04 |
| n = 1 | Ethanoyl | H | H | H | H | $OCH_3$ | 8b/1B05 |
| | Ethanoyl | $CH_3$ | H | H | H | $OCH_3$ | 8d/1B06 |
| | Ethanoyl | $CH_3$ | $CH_3$ | H | H | $OCH_3$ | 8e/1B07 |
| | Ethanoyl | $CH(CH_3)_2$ | H | $CH_3$ | H | $OCH_3$ | 8f/1B10 |
| | Ethanoyl | H | H | H | $H_3C$—C(4"R) | $OCH_3$ | 8g/1B08a |
| | Ethanoyl | H | H | H | $H_3C$—C(4"S) | $COH_3$ | 8h/1B08b |
| | Ethanoyl | H | H | H | $(CH_3)_3C$—C(4"R or S) | $OCH_3$ | 8k/1B09a |
| | Ethanoyl | H | H | H | $(CH_3)_3C$—C(4"S or R) | $OCH_3$ | 8l/1B09b |
| | Ethanoyl | H | H | H | $CH_3CH_2OOC$—C(4"R or S) | $OCH_3$ | 1B12a |
| | Ethanoyl | H | H | H | $CH_3CH_2OOC$—C(4"S or R) | $OCH_3$ | 1B12b |
| | Ethanoyl | H | H | H | $CH_3CH_2$—C(4"R or S) | $OCH_3$ | 8i/1B13a |
| | Ethanoyl | H | H | H | $CH_3CH_2$—C(4"S or R) | $OCH_3$ | 8j/1B13b |
| | Ethanoyl | H | H | H | Ph—C(4"R or S) | $OCH_3$ | 1B14a |
| | Ethanoyl | H | H | H | Ph—C(4"S or R) | $OCH_3$ | 1B14b |
| n = 3 | Ethanoyl | H | H | H | H | $OCH_3$ | Bc/1B11 |
| n = 1 | Ethanoyl | H | H | H | H | OH | 9b/1C15 |
| | Ethanoyl | H | H | H | H | $NH_2$ | 10/1C19 |
| | Ethanoyl | H | H | H | H | $NHCH_2CH_2CH_3$ | 11/1C20 |
| | Ethanoyl | H | H | H | H | $NHCH_2COOCH_3$ | 12/1C21 |
| | Ethanoyl | $CH_3$ | H | H | H | OH | 9d/1C16 |
| | Ethanoyl | $CH_3$ | H | H | H | $NH_2$ | 13/1C22 |
| | Ethanoyl | $CH_3$ | H | H | H | $NHCH_3$ | 14/1C23 |
| | Ethanoyl | $CH_3$ | H | H | H | $NHCH_2CH_3$ | 15/1C24 |
| | Ethanoyl | $CH_3$ | H | H | H | $NHCH_2CH_2CH_3$ | 16/1C25 |
| | Ethanoyl | H | H | H | $H_3C$—C(4"R) | OH | 9g/1C17 |
| | Ethanoyl | H | H | H | $H_3C$—C(4"R) | $NH_2$ | 17/1C26 |
| | Ethanoyl | H | H | H | $H_3C$—C(4"R) | $NHCH_3$ | 18/1C27 |
| | Ethanoyl | H | H | H | $H_3C$—C(4"R) | $NHCH_2CH_3$ | 19/1C28 |
| | Ethanoyl | H | H | H | $H_3C$—C(4"R) | $NHCH_2CH_2CH_3$ | 20/1C29 |
| | Ethanoyl | H | H | H | $H_3C$—C(4"S) | OH | 9h/1C18 |
| | Ethanoyl | H | H | H | $H_3C$—C(4"S) | $NH_2$ | 21/1C30 |
| | Ethanoyl | H | H | H | $H_3C$—C(4"S) | $NHCH_3$ | 22/1C31 |
| | Ethanoyl | H | H | H | $H_3C$—C(4"S) | $NHCH_2CH_3$ | 23/1C32 |
| | Ethanoyl | H | H | H | $H_3C$—C(4"S) | $NHCH_2CH_2CH_3$ | 24/1C33 |
| | Ethanoyl | H | H | H | $CH_3CH_2$—C(4"R or S) | OH | 9i/1C34 |
| | Ethanoyl | H | H | H | $CH_3CH_2$—C(4"R or S) | $NH_2$ | 25/1C35 |
| | Ethanoyl | H | H | H | $CH_3CH_2$—C(4"R or S) | $NHCH_3$ | 26/1C36 |
| | Ethanoyl | H | H | H | $CH_3CH_2$—C(4"R or S) | $NHCH_2CH_3$ | 27/1C37 |
| | Ethanoyl | H | H | H | $CH_3CH_2$—C(4"R or S) | $NHCH_2CH_2CH_3$ | 28/1C38 |
| | Ethanoyl | H | H | H | $CH_3CH_2$—C(4"S or R) | OH | 9j/1C39 |

TABLE 1-continued

| R | R1 | R2 | R3 | R4 | X | Comp. No. |
|---|----|----|----|----|----|---|
| Ethanoyl | H | H | H | $CH_3CH_2—$ $C(4"S\ or\ R)$ | $NH_2$ | 29/1C40 |
| Ethanoyl | H | H | H | $CH_3CH_2—$ $C(4"S\ or\ R)$ | $NHCH_3$ | 30/1C41 |
| Ethanoyl | H | H | H | $CH_3CH_2—$ $C(4"S\ or\ R)$ | $NHCH_2CH_3$ | 31/1C42 |
| Ethanoyl | H | H | H | $CH_3CH_2—$ $C(4"S\ or\ R)$ | $NHCH_2CH_2CH_3$ | 32/1C43 |
| Ethanoyl | H | H | H | $Ph—C(4"R\ or\ S)$ | OH | 1C44 |
| Ethanoyl | H | H | H | $Ph—C(4"R\ or\ S)$ | $NH_2$ | 1C45 |
| Ethanoyl | H | H | H | $Ph—C(4"R\ or\ S)$ | $NHCH_3$ | 1C46 |
| Ethanoyl | H | H | H | $Ph—C(4"R\ or\ S)$ | $NHCH_2CH_3$ | 1C47 |
| Ethanoyl | H | H | H | $Ph—C(4"R\ or\ S)$ | $NHCH_2CH_2CH_3$ | 1C48 |
| Ethanoyl | H | H | H | $Ph—C(4"S\ or\ R)$ | OH | 1C49 |
| Ethanoyl | H | H | H | $Ph—C(4"S\ or\ R)$ | $NH_2$ | 1C50 |
| Ethanoyl | H | H | H | $Ph—C(4"S\ or\ R)$ | $NHCH_3$ | 1C51 |
| Ethanoyl | H | H | H | $Ph—C(4"S\ or\ R)$ | $NHCH_2CH_3$ | 1C52 |
| Ethanoyl | H | H | H | $Ph—C(4"S\ or\ R)$ | $NHCH_2CH_2CH_3$ | 1C53 |

TABLE 2

Values measured in vitro ($IC_{50}$ values ng/ml) for growth inhibition of the *Plasmodium falciparum* chloroquine-susceptible strain D6, and of the chloroquine-resistant strain W2

| Compound No. | Strain D6 $IC_{50}$ | Strain W2 $IC_{50}$ | Resistance Index[a] |
|---|---|---|---|
| 8a/1B04 | 24.30 | 17.18 | 0.71 |
| 8b/1B05 | 13.63 | 10.77 | 0.79 |
| 8d/1B06 | 17.54 | 10.15 | 0.58 |
| 8e/1B07 | 20.67 | 236.70 | 11.45 |
| 8f/1B10 | 106.65 | 50.60 | 0.47 |
| 8g/1B08a | 6.48 | 3.27 | 0.50 |
| 8h/1B08b | 15.99 | 8.54 | 0.53 |
| 8k/1B09a | 74.26 | 36.43 | 0.49 |
| 8l/1B09b | 35.84 | 19.19 | 0.54 |
| 1B12a | 6.72 | 12.56 | 1.87 |
| 1B12b | 31.01 | 54.92 | 1.77 |
| 8i/1B13a | 4.46 | 9.39 | 2.10 |
| 8j/1B13b | 11.73 | 18.76 | 1.60 |
| 1B14a | 12.56 | 11.72 | 0.93 |
| 1B14b | 31.76 | 25.00 | 0.79 |
| 8c/1B11 | 32.11 | 13.26 | 0.41 |
| 9b/1B15 | 18.98 | 11.93 | 0.63 |
| 10/1C19 | 7.33 | 2.94 | 0.40 |
| 11/1C20 | 9.77 | 4.50 | 0.46 |
| 12/1C21 | 15.23 | 7.45 | 0.49 |
| 9d/1C16 | 42.93 | 23.81 | 0.56 |
| 13/1C22 | 10.97 | 7.05 | 0.64 |
| 14/1C23 | 10.22 | 6.49 | 0.64 |
| 15/1C24 | 8.37 | 4.61 | 0.55 |
| 16/1C25 | 8.89 | 6.28 | 0.71 |
| 9g/1C17 | 0.97 | 0.62 | 0.64 |
| 17/1C26 | 0.74 | 0.37 | 0.50 |
| 18/1C27 | 3.86 | 2.34 | 0.61 |
| 19/1C28 | 3.84 | 2.60 | 0.68 |
| 20/1C29 | 2.18 | 2.58 | 1.18 |
| 9h/1C18 | 19.74 | 11.26 | 0.57 |
| 21/1C30 | 12.70 | 8.94 | 0.70 |
| 22/1C31 | 10.79 | 7.69 | 0.71 |
| 23/1C32 | 10.32 | 6.57 | 0.64 |
| 24/1C33 | 57.41 | 56.11 | 0.98 |
| 9i/1C34 | 3.74 | 4.71 | 1.26 |
| 25/1C35 | 5.44 | 6.93 | 1.27 |
| 26/1C36 | 4.77 | 5.17 | 1.08 |
| 27/1C37 | 13.37 | 6.46 | 0.48 |
| 28/1C38 | 5.76 | 3.12 | 0.54 |
| 9j/1C39 | 6.38 | 9.36 | 1.47 |
| 29/1C40 | 20.12 | 8.11 | 0.40 |
| 30/1C41 | 18.50 | 4.07 | 0.22 |
| 31/1C42 | 15.64 | 12.22 | 0.78 |
| 32/1C43 | 62.20 | 84.64 | 1.36 |
| 1C44 | 6.19 | 6.09 | 0.98 |
| 1C45 | 7.19 | 7.36 | 1.02 |
| 1C46 | 8.83 | 6.96 | 0.79 |
| 1C47 | 5.41 | 5.87 | 1.08 |
| 1C48 | 6.59 | 6.72 | 1.02 |
| 1C49 | 54.24 | 43.85 | 0.81 |
| 1C50 | 40.49 | 37.46 | 0.92 |
| 1C51 | 64.62 | 54.72 | 0.85 |
| 1C52 | 32.79 | 32.58 | 0.99 |
| 1C53 | 24.28 | 24.54 | 1.01 |

TABLE 2-continued

Values measured in vitro (IC$_{50}$ values ng/ml) for growth inhibition of the
*Plasmodium falciparum* chloroquine-susceptible strain D6,
and of the chloroquine-resistant strain W2

| | *Plasmodium falciparum* | | |
|---|---|---|---|
| Compound No. | Strain D6 IC$_{50}$ | Strain W2 IC$_{50}$ | Resistance Index[a] |
| Chloroquine[b] | 3.71 | 88.28 | 23.80 |
| Mefloquine[b] | 10.62 | 2.26 | 0.21 |

[a]IC$_{50}$ (W2)/IC$_{50}$ (D6) ratio;
[b]Mean value of five experiments.

The influence of substitution was first examined by changing the spirocycloalkane substituent at the tetraoxane ring (methyl ester series 8a–8c). It was found that spirocyclohexane moiety afforded the most active compound (8b: IC$_{50}$ (D6)=13.63 ng/ml, IC$_{50}$ (W2)=10.77 ng/ml) although the resistance index (RI=IC$_{50}$(W2)/IC$_{50}$(D6)) for 8c was ca. 2 times better. Further analysis of methyl ester series revealed that substitution at C(4") position of the spirocyclohexane ring afforded further structure activity relationship information: remarkably different activity of epimers on both clones, with average RI for 4"-methyl and 4"-t-butyl isomers being 0.52.

Based on previous findings, the influence of amide functionality on antimalarial activity within the series was evaluated. See Opsenica, D. et al. (2000) J. Med. Chem. 43:3247–3282, which is herein incorporated by reference. First relevant information was obtained from the spirocyclohexane series (8b→10–12, Table 2), and as expected all amide derivatives were more active on both clones than the parent methyl ester 8b. Methyl glycocholate 12, with a stable RI of ca. 0.5, indicated the loss of activity in comparison to primary and n-propyl amides, 10 and 11, respectively. Based on this information, the influence of N-alkyl chain within the amides (8d→13–16, Table 2) on the spiro-2"-methylcyclohexane series was investigated. Again, the amides afforded higher activity than parent the ester 8d. Securing the C$_1$–C$_3$ chain within N-alkyl series, we prepared amides of (4"R)-methylspirocyclohexane (8 g→17–20), (4"S)-methylspirocyclohexane (8h→21–24), (4"R or S)-ethylspirocyclohexane (8i→25–28), and (4"S or R)-ethylspirocyclohexane (8j→29–32) series, Table 2. All 4"-substituted spirocyclohexyltetraoxane amides, 4"-methyl and 4"-ethyl, are significantly more active than corresponding methyl esters, except for the inactive n-propyl amides 24 and 32. The most active, primary amide 17 (IC$_{50}$ (D6)=0.74 ng/ml, IC$_{50}$ (W2)=0.37 ng/ml; Table 2), is ca. 9 times more active than parent methyl ester 8g.

In summary, the screening results given in the Tables clearly indicate that the substitution pattern at the spirocyclohexane ring is a very important structural element. Cyclohexanone itself afforded only one tetraoxane (8b), while prochiral 4-substituted cyclohexanones afforded respective epimeric pairs (8g, 8h; 8i, 8j; 8k, 8l).

Therefore, introducing the methyl to C(4") position greatly enhanced the activity against both *P. falciparum* clones, while doing so with the ethyl group did not provide improvement (Table 2). One feature merits special comment: remarkable difference is observed in activity of each epimeric pair possessing the same functionality at C(24) of the side chain (esters, acids, amides). In general, members of 4"R (and 4"(R or S)) series of all tetraoxanes are more active than respective epimers up to activity ratio of 30 (excluding 8k and 8l, which exhibited low activity on both D6 and W2 *P. falciparum* clones presumably due to the bulkiness of their t-butyl group, Table 2). See 16. Since subtle differences in conformation (and structure) in each of the diastereomers contribute to the activity of a compound, at present we cannot further elaborate on activity differences of 4"-methyl and 4"-ethyl tetraoxane series (e.g., simple MM calculation on 4"S-methyl compound, 9h, showed that all chair conformations of spirocyclohexane and dispirotetraoxacyclohexane rings fall within 1.1 kcal/mol, regardless of the orientation of the methyl group). The extensive QSAR calculations are underway in order to build a pharmacophore model.

Changing ester groups for amides enhanced the activity against both clones, and interesting results are obtained with primary amide 10, alkyl amides 11, 18–20, 26, and 23. All of them show effects similar to artemisinin (or better) against W2 *P. falciparum* clone, and the acid 9g and the primary amide 17 are among the compounds with highest known in vitro antimalarial activity on both, CQ-susceptible and CQ-resistant, *P. falciparum* strains.

The influence of the cholic acid carrier on the antimalarial activity is apparent: a) tetraoxane 8b is about 1.5 to about 1.8 times (primary amide 10 about 3 to about 6 times) more active than bis(1,1dioxycyclohexane); b) methyl epimer 8 g is about 2 to about 4 times (primary amide 17 about 20 to about 36 times) more active than bis(1,1-dioxy-4-methylcyclohexane); c) t-butyl epimer 8l is ca. about 3.7 times more active than bis(1,1-dioxy-4-tert-butylcyclohexane); d) 8d is ca. about 2 times (primary amide 13 ca. about 3.5 times) more active than bis(1,1-dioxy-2-methylcyclohexane); e) 8e is about 3 to about 30 times more active than bis(1,1-dioxy-2,6-dimethylcyclohexane). See McCullogh, K. J., et al. (2000) J. Med. Chem. 43:1246–1249; and Vennerstrom, J. L., et al. (2000) J. Med. Chem. 43:2753–2758, and references cited therein, which are herein incorporated by reference.

Therefore, the present invetion provides a method for preparing steroidal mixed tetraoxanes starting from parent ketones, via corresponding gem-dihydroperoxides, using simple reagents, mild reaction conditions, and short reaction time. Additionally, the present invention provides mixed tetraoxane compounds that are cholic acid-derived compounds which have improved solubility under physiological conditions and enhance the cell membrane permeability because of its amphiphilic character.

Additionally, the present invention also provides mixed tetraoxanes that exihit in vitro antimalarial activity that is significantly higher than that of prior art tetraoxanes, i.e. non-steroidal mixed tetraoxanes, bis-steroidal tetraoxanes and of simple cyclohexane-based tetraoxanes. See Jefford, C. W. et al. (2000) Heterocycles 52:1345–1352; Kim, H-S., et al. (2001) J. Med. Chem. 44:2357–2361; and Kim, H-S., et al. (1999) J. Chem. Soc., Perkin Trans 1:1867–1870, which are herein incorporated by reference. The present invention also provides mixed cholic acid-derived tetraoxanes having selective transformations of the carrier molecule that exhibit antimalarial activities that are more active in vitro than artemisinin and mefloquine, on chloroquine-resistant *P. falciparum* W2 clones. The present invention also provides a non-toxic primary amide 17 being ca. 6 times more active than artelinic acid, and 2.4 times as active as arteether (IC$_{50}$ (W2)=0.37 ng/ml; RI=0.50; SI=9 500). Therefore, the present invetion provides methods of treating, preventing, or inhibiting malaria which comprises administering the mixed tetraoxane compounds of the present invention.

Additionally, very encouraging results were obtained in tests on hemolytic activity of the mixed tetraoxane compounds of the present invention. Specifically, initial experiments using n-propyl amide 11 (1C20) as the test compound revealed no red blood cell (RBC) membrane lysis, thereby suggesting that antimalarial activity of the compounds of the present invention (primarily the amides) is the consequence of interaction specific to infected RBC, and is not the result of uncontrolled RBC membrane lysis. Therefore, the present invention provides methods of treating, preventing, or inhibiting malaria without inducing uncontrolled RBC membrane lysis which comprises administering the compounds of the present invention.

As provided in Examples 57 and 58 and Tables 3–4, the tetraoxanes of the present invention were found to exhibit antimycobaterial activity and cytotoxicity as well as in vitro antimalarial activity.

TABLE 3

In vitro Antimycobacterial Activity of (4"R)-methyl Derivatives against Mycobacterium tuberculosis strain H37Rv.

| Compound | Inhibition (%) | MIC[a] µg/ml | MIC[a] µM | Cytotoxicity (IC$_{50}$)[b] µg/ml | Cytotoxicity (IC$_{50}$)[b] µM |
|---|---|---|---|---|---|
| 8g (1B08a) | 29 | >6.25 | >9.63 | — | — |
| 9g (1C17) | 21 | >6.25 | >9.84 | — | — |
| 17 (1C26) | 99 | 3.13 | 4.94 | 3.49 | 5.51 |
| 18 (1C27) | 98 | 6.25 | 9.65 | 5.69 | 8.78 |
| 19 (1C28) | 98 | 3.13 | 4.73 | 5.37 | 8.11 |
| 20 (1C29) | 94 | 6.25 | 9.25 | 8.34 | 12.34 |
| 1B14a | 37 | >6.25 | — | — | — |
| 1B14b | 46 | >6.25 | — | — | — |
| 1C44 | 94 | 6.25 | — | — | — |
| 1C49 | 89 | >6.25 | — | — | — |
| 1C45 | 93 | 6.25 | — | — | — |
| 1C50 | 87 | 6.25 | — | — | — |
| 1C46 | 71 | 6.25 | — | — | — |
| 1C51 | 61 | >6.25 | — | — | — |
| 1C47 | 50 | >6.25 | — | — | — |
| 1C52 | 62 | >6.25 | — | — | — |
| 1C48 | 46 | >6.25 | — | — | — |
| 1C53 | 59 | >6.25 | — | — | — |
| Isoniazid c | — | 0.05 | 0.36 | >1000 | >7000 |
| Rifampin c | — | 0.12 | 0.15 | 110.67 | 134.48 |

[a]MIC = minimal inhibitory concentration.
[b]VERO cell line.
[c]Control drugs.

TABLE 4

In vitro Antiproliferative Activity of Tetraoxanes 1C44 and 1C45 (after 48 h, µM; selected data)

| Cell Line | Artemisinin (NSC 369397) | Comp. 1C44 | Comp. 1C45 | Paclitaxel (NSC 125973) |
|---|---|---|---|---|
| IGROV1[a] | | | | |
| GI50 | 79.4 | 0.26 | 0.295 | 0.032 |
| TGI | 100 | 0.82 | 1.11 | 79.4 |
| LC50 | 100 | 3.76 | — | 100 |
| TK-10[b] | | | | |
| GI50 | 100 | 1.99 | 2.70 | 0.25 |
| TGI | 100 | 5.94 | 4.66 | 50.1 |
| LC50 | 100 | 27.0 | 8.07 | 79.4 |
| UO-31[b] | | | | |
| GI50 | 79.4 | 1.83 | 0.36 | 1.58 |
| TGI | 100 | 3.51 | 1.35 | 39.8 |
| LC50 | 100 | 6.73 | 4.57 | 100 |
| SR[c] | | | | |
| GI50 | 100 | 1.83 | 0.29 | 0.079 |
| TGI | 100 | 5.92 | — | 63.1 |
| LC50 | 100 | 100 | 100 | 63.1 |
| KM-12[d] | | | | |
| GI50 | 100 | 1.96 | 1.19 | 0.0079 |
| TGI | 100 | 5.36 | 2.92 | 79.4 |
| LC50 | 100 | 40.1 | 7.15 | 100 |
| MALME-3M[e] | | | | |
| GI50 | 100 | 2.27 | 0.020 | 2.51 |
| TGI | 100 | 9.14 | 3.99 | 50.1 |
| LC50 | 100 | 47.0 | 37.3 | 79.4 |

[a]Ovarian cancer cell line
[b]Renal cancer cell line
[c]Leukemia cell line
[d]Colon cancer cell line
[e]Melanoma cancer cell line As shown in Table 3, the level of antimycobacterial activity of (4"R)-methyl series (17–20 (1C26–1C29)) is high, but the selectivity index (SI; IC$_{50}$ (Vero)/MIC (µg/ml)) for these compounds is rather low (1.7–0.9). However, when the cytotoxicity values (IC$_{50}$ (µM), Table 3) are compared to the antimalarial activity of the same tetraoxanes (1C26–1C29; Table 2) one obtains the excellent SI (IC$_{50}$ (Vero)/IC$_{50}$ (D6 or W2)), with the lowest value being 1400.

In preliminary tests, four compounds (1B14a, 1C44, 1C45, and 1C46) were chosen by NIH-NCI for in vitro screening. See Drug discovery and development program, National Cancer Institute, Bethesda, (NCI), http://dtp.nci.nih.gov. All tetraoxanes were evaluated in the 3-cell line (lung—NCI-H460, breast—MCF7, CNS-SF-268) one dose primary anticancer assay: growth percentage after 48 hours, at 100 µM concentration of tested compound. Two compounds were eliminated at this step (1B14a and 1C46), while the acid 1C44 and primary amide 1C45 were evaluated against the full panel of 60 human tumor cell lines starting with $10^{-4}$ M concentration of investigated compounds. The assessed antiproliferative activity, expressed as GI$_{50}$, TGI, LC$_{50}$ were obtained applying a 48 hour continuous drug exposure protocol using SRB (sulforhodamine B) protein assay.

The results, given in Table 4, indicate that both compounds are strong antiproliferatives with 50% growth inhibitory activities (GI$_{50}$) often on nanomolar scale. The highest activity exerted the primary amide IC45 on a melanoma cancer cell line (MALME-3M; GI$_{50}$=20 nM). The compounds arrested the cancer cells growth (TGI) at the concentration within ca. 0.8–9.14 µM range, with the acid IC44 being good inhibitor of ovarian cancer cell line growth (IGROV1; TGI=0.82 µM). The LC$_{50}$ values (concentration of the compound at which 50% of the cells are killed) for both compounds are mostly at $10^{-6}$ M level indicating, together with previous results, indicate that the mixed tetraoxanes of the present invention may be used to treat, prevent, or inhibit disorders and diseases associated with cell proliferation such as cancer. Tests of further compounds are provided in Example 58.

Therefore, the present invention provides tetraoxanes that exhibit antibacterial and antiproliferative activity. Thus, the present invention provides methods of treating, preventing, or inhibiting diseases and disorders associated with bacterial infections and cell proliferation which comprises administering the mixed tetraoxane compounds of the present invention.

Diseases and disorders associated with bacterial infection include those caused by an organism belonging to *Mycobacterium*, preferably *Mycobacterium tuberculosis*. Diseases and disorders related to cell proliferation include cancer, papillomas, acute and chronic inflammation, rheumatoid arthritis, psoriasis, atherosclerosis, diabetic retinopathy, chronic obstructive pulmonary disorder, tuberculosis, chronic cholecystitis, osteoarthritis, rheumatic carditis, bronchiectasis, Hashimoto's thyroiditis, inflammatory bowel diseases such as ulcerative colitis and Crohn's disease, silicosis, and the like. In preferred embodiments, the disease is cancer, such as leukemia, CNS cancer, renal cancer, non-small cell lung cancer, melanoma, prostate cancer, colon cancer, ovarian cancer, or breast cancer.

In accordance with a convention used in the art, ⌇ is used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

An "alkyl" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (n-Bu), isobutyl (i-Bu), t-butyl (t-Bu), (sec-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl" is intended to mean a non-aromatic monovalent monocyclic, bicyclic, or tricyclic radical comprising 3–14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

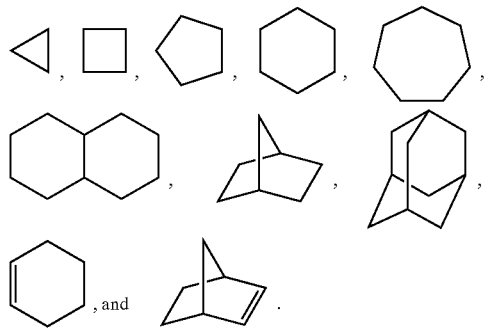

A "heterocycloalkyl" is intended to mean a non-aromatic monovalent monocyclic, bicyclic, or tricyclic radical, which is saturated or unsaturated, comprising 3–18 ring members, which includes 1–5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

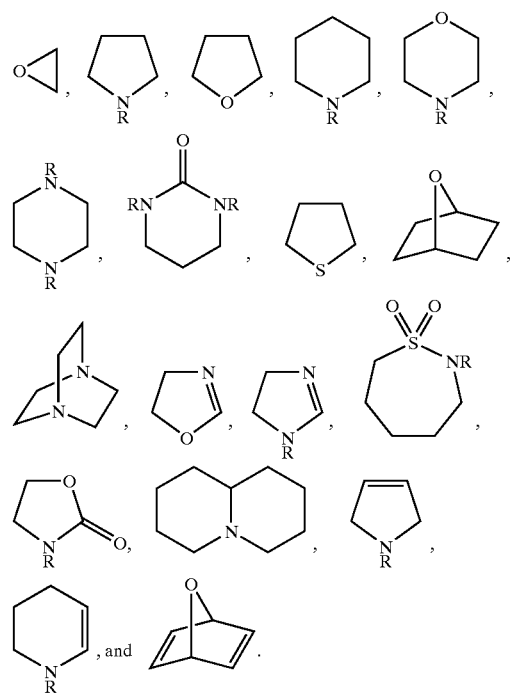

An "aryl" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

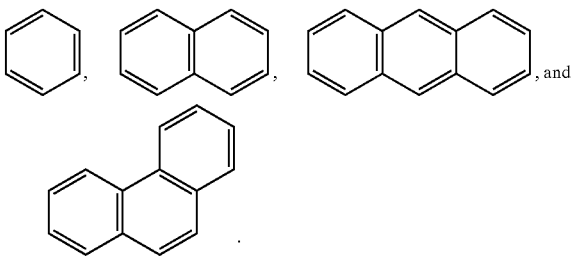

A "heteroaryl" is intended to mean an aromatic monovalent monocyclic, bicyclic, or tricyclic radical comprising 4–18 ring members, including 1–5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl" is intended to mean a —C(O)—$R^a$ radical, where $R^a$ is a suitable substituent as defined below.

A "thioacyl" is intended to mean a —C(S)—$R^a$ radical, where $R^a$ is a suitable substituent as defined below.

A "sulfonyl" is intended to mean a —$SO_2R^a$ radical, where $R^a$ is a suitable substituent as defined below.

A "hydroxyl" is intended to mean the radical —OH.

An "amino" is intended to mean the radical —$NH_2$.

An "alkylamino" is intended to mean the radical —$NHR^a$, where $R^a$ is an alkyl group.

A "dialkylamino" is intended to mean the radical —$NR^aR^b$, where $R^a$ and $R^b$ are each independently an alkyl group.

An "alkoxyl" is intended to mean the radical —$OR^a$, where $R^a$ is an alkyl group. Exemplary alkoxyl groups include methoxyl, ethoxyl, propoxyl, and the like.

An "alkoxycarbonyl" is intended to mean the radical —C(O)$OR^a$, where $R^a$ is an alkyl group.

An "alkylsulfonyl" is intended to mean the radical —$SO_2R^a$, where $R^a$ is an alkyl group.

An "alkylaminocarbonyl" is intended to mean the radical —C(O)$NHR^a$, where $R^a$ is an alkyl group.

A "dialkylaminocarbonyl" is intended to mean the radical —C(O)$NR^aR^b$, where $R^a$ and $R^b$ are each independently an alkyl group.

A "mercapto" is intended to mean the radical —SH.

An "alkylthio" is intended to mean the radical —$SR^a$, where $R^a$ is an alkyl group.

A "carboxyl" is intended to mean the radical —C(O)OH.

A "carbamoyl group" is intended to mean the radical —C(O)$NH_2$.

An "aryloxyl" is intended to mean the radical —$OR^c$, where $R^c$ is an aryl group.

A "heteroaryloxyl" is intended to mean the radical —$OR^d$, where $R^d$ is a heteroaryl group.

An "arylthio" is intended to mean the radical —$SR^c$, where $R^c$ is an aryl group.

A "heteroarylthio" is intended to mean the radical —$SR^d$, where $R^d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wuts, Protective Groups in Organic Synthesis, $3^{rd}$ edition, John Wiley and Sons, New York, N.Y. (1999).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; C-6 alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl; aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted)unless indicated otherwise herein (e.g., by indicating that the specified group is unsubstituted).

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the compounds of the present invention may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the compounds of the present invention, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of the compounds of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding. See, for example, Lee et al., (1984) Biochem. 23:4255. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin) or peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011–2016; Shan, D. et al., *J. Pharm. Sci.,* 86(7):765–767; Bagshawe K., (1995) Drug Dev. Res. 34:220–230; Bodor, N., (1984) Advances in Drug Res. 13:224–331; Bundgaard, H., *Design of Prodrugs* (Elsevier Press, 1985); and Larsen, I. K., *Design and Application of Prodrugs*, Drug Design and Development (Krogsgaard-Larsen et al., eds., Harwood Academic Publishers, 1991).

If the compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the present invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the compound of the present invention and salts may exist in different crystal or polymorphic forms, all of which are intended to be within the scope of the present invention and specified structural formulas.

The compounds of the present invention in accordance with the present invention are useful in the treatment malaria and diseases and disorders associated with cell proliferation such as cancer, papillomas, acute and chronic inflammation, rheumatoid arthritis, psoriasis, atherosclerosis, diabetic retinopathy, chronic obstructive pulmonary disorder, tuberculosis, chronic cholecystitis, osteoarthritis, rheumatic carditis, bronchiectasis, Hashimoto's thyroiditis, inflammatory bowel diseases such as ulcerative colitis and Crohn's disease, silicosis, and the like.

The antimalarial or antiproliferative activity of the compounds of the present invention may be measured by any of the methods available to those skilled in the art, including in vitro and in vivo assays. Examples of suitable assays for activity measurements are provided herein. Properties of the compounds of the present invention may be assessed, for example, by using one or more of the assays set out in the Examples below. Other pharmacological methods may also be used to determine the efficacy of the compounds as antimalarial and antiproliferative agents.

The compounds of the present invention may be used in combination with or as a substitution for treatments of the above conditions. For example, the compounds of the present invention may also be used alone or combination with antimalarial agents known in the art. The compounds of the present invention may be used alone or in combination with antiproliferative agents such as steroids, which include prednisolone (corticosteroid), antibiotics such as penicillin and streptomycin, anticancer agents such as cisplatin, hydroxyurea, and pacitaxel, and the like. Further, the compounds of the present invention may be used alone or in combination with analgesics to treat, prevent or inhibit pain.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

A compound of the present invention may be administered in a therapeutically effective amount to a mammal such as a human. Therapeutically effective amounts of the compounds of the present invention may be used to treat, modulate, attenuate, reverse, or affect a cell proliferation or a bacterial infection or a protozoal infection in a mammal. An "effective amount" is intended to mean that amount of an agent that is sufficient to treat, prevent, or inhibit a disease or disorder associated with cell proliferation or a bacterial infection or a protozoal infection. In some preferred embodiments, the protozoal infection is caused by a *Plasmodium* parasite, preferably, *P. falciparum, P. vivax, P. ovale,* or *P. malariae*. In some preferred embodiments, the bacterial infection is caused by an organism belonging to *Mycobacterium*, preferably *Mycobacterium tuberculosis*.

Diseases and disorders related to cell proliferation include cancer, papillomas, acute and chronic inflammation, rheumatoid arthritis, psoriasis, atherosclerosis, diabetic retinopathy, chronic obstructive pulmonary disorder, tuberculosis, chronic cholecystitis, osteoarthritis, rheumatic carditis, bronchiectasis, Hashimoto's thyroiditis, inflammatory bowel diseases such as ulcerative colitis and Crohn's disease, silicosis, and the like. In preferred embodiments, the cancer is leukemia, CNS cancer, renal cancer, non-small cell lung cancer, melanoma, prostate cancer, colon cancer, ovarian cancer, or breast cancer.

Thus, e.g., a "therapeutically effective amount" of a compound of the present invention, a prodrug, an active metabolite, or a salt thereof, is a quantity sufficient to, when administered to a mammal, treat, prevent, or inhibit malaria or cell proliferation. The amount of a given compound of the present invention that will correspond to such an amount will vary depending upon factors such as the given drug or compound, the pharmaceutical formulation and route of administration, the type of inflammatory disease or disorder, the type of inflammation, and the identity of the subject or host being treated, but can nevertheless be routinely determined by one skilled in the art. Also, as used herein, a "therapeutically effective amount" of a compound of the present invention is an amount which prevents, inhibits, suppresses, or reduces malaria (as determined by clinical symptoms or the amount of *Plasmodium* organisms) in a subject as compared to a control. As defined herein, a therapeutically effective amount of a compound of the present invention may be readily determined by one of ordinary skill by routine methods known in the art.

For example, a therapeutically effective amount of a compound of the invention ranges from about 0.1 to about 1,000 mg/kg body weight, preferably about 0.1 to about 500 mg/kg body weight, and more preferably about 0.1 to about 100 mg/kg body weight. The skilled artisan will appreciate that certain factors may influence the dosage required to effectively treat a subject, including but not limited to the severity of the disease or disorder, previous treatments, the general health and/or age of the subject, and other diseases present.

Preferred topical concentrations include about 0.1% to about 10% of at least one compound of the present invention in a formulated salve. The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of the compound of the present invention may consist of a single administration, or alternatively comprise a series of applications. For example, a subject may be treated with a compound of the present invention at least once. However, the subject may treated with the compound from about one time per week to about once daily for a given treatment period. The length of the treatment period will depend on a variety of factors such as the severity of inflammation, the concentration and activity of the compounds of the present invention, or a combination thereof. It will also be appreciated that the effective dosage of the compound used for treatment may increase or decrease over the course of a particular treatment. Changes in dosage may result and become apparent by standard diagnostic assays known in the art. In some instances chronic administration may be required. The compounds of the present invention may be administered before, during, after, or a combination thereof exposure to malaria or an agent that induces cell proliferation.

The pharmaceutical formulations of the invention comprise at least one compound of the present invention and may be prepared in a unit-dosage form appropriate for the desired mode of administration. The pharmaceutical formulations of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen compound of the present invention.

It will be appreciated that the actual dosages of the compounds used in the pharmaceutical formulations of this invention will vary according to the particular complex being used, the particular composition formulated, the mode of administration, and the particular site, host, and disease being treated. Optimal dosages for a given set of conditions may be ascertained by those skilled in the art using conventional dosage determination tests in view of the experimental data for a given compound. Administration of prodrugs may be dosed at weight levels that are chemically equivalent to the weight levels of the fully active forms.

The compounds of the present invention can be incorporated into pharmaceutical formulations suitable for administration. Pharmaceutical formulations of this invention comprise a therapeutically effective amount of at least one compound of the present invention, and an inert, pharmaceutically or cosmetically acceptable carrier or diluent. As used herein the language "pharmaceutically or cosmetically acceptable carrier" is intended to include any and all solvents, dispersion media, coatings, antibacterial and antifungal agents, isotonic and absorption delaying agents, and the like, compatible with pharmaceutical or cosmetic administration. The pharmaceutical or cosmetic carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically or cosmetically active substances is well known in the art.

Except insofar as any conventional media or agent is incompatible with the active compound, use thereof in the formulation is contemplated. Supplementary active compounds can also be incorporated into the formulations. Supplementary active compounds include antimalarials, antiproliferative agents, antibacterials, antiprotozoal agents, and antifungal agents and other compounds commonly used to treat diseases and disorders related to cell proliferation and bacterial, protozoal, and fungal infections. Supplementary active compounds include:

Antibiotics such as penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, colistin, polymyxin B, sulfonamide, trimethoprim-sulfamethoxazole, co-amoxyclav, cephalothin, cefuroxime, ceftriaxone, vancomycin, gentamicin, amikacin, metronidazole, chloramphenicol, nitrofurantoin, co-trimoxazole, rifampicin, isoniazid, pyrazinamide, and the like;

Antiprotozoal agents include chloroquine, doxycycline, mefloquine, metronidazole, eplornithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprim-sulfamethoxazole, pyrimethamine, sulfadiazine, and the like;

Antifungal agents include amphotericin B, fluconazole, itraconazole, ketoconazole, potassium iodide, flucytosine, and the like; and Antiproliferative agents such as altretamine, amifostine, anastrozole, arsenic trioxide, bexarotene, bleomycin, busulfan, capecitabine, carboplatin, carmustine, celecoxib, chlorambucil, cisplatin, cisplatin-epinephrine gel, cladribine, cytarabine liposomal, daunorubicin liposomal, daunorubicin daunomycin, dexrazoxane, docetaxel, doxorubicin, doxorubicin liposomal, epirubicin, estramustine, etoposide phosphate, etoposide VP-16, exemestane, fludarabine, fluorouracil 5-FU, fulvestrant, gemicitabine, gemtuzumab-ozogamicin, goserelin acetate, hydroxyurea, idarubicin, ifosfamide, imatinib mesylate, irinotecan, letrozole, leucovorin, levamisole, liposomal daunorubicin, melphalan L-PAM, mesna, methotrexate, methoxsalen, mitomycin C, mitoxantrone, paclitaxel, pamidronate, pegademase, pentostain, porfimer sodium, streptozocin, talc, tamoxifen, temozolamide, teniposide VM-26, topotecan, toremifene, tretinoin, ATRA, valrubicin, vinorelbine, zoledronate, and the like.

A pharmaceutical or cosmetic formulation of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from 0–60% of the total volume.

The pharmaceutical formulation may also be in the form of a solution of a salt form of the active ingredient in an appropriate aqueous vehicle such as water or isotonic saline or dextrose solution.

The pharmaceutical formulations of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical formulations may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds of the present invention can be formulated readily by combining with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (compound), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum horoi, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds and agents.

Pharmaceutical formulations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the formulations may take the form of tablets or lozenges formulated in conventional manner.

Oral formulations generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral formulations can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the compounds of the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of the compound and a suitable powder base such as lactose or starch.

The compounds of the present invention may be formulated for parenteral administration by injection, e.g., by bolus injection or continuous infusion. Formulations for injection may be presented in unit-dosage form, e.g., in ampoules or in multi-dose containers, with an added preservative. The formulations may take such forms as suspensions, solutions or emulsions in oily or aqueous vehicles, and may comprise formulatory agents such as suspending, stabilizing and/or dispersing agents.

Pharmaceutical formulations suitable for injectable use include sterile aqueous solutions (where water soluble) or dispersions and sterile powders for the extemporaneous preparation of sterile injectable solutions or dispersion. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the compounds to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid horoidsene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the formulation. Prolonged absorption of the injectable compositions can be brought about by including in the formulation an agent which delays absorption, for example, aluminum monostearate and gelatin.

Sterile injectable solutions can be prepared by incorporating a therapeutically effective amount of at least one compound of the present invention in an appropriate solvent with one or a combination of ingredients enumerated above, as required, followed by filtered sterilization. Generally, dispersions are prepared by incorporating the compound of the present invention into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

For example, for topical formulations, pharmaceutically acceptable excipients or cosmetically acceptable carriers and additives include solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art.

For administration to the eye, the compounds of the present invention of the present invention may delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, horoids/retina and selera. The pharmaceutically acceptable ophthalmic vehicle may be an ointment, vegetable oil, or an encapsulating material. Compounds of the present invention may also be injected directly into the vitreous and aqueous humor.

Alternatively, compounds of the present invention may be in powder form for constitution with a suitable vehicle, e.g., sterile pyrogen-free water, before use. The compounds of the present invention may also be formulated in rectal compositions such as suppositories or retention enemas, e.g., comprising conventional suppository bases such as cocoa butter or other glycerides.

In addition to the formulations described above, compounds of the present invention may also be formulated as a depot preparation. Such long-acting formulations may be administered by implantation (for example, subcutaneously or intramuscularly) or by intramuscular injection. Thus, for example, the compounds of the present invention may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied, for example: other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical formulations may be employed. Liposomes and emulsions are known examples of delivery vehicles or carriers for hydrophobic drugs and cosmetics. Certain organic solvents such as dimethylsulfoxide also may be employed, although usually at the cost of greater toxicity. Additionally, the compounds may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical formulations also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, and the like. Salts tend to be more soluble in aqueous or other protonic solvents than are the corresponding free-base forms.

In one embodiment, the compounds of the present invention are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically or cosmetically acceptable carriers. These can be prepared according to methods known to those skilled in the art, for example, as described in U.S. Pat. No. 4,522,811.

It is especially advantageous to formulate oral or parenteral formulations in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The following Examples are intended to illustrate but not to limit the invention. In the following Examples, the compounds having the structural formulas in the above-referenced Schemes are referenced.

A. SYNTHESIS OF GEM-DIHYDROPEROXIDES

EXAMPLE 1

Methyl 3,3-Dihydroperoxy-7α,12α-diacetoxy-5β-cholan-24-oate (2A01; compound 2, wherein R is ethanoyl, X is methoxy)

Ketone 5, wherein R is ethanoyl and X is methoxy, (3.00 g, 5.94 mmol), was dissolved at r.t. in a $CH_3CN/CH_2Cl_2$ mixture (120 ml, 3:1 v/v) followed by 30% $H_2O_2$ (6.18 ml, 60.6 mmol) and five drops of conc. HCl. The reaction mixture was stirred for 2 hours at 22° C., quenched with water (80 ml), $CH_2Cl_2$ (120 ml) was added and separated organic layer was worked-up using sat. $NaHCO_3$ solution (2×10 ml) and brine (3×20 ml). After drying the organic extract over anh. $Na_2SO_4$ and filtering, crude methyl 3,3-dihydroperoxy-7α,12α-diacetoxy-5β-cholan-24-oate (3.20 g (97%); colorless solid), 2A01, was obtained.

An analytical sample of 2A01 was obtained after $SiO_2$ purification (Lobar B $SiO_2$ column, Merck, r.t., eluent: heptane/EtOAc (1:1)) and crystallization from ether using conventional methods known in the art.

Mp=197–199° C. (colorless prisms, ether). IR (KBr): 3429, 2954, 1736, 1636, 1439, 1382, 1254, 1124, 1077 $cm^{-1}$. IR ($CCl_4$): 3442, 2952, 1736, 1636, 1559, 1541, 1508, 1439, 1381, 1253, 1127, 1103, 1077 $cm^{-1}$. $^1$H NMR (200 MHz, $CDCl_3$): 9.06 (bs, 2H, HOO—C(3), exchangeable with $D_2O$), 5.08 (bs, H—C(12)), 4.90 (bs, H—C(7)), 3.67 (s, $CH_3O_2C(24)$)), 2.16 (s, $CH_3COO$—), 2.13 (s, $CH_3COO$—), 0.95 (s, $H_3C$—C(10)), 0.08 (d, J=6.0 Hz, $H_3C$—C(20)), 0.73 (s, $H_3C$—C(13)). $^{13}$C NMR (50 MHz, $CDCl_3$): 175.06, 171.22, 110.65, 75.62, 71.10, 51.66, 47.32, 45.07, 43.30, 38.29, 37.62, 34.58, 32.16, 30.90, 30.66, 28.57, 27.10, 25.69, 24.31, 22.73, 22.12, 21.63, 21.50, 17.43, 12.17. Positive ESI-MS (m/z): 1031.63 ($[2M+Na]^+$, 15), 577.32 ($[M+Na]^+$, 4), 572.36 (4), 559.29 (4), 543.28 ($[M+Na—H_2O_2]^+$, 19), 527.30 ($[M+Na—H_2O_2—H_2O]^+$, 100), 522.36 (33), 385.28 (75). Positive high resolution ESI exact mass measurement: m/z 577.3077 corresponding to a molecular formula $C_{29}H_{46}O_{10}Na$ (error in ppm: 15). Anal. ($C_{29}H_{46}O_{10}$) C, H.

According to the above given experimental conditions, the following gem-dihydroperoxides can be prepared according to the above-referenced Schemes using conventional methods known in the art:

EXAMPLE 2

3,3-Dihydroperoxy-7α,12α-diacetoxy-5β-cholan-24-amide (2A02; compound 2, wherein R is primary amino)

IR (KBr): 3447, 2952, 2882, 1729, 1664, 1615, 1448, 1383, 1255, 1125, 1082, 1028, 964 $cm^{-1}$. $^1$H NMR (200 MHz, $CDCl_3$): 6.02 (bs, $H_2N$—C(24), exchangeable with $D_2O$), 5.91 (bs, $H_2N$—C(24), exchangeable with $D_2O$), 5.09 (bs, H—C(12)), 4.89 (bs, H—C(7)), 2.14 (bs, $CH_3COO$—), 2.09 (bs, $CH_3COO$—), 0.95 (s, $H_3C$—C(10)), 0.79 (d, J=6.0 Hz, $H_3C$—C(20)), 0.73 (s, $H_3C$—C(13)). $^{13}$C NMR (50 MHz, $CDCl_3$): 177.05, 170.92, 170.83, 170.64, 110.05, 70.86, 70.58, 53.34, 47.32, 44.99, 43.22, 43.12, 42.02, 38.19, 37.56, 36.48, 34.59, 34.49, 34.27, 32.52, 32.11, 31.23, 30.60, 29.71, 28.47, 27.02, 25.62, 24.28, 22.65, 22.02, 21.45, 21.33, 21.19, 17.40, 12.08

EXAMPLE 3

N-(n-Propyl)-3,3-dihydroperoxy-7α,12α-diacetoxy-5β-cholan-24-amide (2A03; compound 2, wherein R is ethanoyl, X is N-(n-propyl)amino)

Mp 120–129° C. (colorless powder, ether). IR (KBr): 3377, 2957, 2882, 1739, 1637, 1556, 1448, 1382, 1255, 1131, 1082, 1028, 964 $cm^{-1}$. $^1$H NMR (200 MHz, $CDCl_3$): 10.56, 10.51 (both s, 2H, HOO—C(3), exchangeable with $D_2O$), 5.90–5.70 (m, HN—C(24)) 5.08 (bs, H—C(12)), 4.89 (bs, H—C(7)), 3.30–3.10 (m, $CH_3CH_2CH_2$—NH—), 2.14 (bs, $CH_3COO$—), 2.09 (bs, $CH_3COO$—), 1.70–1.30 (m, $CH_3CH_2CH_2$—NH—), 1.00–0.8 (m, $H_3C$—C(10) and $CH_3CH_2CH_2$—NH—)), 0.80 (d, J=5.4 Hz, $H_3C$—C(20)), 0.72 (s, $H_3C$—C(13)). $^{13}$C NMR (50 MHz, $CDCl_3$): 175.30, 170.92, 170.78, 110.08, 75.38, 70.81, 47.37, 45;04, 43.30, 41.65, 38.25, 37.60, 34.74, 34.60, 33.65, 32.20, 31.44, 30.69, 28.54, 27.11, 25.74, 24.43, 22.72, 22.49, 22.10, 21.65, 21.55, 17.49, 12.19, 11.25. ESI-MS (m/z, (%)): 620.29 ($[M+K]^+$, 6), 604.32 ($[M+Na]^+$, 56), 582.33 ($[M+H]^+$, 38), 554.32 (22), 522.31 (9), 428.30 (31), 410.29 (16), 385.24 (100), 284.32 (34), 233.62 (6).Anal. ($C_{31}H_{51}NO_9$) C,H.

EXAMPLE 4

1,1-Dihydroperoxy-4-methylcyclohexane (4A04; compound 4, wherein R4 is methyl)

IR (film): 3420, 2935, 2865, 1712, 1637, 1554, 1378, 1357, 1265, 1200, 1158, 1104, 1050, 1017, 980, 910, 861 $cm^{-1}$. IR ($CCl_4$): 3431, 2957, 2930, 2865, 1712, 1551, 1454, 1384, 1357, 1255, 1222, 1162, 1103, 1071, 1012, 980 $cm^{-1}$. $^1$H NMR (200 MHz, $CDCl_3$): 9.26 (bs, 2H, HOO—C(1)), 2.30–2.00 (m), 1.70–1.30 (m), 1.30–1.10 (m), 0.93 (d, J=6.2 Hz, $H_3C$—C(4)). $^{13}$C NMR (50 MHz, $CDCl_3$): 110.73, 40.83, 31.59, 30.58, 29.03, 21.38.

B. PREPARATION OF STEROIDAL MIXED TETRAOXANES

The steroidal mixed tetraoxanes of the structural formula 1 may be prepared according to the above-referenced Schemes using conventional methods known in the art. Specifically, the steroidal mixed tetraoxanes of the structural formula 1, wherein R is ethanoyl and X is methoxy, can be prepared starting from gem-dihydroperoxide of the structural formula 2, wherein R is ethanoyl and X is methoxy, and cycloalkanone of the structural formula 3, wherein the substituents have the significance described above, as methyl esters, and in a preferred embodiment, subsequently transformed into acids and amide derivatives thereof. Some amide tetraoxane derivatives can be prepared directly from gem-dihydroperoxides of the structural formula 2, wherein R is ethanoyl and X is selected amine moiety, and cycloalkanone of the structural formula 3, wherein the substituents have the significance described above. Alternatively, steroidal mixed tetraoxanes of the structural formula 1, wherein R is ethanoyl and X is alkoxy, can be prepared from gem-dihydroperoxides of the structural formula 4 wherein n is 0, 1 and 3;

R1 is H or alkyl wherein alkyl is methyl, ethyl, or isopropyl;

R2 is H, methyl, or ethyl;

R3 is H, methyl, or ethyl;

R4 is H, methyl, ethyl, phenyl, p-hydroxyphenyl, p-methoxyphenyl, p-nitrophenyl;

wherein Y is all $C_1$–$C_4$ straight or branched-chain alkoxy, or

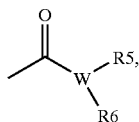

wherein W is N, R5 is hydrogen; methyl, ethyl, n-propyl, isopropyl, or methyl ethanoate 2-yl, and R6 is hydrogen; methyl, ethyl, or n-propyl, or R5 and R6 are part of a pyrrolidine or piperidine ring; and ketone 5
wherein
R is H; ethanoyl, propanoyl, or benzoyl;
X is a $C_1$–$C_4$ straight or branched-chain alkoxy, a primary amino, a N-alkylamino wherein the alkyl denotes all straight-chain alkyl groups containing from 1 to 4 carbon atoms, methyl ethanoate-2-yl, or a N-arylamino wherein the aryl is phenyl, p-nitrophenyl, N,N-dimethylamino, N,N-diethylamino, N,N-di(n-propyl)amino, N-pyrrolidino, or N-piperidino.

EXAMPLE 5

Methyl 7α,12α-Diacetoxy-5β-cholan-24-oate-3-spiro-6'-(1',2',4',5'-tetraoxacyclohexane)-3'-spirocyclopentane (1B04)

To the solution of dihydroperoxide 2A01 (500 mg, 0.90 mmol) in $CH_2Cl_2$ (14 ml) cyclopentanone (1.80 mmol) was added at r.t., and the reaction mixture was cooled with stirring to 0° C. in an ice-bath. After 30 min, 599 μl of ice-bath cooled ($H_2SO_4$: $CH_3CN$)-mixture (1:10, v/v) was added dropwise. The reaction mixture was stirred at 0° C. for 15 min, and after work-up as given for 2A01, the crude product was purified by $SiO_2$ column chromatography as above (eluent heptane/EtOAc (85:15)) to afford tetraoxane 1B04.

Yield 146 mg (26%). Mp=180–182° C. (colorless prisms, ether-hexane). $[\alpha]_D^{20}$=+49.56 (c=1.02, $CHCl_3$). IR (KBr): 2954, 2875, 1736, 1440, 1379, 1242, 1076, 1032 cm$^{-1}$. $^1$H NMR (200 MHz, $CDCl_3$): 5.09 (bs, H—C(12)), 4.92 (bs, H—C(7)), 3.66 (s, $CH_3O_2C(24)$), 2.13 (s, $CH_3COO$—), 2.08 (s, $CH_3COO$—), 0.94 (s, $H_3C$—C(10)), 0.81 (d, J=6.0 Hz, $H_3C$—C(20)), 0.73 (s, $H_3C$—C(13)). $^{13}$C NMR (50 MHz, $CDCl_3$): 174.42, 170.49, 119.71, 108.35, 75.12, 70.52, 53.35, 51.38, 47.14, 44.88, 43.17, 37.47, 35.12, 34.52, 34.42, 34.18, 32.08, 30.66, 30.56, 28.28, 26.28, 25.57, 24.88, 24.40, 24.15, 23.75, 22.62, 21.98, 21.45, 21.29, 17.32, 12.06. Positive ESI-MS (m/z): 1263.75 ([2M+Na]$^+$, 25), 659.35 ([M+K]$^+$, 18), 643.37 ([M+Na]$^+$, 100), 638.41 ([M+NH$_4$]$^+$, 41). Positive high resolution ESI exact mass measurement: m/z 643.3467 corresponding to a molecular formula $C_{34}H_{52}O_{10}Na$ (error in ppm: 1.3). Anal. ($C_{34}H_{52}O_{10}$) C, H.

According to the above given experimental conditions, the following steroidal mixed tetraoxanes were prepared according to the above-referenced Schemes using conventional methods known in the art:

EXAMPLE 6

Methyl 7α,12α-Diacetoxy-5β-cholan-24-oate-3-spiro-6'-(1',2',4',5'-tetraoxacyclohexane)-3'-spirocyclohexane (1B05)

Yield 177 mg (31%). Mp=165–168° C. (colorless prisms, ether-hexane). $[\alpha]_D^{20}$=+44.93 (c=1.06, $CHCl_3$). IR (KBr): 2947, 2868, 1741, 1451, 1378, 1250, 1238, 1227, 1181, 1076, 1036 cm$^{-1}$. $^1$H NMR (200 MHz, $CDCl_3$): 5.09 (bs, H—C(12)), 4.92 (bs, H—C(7)), 3.66 (s, $CH_3O_2C(24)$), 2.12 (s, $CH_3COO$—), 2.08 (s, $CH_3COO$—), 0.94 (s, $H_3C$—C(10)), 0.81 (d, J=6.0 Hz, $H_3C$—C(20)), 0.73 (s, $H_3C$—C(13)). $^{13}$C NMR (50 MHz, $CDCl_3$): 174.48, 170.51, 108.41, 108.28, 75.18, 70.59, 51.42, 47.21, 44.94, 43.23, 37.56, 34.58, 34.47, 30.74, 30.63, 28.33, 27.04, 25.60, 25.24, 22.67, 22.00, 21.52, 21.31, 17.37, 12.11. Positive ESI-MS (m/z): 1263.76 ([2M+Na]$^+$, 20), 659.35 ([M+K]$^+$, 40), 643.37 ([M+Na]$^+$, 100), 638.40 ([M+NH$_4$]$^+$, 45). Anal. ($C_{35}H_{54}O_{10}$) C, H.

EXAMPLE 7

Methyl 7α,12α-Diacetoxy-5β-cholan-24-oate-3-spiro-6'-(1',2',4',5'-tetraoxacyclohexane)-3'-spiro-1"-(2"-methyl)cyclohexane (1B06)

Yield 246 mg (38%). Mp=204–207° C. (colorless prisms, ether). $[\alpha]_D^{20}$=+35.80 (c=1.00, $CHCl_3$). IR (KBr): 3456, 2937, 1734, 1379, 1251, 1243, 1225, 1077, 1030 cm$^{-1}$. $^1$H-NMR (200 MHz, $CDCl_3$): 5.09 (bs, H—C(12)), 4.92 (bs, H—C(7)), 3.66 (s, $CH_3O_2C(24)$), 2.143 (s, $CH_3COO$—), 2.136 (s, $CH_3COO$—), 2.11 (s, $CH_3COO$—), 2.10 (s, $CH_3COO$—), 2.07 (s, $CH_3COO$—), 1.00 (d, J=6.6 Hz, $H_3C$—C(2")), 0.94 (s, $H_3C$—C(10)), 0.81 (d, J=6.0 Hz, $H_3C$—C(20)), 0.73 (s, $H_3C$—C(13)). $^{13}$C-NMR (50 MHz, $CDCl_3$): 174.50, 170.61, 170.53, 170.32, 109.42, 108.38, 108.34, 75.25, 70.63, 51.45, 47.26, 44.99, 43.25, 37.59, 34.52, 32.10, 30.78, 30.68, 28.34, 27.07, 25.63, 24.46, 22.71, 22.02, 21.51, 21.38, 17.41, 13.54, 12.13. Positive high resolution ESI exact mass measurement: m/z 671.3761 corresponding to a molecular formula $C_{36}H_{56}O_{10}Na$ (error in ppm: 1.5). Anal. ($C_{36}H_{56}O_{10}$) C, H.

EXAMPLE 8

Methyl 7α,12α-diacetoxy-5β-cholan-24-oate-3-spiro-6'-(1',2',4',5'-tetraoxacyclohexane)-3'-spiro-1"-(2",6"-dimethyl)cyclohexane (1B07)

Yield 149 mg (25%). Mp=213–215° C. (colorless prisms, ether). IR (KBr): 2940, 2876, 1732, 1452, 1379, 1244, 1225, 1095, 1076, 1032 cm$^{-1}$. $^1$H NMR (200 MHz, $CDCl_3$): 5.09 (bs, H—C(12)), 4.91 (bs, H—C(7)), 3.66 (s, $CH_3O_2C(24)$), 2.13 (s, $CH_3COO$—), 2.08 (s, $CH_3COO$—), 0.99 (d, J=6.2 Hz, $H_3C$—C(2"), $H_3C$—C(6")), 0.95 (s, $H_3C$—C(10)), 0.81 (d, J=6.0 Hz, $H_3C$—C(20)), 0.73 (s, $H_3C$—C(13)). $^{13}$C NMR (50 MHz, $CDCl_3$): 174.40, 170.51, 111.23, 108.17, 75.18, 70.54, 51.38, 47.16, 44.90, 43.17, 37.51, 34.49, 34.43, 30.68, 30.59, 27.00, 25.55, 22.64, 21.91, 21.41, 21.42, 21.31, 19.48, 17.34, 13.60, 12.06. Positive ESI-MS (m/z): 1347.80 ([2M+Na]$^+$, 32), 701.37 ([M+K]$^+$, 27), 685.38 ([M+Na]$^+$, 100), 680.44 ([M+NH$_4$]$^+$, 36). Anal. ($C_{37}H_{58}O_{10}$) C, H.

EXAMPLE 9

Methyl 7α,12α-diacetoxy-5β-cholan-24-oate-3-spiro-6'-(1',2',4',5'-tetraoxacyclohexane)-3'-spiro-1"-((4"R)- and (4"S)-methyl)cyclohexane (1B08a and 1B08b)

As an exception of all other examples in section B, but not limiting only to this one, steroidal mixed tetraoxanes 1B08a and 1B08b were prepared from a gem-dihydroperoxide 4A04, and ketone 5, wherein R is ethanoyl, X is methoxy, under the same conditions as given in Example 4.

1B08a: Yield 70 mg (12%). Colorless solid, softens at 82–84° C. $[\alpha]_D^{20}$=+38.50 (c=1.07, $CHCl_3$). IR (KBr): 2952, 2869, 1738, 1440, 1378, 1239, 1028 cm$^{-1}$. $^1$H NMR (200 MHz, CDCl$_3$): 5.09 (bs, H—C(12)), 4.91 (bs, H—C(7)), 3.66 (s, CH$_3$O$_2$C(24)), 2.11 (s, CH$_3$COO—), 2.08 (s, CH$_3$COO—), 0.94 (s, H$_3$C—C(10)), 0.92 (d, J=6.4 Hz, H$_3$C—C(4'')), 0.81 (d, J=6.0 Hz, H$_3$C—C(20)), 0.73 (s, H$_3$C—C(13)). $^{13}$C NMR (50 MHz, CDCl$_3$): 174.39, 170.40, 108.35, 108.21, 75.12, 70.54, 51.35, 47.18, 44.90, 43.17, 37.53, 34.51, 34.43, 31.46, 30.70, 30.59, 28.26, 27.00, 25.53, 22.63, 21.94, 21.45, 21.25, 17.36, 12.05. Positive ESI-MS (m/z): 1319.84 ([2M+Na]$^+$, 22), 687.39 ([M+K]$^+$, 18), 671.41 ([M+Na]$^+$, 100), 666.45 ([M+NH$_4$]$^+$, 85). Positive high resolution ESI exact mass measurement: m/z 671.3764 corresponding to a molecular formula C$_{36}$H$_{56}$O$_{10}$Na (error in ppm: 1.0). Anal. (C$_{36}$H$_{56}$O$_{10}$) C, H.

1B08b: Yield 70 mg (12%). Mp=204–206° C. (colorless prisms, ether-hexane). $[\alpha]_D^{20}$=+36.88 (c=1.06, CHCl$_3$). IR (KBr): 2950, 2871, 1729, 1442, 1378, 1314, 1252, 1193, 1174, 1090, 1049, 1034 cm$^{-1}$. $^1$H NMR (200 MHz, CDCl$_3$): 5.08 (bs, H—C(12)), 4.91 (bs, H—C(7)), 3.66 (s, CH$_3$O$_2$C (24)), 2.12 (s, CH$_3$COO—), 2.08 (s, CH$_3$COO—), 0.94 (s, H$_3$C—C(10)), 0.92 (d, J=7.2 Hz, H$_3$C—C(4'')), 0.81 (d, J=6.0 Hz, H$_3$C—C(20)), 0.73 (s, H$_3$C—C(13). $^{13}$C NMR (50 MHz, CDCl$_3$): 174.40, 170.45, 108.41, 108.26, 75.16, 70.56, 51.38, 47.21, 44.94, 43.23, 37.55, 34.58, 34.45, 31.58, 30.72, 30.61, 28.33, 27.02, 25.60, 22.65, 21.98, 21.47, 21.31, 17.37, 12.09. Positive ESI-MS (m/z): 1319.82 ([2M+Na]$^+$, 31), 687.38 ([M+K]$^+$, 32), 671.40 ([M+Na]$^+$, 100), 666.44 ([M+NH$_4$]$^+$, 28). Positive high resolution ESI exact mass measurement: m/z 671.3746 corresponding to a molecular formula C$_{36}$H$_{56}$O$_{10}$Na (error in ppm: 3.8). Anal. (C$_{36}$H$_{56}$O$_{10}$) C, H.

EXAMPLE 10

Methyl 7α,12α-diacetoxy-5β-cholan-24-oate-3-spiro-6'-(1',2',4',5'-tetraoxacyclohexane)-3'-spiro-1''-((4''R or S)- and (4''S or R)-ethyl)cyclohexane (1B13a and 1B13b)

1B13a: Yield 91.9 (15%). Colorless solid, softens at 72–76° C. $[\alpha]_D^{20}$=+41.99 (c=0.86, CHCl$_3$). IR (KBr): 3022w, 2941, 2876, 1739, 1448, 1378, 1244, 1174, 1082, 1034, 974, 764 cm$^{-1}$. $^1$H NMR (200 MHz, CDCl$_3$): 5.09 (bs, H—C(12)), 4.92 (bs, H—C(7)), 3.66 (s, CH$_3$O$_2$C(24)), 2.11 (s, CH$_3$COO—), 2.08 (s, CH$_3$COO—), 0.94–0.79 (m, H$_3$C—C(10), CH$_3$CH$_2$—C(4''), CH$_3$CH$_2$—C(4''), H$_3$C—C (20)), 0.73 (s, H$_3$C—C(13)). $^{13}$C NMR (50 MHz, CDCl$_3$): 174.54, 170.54, 108.59, 108.47, 75.25, 70.67, 51.48, 47.30, 45.00, 43.26, 38.24, 37.63, 34.62, 34.54, 30.82, 30.69, 28.60, 28.37, 27.10, 25.63, 22.74, 22.04, 21.56, 21.32, 17.45, 12.15, 11.52. Anal. (C$_{37}$H$_{58}$O$_{10}$) C, H.

1B13b: Yield 67.9 (12%). Colorless solid, softens at 110–114° C. $[\alpha]_D^{20}$=+43.40 (c=1.2, CHCl$_3$). IR (KBr): 2957, 2930, 2876, 1739, 1632, 1448, 1378, 1249, 1168, 1182, 1034, 969 cm$^{-1}$. $^1$H NMR (200 MHz, CDCl$_3$): 5.08 (bs, H—C(12)), 4.92 (bs, H—C(7)), 3.66 (s, CH$_3$O$_2$C(24)), 2.12 (s, CH$_3$COO—), 2.08 (s, CH$_3$COO—), 0.94–0.79 (m, H$_3$C—C(10), CH$_3$CH$_2$—C(4''), CH$_3$CH$_2$—C(4''), H$_3$C—C (20)), 0.73 (s, H$_3$C—C(13). $^{13}$C NMR (50 MHz, CDCl$_3$): 174.52, 170.58, 108.62, 108.47, 75.24, 70.65, 51.47, 47.28, 45.01, 43.29, 38.33, 37.61, 34.64, 34.52, 30.80, 30.68, 28.67, 28.39 27.09, 25.67, 22.72, 22.04, 21.56, 21.36, 17.43, 12.15, 11,52. Anal. (C$_{37}$H$_{58}$O$_{10}$) C, H.

EXAMPLE 11

Methyl 7α,12α-diacetoxy-5β-cholan-24-oate-3-spiro-6'-(1',2',4',5'-tetraoxacyclohexane)-3'-spiro-1''-(4''R or S)- and (4''S or R)-t-butyl)cyclohexane (1B09a and 1B09b)

1B09a: Yield 68 mg (11%). Colorless solid, softens at 111–114° C. $[\alpha]_D^{20}$=+41.04 (c=1.06, CHCl$_3$). IR (KBr):

2951, 2873, 1739, 1440, 1377, 1239, 1196, 1175 cm$^{-1}$. $^1$H NMR (200 MHz, CDCl$_3$): 5.09 (bs, H—C(12)), 4.92 (bs, H—C(7)), 3.66 (s, CH$_3$O$_2$C(24)), 2.12 (s, CH$_3$COO—), 2.08 (s, CH$_3$COO—), 0.94 (s, H$_3$C—C(10)), 0.86 (s, (CH$_3$)$_3$C—C(4'')), 0.81 (d, J=6.0 Hz H$_3$C—C(20)), 0.73 (s, H$_3$C—C(13)). $^{13}$C NMR (50 MHz, CDCl$_3$): 174.60, 170.66, 108.46, 108.32, 75.25, 70.66, 51.47, 47.38, 47.25, 44.98, 43.26, 37.58, 34.62, 34.51, 32.23, 30.79, 30.65, 28.35, 27.50, 27.06, 25.64, 22.69, 22.00, 21.56, 21.34, 17.39, 12.13. Positive ESI-MS (m/z): 1403.90 ([2M+Na]$^+$, 24), 729.42 ([M+K]$^+$, 11), 713.45 ([M+Na]$^+$, 100), 708.50 ([M+NH$_4$]$^+$, 36). Positive high resolution ESI exact mass measurement: m/z 713.4236 corresponding to a molecular formula C$_{39}$H$_{62}$O$_{10}$Na (error in ppm: 0.6). Anal. (C$_{39}$H$_{62}$O$_{10}$) C, H.

1B09b: Yield 174 mg (28%). Colorless solid, softens at 104–107° C. $[\alpha]_D^{20}$=+40.93 (c=0.96, CHCl$_3$). IR (KBr): 3530, 2995, 1739, 1637, 1441, 1377, 1239, 1078, 1029 cm$^{-1}$. $^1$H NMR (200 MHz, CDCl$_3$): 5.09 (bs, H—C(12)), 4.92 (bs, H—C(7)), 3.66 (s, CH$_3$O$_2$C(24)), 2.11 (s, CH$_3$COO—), 2.08 (s, CH$_3$COO—), 0.94 (s, H$_3$C—C(10)), 0.86 (s, (CH$_3$)$_3$C—C(4'')), 0.81 (d, J=6.2 Hz, H$_3$C—C(20)), 0.73 (s, H$_3$C—C(13). $^{13}$C NMR (50 MHz, CDCl$_3$): 174.57, 170.56, 108.46, 108.32, 75.23, 70.66, 51.49, 47.25, 44.99, 43.24, 37.60, 34.60, 32.27, 30.81, 30.68, 28.35, 27.50, 27.10, 25.62, 22.73, 22.05, 21.31, 17.45, 12.15. Positive ESI-MS (m/z): 1403.86 ([2M+Na]$^+$, 19), 729.41 ([M+K]$^+$, 13), 713.43 ([M+Na]$^+$, 98), 708.47 ([M+NH$_4$]$^+$, 100). Positive high resolution ESI exact mass measurement: m/z 713.4263 corresponding to a molecular formula C$_{39}$H$_{62}$O$_{10}$Na (error in ppm: 3.1). Anal. (C$_{39}$H$_{62}$O$_{10}$·0.5H$_2$O) C, H.

EXAMPLE 12

Methyl 7α,12α-diacetoxy-5β-cholan-24-oate-3-spiro-6'-(1',2',4',5'-tetraoxacyclohexane)-3'-spiro-1''-((4''R or S)- and (4''S or R)-phenyl)cyclohexane (1B14a and 1B14b)

To the solution of dihydroperoxide 33 (500 mg, 0.90 mmol) in CH$_2$Cl$_2$ (14 mL) and 4-phenylcyclohexanone (314 mg, 1.80 mmol) was added at r.t., and the reaction mixture was cooled with stirring in an ice-bath. After 30 min, 0.6 ml of ice-bath cooled (H$_2$SO$_4$: CH$_3$CN)-mixture (1:10, v/v) was added dropwise. The reaction mixture was stirred at 0° C. for 15 min, and after usual work-up[7] the crude product was purified by column chromatography (Lobar B, LichroPrep Si 60, eluent heptane/EtOAc (85:15); Lobar B, LichroPrep RP-8, eluent MeOH/H$_2$O (9:1)) to afford tetraoxanes 34 and 35.

1B14a: Colorless foam, softens at 101–104° C. $[\alpha]_D^{20}$=+34.27 (c=1.14, CHCl$_3$). IR (KBr): 2945, 2875, 1737, 1449, 1378, 1248, 1072, 1030, 945, 938 cm$^{-1}$. $^1$H NMR (200 MHz, CDCl$_3$): 7.40–7.10 (m, Ph-C(4'')), 5.10 (bs, H—C(12)), 4.93 (bs, H—C(7)), 3.66 (s, CH$_3$O$_2$C(24)), 2.12 (bs, CH$_3$COO—), 2.10 (bs, CH$_3$COO—), 0.95 (s, H$_3$C—C(10)), 0.82 (d, J=6.0 Hz H$_3$C—C(20)), 0.74 (s, H$_3$C—C(13)). $^{13}$C NMR (50 MHz, CDCl$_3$): 174.53, 170.54, 145.74, 128.43, 126.76, 126.28, 108.65, 107.83, 75.24, 70.65, 51.48, 47.29, 44.99, 43.43, 43.26, 37.63, 34.63, 34.53, 30.81, 30.68, 29.57, 28.36, 27.10, 25.64, 22.75, 22.05, 21.58, 21.32, 17.45, 12.15. Anal. (C$_{41}$H$_{58}$O$_{10}$·0.5H$_2$O) C, H.

1B14b: Colorless foam, softens at 186–190° C. $[\alpha]_D^{20}$=+47.67 (c=1.03, CHCl$_3$). IR (KBr): 2951, 2880, 1738, 1449, 1378, 1253, 1128, 1062, 1025, 970, 932 cm$^{-1}$. $^1$H NMR (200 MHz, CDCl$_3$): 7.40–7.20 (m, Ph-C(4'')), 5.09 (bs, H—C (12)), 4.93 (bs, H—C(7)), 3.66 (s, $CH_3O_2C(24)$), 2.13 (bs, $CH_3COO$—), 2.08 (bs, $CH_3COO$—), 0.96 (s, $H_3C$—C(10)), 0.81 (d, J=6.0 Hz $H_3C$—C(20)), 0.74 (s, $H_3C$—C(13)). $^{13}C$ NMR (50 MHz, $CDCl_3$): 174.53, 170.60, 145.73, 128.42, 126.79, 126.28, 108.66, 107.87, 75.25, 70.64, 51.48, 47.30, 45.02, 43.56, 43.30, 37.62, 34.66, 34.53, 30.81, 30.69, 29.53, 28.42, 27.10, 25.69, 22.73, 22.06, 21.38, 17.44, 12.17. Anal. ($C_{41}H_{58}O_{10}$) C, H.

EXAMPLE 13

Methyl 7α,12α-diacetoxy-5β-cholan-24-oate-3-spiro-6'-(1',2',4',5'-tetraoxacyclohexane)-3'-spiro-1"-(−)-menthane (1B10)

Yield 118 mg (19%). Colorless solid, softens at 93–95° C. IR (KBr): 2953, 1739, 1619, 1440, 1239, 1026 cm$^{-1}$. $^1H$ NMR (200 MHz, $CDCl_3$): 5.08 (bs, H—C(12)), 4.92 (bs, H—C(7)), 3.66 (s, $CH_3O_2(C24)$), 2.15 (s, $CH_3COO$—), 2.085 (s, $CH_3COO$—), 2.080 (s, $CH_3COO$—), 2.06 (s, $CH_3COO$—), 1.00–0.85 (m, $H_3C$—C(10), $(CH_3)_2CH$—C(2")), 0.81 (d, $H_3C$—C(20), J=5.8 Hz), 0.73 (s, $H_3C$—C(13)). $^{13}C$ NMR (50 MHz, $CDCl_3$): 174.53, 170.73, 170.53, 170.01, 111.19, 108.42, 108.35, 75.25, 75.31, 70.65, 70.57, 51.47, 49.80, 49.65, 47.23, 44.99, 43.34, 38.95, 38.82, 37.95, 37.60, 34.51, 34.20, 32.68, 31.94, 31.14, 30.77, 30.65, 30.43, 28.94, 28.64, 28.32, 27.08, 26.84, 25.62, 24.91, 24.53, 24.42, 23.04, 22.80, 22.70, 21.96, 21.78, 21.47, 21.25, 18.79, 18.43, 17.39, 12.15. Positive ESI-MS (m/z): 1403.73 ([2M+Na]$^+$, 20), 729.34 ([M+K]$^+$, 12), 713.38 ([M+Na]$^+$, 100), 708.32 ([M+NH$_4$]$^+$, 33). Anal. ($C_{39}H_{62}O_{10}$) C, H.

EXAMPLE 14

Methyl 7α,12α-diacetoxy-5β-cholan-24-oate-3-spiro-6'-(1',2',4',5'-tetraoxacyclohexane)-3'-spirocyclooctane (1B11)

Yield 203 mg (34%). Mp=181–183° C. (colorless prisms, ether-hexane). $[α]_D^{20}$=+44.58 (c=1.02, $CHCl_3$). IR (KBr): 2956, 2937, 2872, 1736, 1470, 1440, 1377, 1241, 1076, 1031 cm$^{-1}$. $^1H$ NMR (200 MHz, $CDCl_3$): 5.09 (bs, H—C(12)), 4.91 (bs, H—C(7)), 3.66 (s, $CH_3O_2C(24)$), 2.12 (s, $CH_3COO$—), 2.08 (s, $CH_3COO$—), 0.94 (s, $H_3C$—C(10)), 0.81 (d, J=6.0 Hz, $H_3C$—C(20)), 0.73 (s, $H_3C$—C(13)). $^{13}C$ NMR (50 MHz, $CDCl_3$): 174.35, 170.40, 111.96, 107.86, 75.11, 70.52, 53.33, 51.33, 47.14, 44.88, 43.15, 37.49, 34.51, 34.40, 31.98, 30.65, 30.57, 28.26, 26.99, 26.46, 25.53, 24.86, 24.26, 22.62, 21.94, 21.43, 21.22, 17.32, 12.04. Positive ESI-MS (m/z): 1347.82 ([2M+Na]$^+$, 31), 701.39 ([M+K]$^+$, 15), 685.40 ([M+Na]$^+$, 100), 680.46 ([M+NH$_4$]$^+$, 77). Positive high resolution ESI exact mass measurement: m/z 685.3942 corresponding to a molecular formula $C_{37}H_{58}O_{10}Na$ (error in ppm: 2.1). Anal. ($C_{37}H_{58}O_{10}$) C, H.

EXAMPLE 15

Methyl 7α,12α-diacetoxy-5β-cholan-24-oate-3-spiro-6'-(1',2',4',5'-tetraoxacyclohexane)-3'-spiro-1"-((4"R or S)- and (4"S or R)-ethoxycarbonyl)cyclohexane (1B12a and 1B12b)

1B12a Colorless solid. IR (film): 2953, 2875, 1738, 1454, 1383, 1319, 1248, 1205, 1134, 1077, 1034, 970, 942, 764 cm$^{-1}$. $^1H$ NMR (200 MHz, $CDCl_3$): 5.09 (bs, H—C(12)), 4.92 (bs, H—C(7)), 4.14 (q, J=7.2 Hz, $CH_3CH_2O_2C$—C(4")), 3.66 (s, $CH_3O_2C(24)$), 2.12 (bs, $CH_3COO$—), 2.09 (bs, $CH_3COO$—), 1.35–1.25 (m, $CH_3CH_2O_2C$—C(4")), 0.94 (s, $H_3C$—C(10)), 0.81 (d, J=6.0 Hz, $H_3C$—C(21)), 0.73 (s, $H_3C$—C(13)). $^{13}C$ NMR (50 MHz, $CDCl_3$): 174.57, 170.57, 108.68, 107.50, 75.23, 70.64, 60.40, 51.48, 47.30, 45.01, 43.27, 41.40, 37.63, 34.64, 34.53, 30.82, 29.64, 28.40, 27.10, 25.66, 22.74, 22.05, 21.58, 21.35, 17.45, 14.14, 12.16. Anal. ($C_{38}H_{58}O_{12}$) C,H 1B12b: Colorless solid. IR (film): 2946, 2882, 1738, 1447, 1376, 1325, 1254, 1205, 1177, 134, 1070, 1034, 970, 757 cm$^{-1}$. $^1H$ NMR (200 MHz, $CDCl_3$): 5.08 (bs, H—C(12)), 4.92 (bs, H—C(7)), 4.20–4.05 (m, $CH_3CH_2O_2C$—C(4")), 3.66 (s, $CH_3O_2C(24)$), 2.12 (bs, $CH_3COO$—), 2.08 (bs, $CH_3COO$—), 1.35–1.15 (m, $CH_3CH_2O_2C$—C(4")), 0.94 (s, $H_3C$—C(10)), 0.81 (d, J=6.0 Hz, $H_3C$—C(21)), 0.73 (s, $H_3C$—C(13)). $^{13}C$ NMR (50 MHz, $CDCl_3$): 174.52, 170.57, 108.69, 107.50, 75.26, 70.65, 60.40, 51.48, 47.31, 45.02, 43.29, 41.65, 37.63, 34.64, 34.53, 30.82, 30.69, 29.64, 28.42, 27.10, 25.68, 22.74, 22.05, 21.55, 21.37, 17.44, 14.14, 12.16. Anal. ($C_{38}H_{58}O_{12}$) C,H

C. DERIVATIZATION OF STEROIDAL MIXED TETRAOXANES

As mentioned earlier, in a preferred embodiment, methyl esters of the structural formula 1, wherein R is ethanoyl and X is methoxy, can be transformed into steroidal mixed tetraoxane acids and amides according to the above-referenced Schemes using conventional methods known in the art and the procedures given below.

EXAMPLE 16

7α,12α-Diacetoxy-5β-cholan-24-oic acid-3-spiro-6'-(1',2',4',5'-tetraoxacyclohexane)-3'-spirocyclohexane (1C15)

Methyl ester 1B05 (151.5 mg, 0.24 mmol) was hydrolyzed at 79° C. with NaOH (14.3 mg, 0.37 mmol) in i-PrOH/H$_2$O mixture (6 ml, 3:1 v/v). After 30 min. reaction was cooled to r.t., and diluted with 10 ml H$_2$O and 30 ml CH$_2$Cl$_2$. Water layer was acidified to pH 2 with diluted HCl, and layers were separated. Water layer was further extracted with CH$_2$Cl$_2$ (3×20 ml), combined organic layers were washed with water and brine, dried over anh. Na$_2$SO$_4$ and evaporated to dryness.

Mp 213–216° C. (colorless prisms, acetone/hexane). $[α]_D^{20}$=+44.50 (c=1.00, $CHCl_3$). IR (KBr): 3465, 3266, 2968, 2946, 1738, 1710, 1454, 1390, 1283, 1255, 1084, 1034 cm$^{-1}$. $^1H$ NMR (200 MHz, $CDCl_3$): 5.09 (bs, H—C(12)), 4.92 (bs, H—C(7)), 2.12 (s, $CH_3COO$—), 2.09 (s, $CH_3COO$—), 0.94 (s, $H_3C$—C(10)), 0.82 (d, J=6.0 Hz, $H_3C$—C(20)), 0.73 (s, $H_3C$—C(13)). $^{13}C$ NMR (50 MHz, $CDCl_3$): 179.83, 170.62, 108.45, 108.36, 75.25, 70.67, 47.26, 45.02, 43.27, 37.62, 34.64, 34.47, 30.74, 30.44, 28.38, 27.08, 25.66, 25.29, 22.72, 22.04, 21.58, 21.36, 17.42, 12.17. LSI-MS (m/z): 659.35 ([M+K]$^+$, 36), 643.37 ([M+Na]$^+$, 100), 501.35 (3), 338.37 (42). Anal. ($C_{34}H_{52}O_{10}$) C, H.

According to the above given experimental conditions, the following steroidal mixed tetraoxane acids were prepared according the the above-referenced Schemes using conventional methods known in the art:

EXAMPLE 17

7α,12α-Diacetoxy-5β-cholan-24-oic acid-3-spiro-6'-(1',2',4',5'-tetraoxacyclohexane)-3'-spiro-1"-(2"-methyl)cyclohexane (1C16)

Methyl ester mixture 8e (1B07) (151.5 mg, 0.24 mmol) was hydrolyzed using the same procedure as given above for 9b (1C15). Acid mixture 9d (1C16).

Yield 166.33 mg (84%). Colorless solid. $[\alpha]_D^{20}$=+32.46 (c=1.04, CHCl$_3$). IR (KBr): 3471, 3265, 2970, 2941, 1737, 1709, 1456, 1391, 1280, 1259, 1082, 1041 cm$^{-1}$. $^1$H NMR (200 MHz, CDCl$_3$): 5.09 (bs, H—C(12)), 4.93 (bs, H—C(7)), 2.14 (bs, CH$_3$COO—), 2.11 (bs, CH$_3$COO—), 2.10 (bs, CH$_3$COO—), 2.07 (bs, CH$_3$COO—), 1.00 (d, J=6.8 Hz, H$_3$C—C(2'')), 0.94 (s, H$_3$C—C(10)), 0.82 (d, J=6.0 Hz, H$_3$C—C(20)), 0.74 (s, H$_3$C—C(13)). $^{13}$C NMR (50 MHz, CDCl$_3$): 179.72, 170.69, 170.62, 108.41, 108.36, 75.29, 70.69, 47.28, 45.03, 43.27, 34.62, 34.63, 34.59, 34.49, 30.74, 30.46, 28.37, 27.08, 25.65, 22.72, 22.04, 21.53, 21.40, 17.42, 13.57, 12.17. Positive high resolution ESI exact mass measurement: m/z 657.3563, corresponding to a molecular formula C$_{35}$H$_{54}$O$_{10}$Na (error in ppm: 7.6). (C$_{35}$H$_{54}$O$_{10}$) C, H.

EXAMPLE 18

7α,12α-Diacetoxy-5β-cholan-24-oic acid-3-spiro-6'-(1',2',4',5'-tetraoxacyclohexane)-3'-spiro-1''-(4''R)-methyl)cyclohexane (1C17)

Methyl ester 8 g (1B08a) (500 mg, 0.77 mmol) was hydrolyzed using the same procedure as given above for 9B (1C15).

Yield 351 mg (72%). Mp=130.5–133° C. (colorless prisms, ether/hexane). $[\alpha]_D^{20}$=+38.38 (c=1.11). IR (KBr): 3457, 2953, 2932, 2875, 1738, 1717, 1646, 1454, 1390, 1262, 1169, 1027 cm$^{-1}$. $^1$H NMR (200 MHz, CDCl$_3$): 5.09 (bs, H—C(12)), 4.92 (bs, H—C(7)), 2.11 (bs, CH$_3$COO—), 2.09 (bs, CH$_3$COO—), 1.00–0.95 (m, H$_3$C—C(10) and H$_3$C—C(4'')), 0.82 (d, J=6.0 Hz, H$_3$C—C(20)), 0.73 (s, H$_3$C—C(13)). $^{13}$C NMR (50 MHZ, CDCl$_3$): 179.58, 170.61, 108.48, 108.35, 75.27, 70.71, 47.29, 45.03, 43.27, 34.65, 34.63, 34.50, 31.56, 30.72, 30.46, 28.38, 27.10, 25.65, 22.75, 22.60, 22.05, 21.58, 21.34, 17.45, 14.07, 12.18. Anal. (C$_{35}$H$_{54}$O$_{10}$·0.5C$_6$H$_{14}$) C, H.

EXAMPLE 19

7α,12α-Diacetoxy-5β-cholan-24-oic acid-3-spiro-6'-(1',2',4',5'-tetraoxacyclohexane)-3'-spiro-1''-(4''S)-methyl)cyclohexane (1C18)

Methyl ester 8h (1B08b) (500 mg, 0.77 mmol) was hydrolyzed using the same procedure as given above for 9b (1C15).

Yield 380 mg, (78%). Mp=213.5–215° C. (colorless prisms, Et$_2$O/hexane). $[\alpha]_D^{20}$=+44.38 (c=1.05). IR (KBr): 3280, 2968, 2896, 1745, 1703, 1454, 1390, 1269, 1169, 1084, 1034 cm$^{-1}$. $^1$H NMR (200 MHz, CDCl$_3$): 5.09 (bs, H—C(12)), 4.92 (bs, H—C(7)), 2.12 (bs, CH$_3$COO—), 2.08 (bs, CH$_3$COO—), 0.94 (s, H$_3$C—C(10)), 0.92 (d, J=6.8 Hz, H$_3$C—C(4'')), 0.79 (d, J=6.4 Hz, H$_3$C—C(20)), 0.73 (s, H$_3$C—C(13)). $^{13}$C NMR (50 MHz, CDCl$_3$): 179.29, 170.63, 108.50, 108.40, 75.28, 70.70, 47.32, 45.07, 43.32, 37.67, 34.67, 34.51, 31.68, 30.68, 30.48, 28.43, 27.11, 25.71, 22.76, 22.07, 21.58, 21.40, 17.45, 12.20. Positive ESI-MS (m/z): 1291.73 ([2M+Na]$^+$, 24), 673.33 ([M+K]$^+$, 26), 657.36 ([M+Na]$^+$, 100), 652.41 ([M+NH$_4$]$^+$, 28). Anal. (C$_{35}$H$_{54}$O$_{10}$) C, H.

X-ray Analysis of 9h (1C18). The crystal (0.60×0.40×0.15 mm) was mounted in inert oil and transferred to the cold gas stream (107 K) of a MAR345 image plate equipped with MoKα graphite monochromatized radiation (λ=0.71069 Å). Crystal data for C$_{35}$H$_{54}$O$_{10}$ are as follows: Mr=634.78, orthorhombic, space group P2$_1$2$_1$2$_1$, a=10.399(3), b=12.172 (4), c=26.433(8)Å, V=3346(2)Å$^3$, Z=4.

90 images at a crystal to detector distance of 140 mm and with Δφ=2° were collected giving a total of 20469 reflections of which 3313 were independent (Rint=0.057). The completeness to 2θ=50.8° is 95.1%. The structure was solved by direct methods and refined by full matrix least squares on F$^2$.¶ The positions of the hydrogen atoms were calculated and included in the refinement with a common isotropic temperature factor (U=0.052 Å$^2$). The acidic hydrogen atom could not be localised. The refinement converged to the final indices: goodness of fit=1.085; R$_1$=0.046 for 3118 observed reflections with I>2σ(I), R$_1$=0.048, wR$_2$=0.124 for all data.

EXAMPLE 20

7α,12α-Diacetoxy-5β-cholan-24-oic acid-3-spiro-6'-(1',2',4',5'-tetraoxacyclohexane)-3'-spiro-1''-((4''R or S)-ethyl)cyclohexane (1C34)

Methyl ester 8i (1B13a) (250 mg, 0.38 mmol) was transformed into 9i (1C34) (196 mg, 80%) using the same procedure as given above for 9b (1C15).

Mp=133–135° C. (Et$_2$O/hexane). $[\alpha]_D^{20}$=+41.74 (c=1.09, CHCl$_3$). IR (KBr): 2951, 2880, 1738, 1455, 1378, 1248, 1172, 1030, 943 cm$^{-1}$. $^1$H NMR (200 MHz, CDCl$_3$): 5.09 (bs, H—C(12)), 4.92 (bs, H—C(7)), 2.11 (bs, CH$_3$COO—), 2.09 (bs, CH$_3$COO—), 0.94–0.80 (m, H$_3$C—C(10), CH$_3$CH$_2$—C(4''), CH$_3$CH$_2$—C(4''), H$_3$C—C(20)), 0.73 (s, H$_3$C—C(13)). $^{13}$C NMR (50 MHz, CDCl$_3$): 179.77, 170.60, 108.60, 108.46, 75.26, 70.70, 47.27, 45.01, 43.26, 38.24, 37.63, 34.62, 34.48, 31.53, 30.75, 30.45, 28.60, 28.36, 27.08, 25.63, 22.73, 22.59, 22.04, 21.57, 21.32, 17.43, 14.06, 12.17, 11.52. Anal. (C$_{36}$H$_{56}$O$_{10}$) C, H.

EXAMPLE 21

7α,12α-Diacetoxy-5β-cholan-24-oic acid-3-spiro-6'-(1',2',4',5'-tetraoxacyclohexane)-3'-spiro-1''-((4''S or R)-ethyl)cyclohexane (1C39)

Methyl ester 8j (1B13b) (250 mg, 0.38 mmol) was transformed into 9j (1C39 (183 mg, 75%) using the same procedure as given above for 9b (1C15).

Colorless solid, softens at 112–116° C. $[\alpha]_D^{20}$=+67.39 (c=0.88, CHCl$_3$). IR (KBr): 2951, 2880, 1743, 1449, 1378, 1248, 1085, 1030, 965, 938, 905 cm$^{-1}$. $^1$H NMR (200 MHz, CDCl$_3$): 5.09 (bs, H—C(12)), 4.92 (bs, H—C(7)), 2.12 (bs, CH$_3$COO—), 2.08 (bs, CH$_3$COO—), 0.94–0.80 (m, H$_3$C—C(10), CH$_3$CH$_2$—C(4''), CH$_3$CH$_2$—C(4''), H$_3$C—C(20)), 0.73 (s, H$_3$C—C(13)). $^{13}$C NMR (50 MHz, CDCl$_3$): 179.60, 170.65, 108.64, 108.49, 75.27, 70.69, 47.28, 45.04, 43.30, 38.35, 37.63, 34.65, 34.49, 30.73, 30.46, 28.69, 28.40, 27.08, 25.69, 22.73, 22.04, 21.58, 21.38, 17.43, 12.18, 11.54. Anal. (C$_{36}$H$_{56}$O$_{10}$·0.5 C$_6$H$_{14}$) C, H.

EXAMPLE 22

7α,12α-Diacetoxy-5β-cholan-24-oic acid-3-spiro-6'-(1',2',4',5'-tetraoxacyclohexane)-3'-spiro-1''-((4''R or S)-phenyl)cyclohexane (1C44)

Methyl ester 34 (250 mg, 0.35 mmol) was hydrolysed at 90° C. with NaOH (21,1 mg, 0,53 mmol) in i-PrOH/H$_2$O mixture (10 mL, 3:1 v/v). After 30 min reaction was cooled and diluted with 10 mL H$_2$O and 30 mL CH$_2$Cl$_2$. Water layer was acidified to pH 2 with diluted HCl, and layers were separated. Water layer was further extracted with CH$_2$Cl$_2$ (3×20 mL), combined organic layers were washed with water and brine, dried over anh. Na$_2$SO$_4$ and evaporated to dryness.

Yield 215 mg (88%). Colorless foam softens at 139–143° C. $[\alpha]_D^{20}$=+32.48 (c=1.10, $CHCl_3$). IR (KBr): 3419, 2945, 2880, 1738, 1449, 1383, 1247, 1123, 1079, 1030, 970, 932 $cm^{-1}$. $^1H$ NMR (200 MHz, $CDCl_3$): 7.40–7.10 (m, Ph-C(4")), 5.10 (bs, H—C(12)), 4.93 (bs, H—C(7)), 2.13 (bs, $CH_3COO$—), 0.96 (s, $H_3C$—C(10)), 0.83 (d, J=4.6 Hz, $H_3C$—C(20)), 0.74 (s, $H_3C$—C(13)). $^{13}C$ NMR (50 MHz, $CDCl_3$): 170.62, 145.72, 128.42, 126.75, 126.28, 108.64, 107.84, 75.24, 70.68, 47.23, 44.98, 43.41, 37.59, 34.61, 34.46, 30.45, 29.56, 28.34, 27.05, 25.62, 24.49, 22.71, 22.04, 21.58, 21.33, 17.42, 12.16. Anal. ($C_{40}H_{56}O_{10}.H_2O$) C, H.

EXAMPLE 23

7α,12α-Diacetoxy-5β-cholan-24-oic acid-3-spiro-6'-(1',2',4',5'-tetraoxacyclohexane)-3'-spiro-1"-((4"S or R)-phenyl)cyclohexane (1C49)

Methyl ester 35 (250 mg, 0.35 mmol) was hydrolysed using the same procedure as given above for 36 (1C44).

Yield 229 mg (93%). Colorless foam softens at 137–140° C. $[\alpha]_D^{20}$=+43.87 (c=1.06, $CHCl_3$). IR (film): 3436, 2946, 1739, 1642, 1448, 1378, 1244,1131, 1061, 1033 $cm^{-1}$. $^1H$ NMR (200 MHz, $CDCl_3$): 7.40–7.10 (m, Ph-C(4")), 5.10 (bs, H—C(12)), 4.93 (bs, H—C(7)), 2.14 (bs, $CH_3COO$—), 2.09 (bs, $CH_3COO$—), 0.96 (s, $H_3C$—C(10)), 0.82 (d, J=5.6 Hz, $H_3C$—C(20)), 0.74 (s, $H_3C$—C(13)). $^{13}C$ NMR (50 MHz, $CDCl_3$): 179.78, 170.68, 145.72, 128.42, 126.78, 126.28, 108.65, 107.88, 75.26, 70.68, 47.26, 45.02, 43.54, 43.28, 37.60, 34.65, 34.46, 30.45, 29.53, 28.39, 27.07, 25.69, 22.71, 22.05, 21.59, 21.40, 17.41, 12.18. Anal. ($C_{40}H_{56}O_{10}.H_2O$) C, H.

Steroidal mixed tetraoxane amides can be obtained in from the corresponding acids according to the above-referenced Schemes using conventional methods known in the art and the procedures described below:

EXAMPLE 24

7α,12α-Diacetoxy-5β-cholan-24-amide-3-spiro-6'-(1',2',4',5'-tetraoxacyclohexane)-3'-spirocyclohexane (1C19)

A solution of acid 1C15 (310.9 mg, 0.5 mmol), in dry $CH_2Cl_2$ (30 ml), with added $Et_3N$ (69.6 μl, 0.5 mmol) and $ClCO_2Et$ (47.78 μl, 0.5 mmol), was stirred for 60 min at 0° C. Then a suspension of 10 eq. $NH_4Cl$ and 10 eq. $Et_3N$ in dry $CH_2Cl_2$ (20 ml) was added, and after 30 min of stirring at 0° C. the reaction mixture was wormed to r.t. After 90 min it was diluted with $H_2O$, the layers were separated and the reaction mixture was worked-up as given above. Crude product was purified by $SiO_2$ column chromatography as above (eluent: EtOAc).

Mp=208–210° C. (colorless powder, ether). $[\alpha]_D^{20}$=+48.30 (C=1.00, $CHCl_3$). IR (KBr): 3488, 3358, 2950, 2892, 1730, 1694, 1615, 1458, 1386, 1257, 1077, 1034, 955 $cm^{-1}$. $^1H$ NMR (200 MHz, $CDCl_3$): 5.6–5.4 (m, $H_2N$—C(24)), 5.10 (bs, H—C(12)), 4.92 (bs, H—C(7)), 2.12 (s, $CH_3COO$—), 2.09 (s, $CH_3COO$—), 0.94 (s, $H_3C$—C(10)), 0.83 (d, J=6.0 Hz, $H_3C$—C(20)), 0.73 (s, $H_3C$—C(13)). $^{13}C$ NMR (50 MHz, $CDCl_3$): 175.70, 170.58, 108.34, 75.24, 70.63, 47.41, 45.02, 43.26, 37.60, 34.63, 32.65, 31.29, 28.37, 27.14, 25.66, 25.27, 22.73, 22.04, 21.57, 21.37, 17.53, 12.19. Positive ESI-MS (m/z): 1261.81 ([2M+Na]+, 24), 658.39 ([M+K]+, 22), 642.41 ([M+Na]+, 100), 620.43 ([M+NH_4]+, 9). Positive high resolution ESI exact mass measurement: m/z 620.3804 corresponding to a molecular formula $C_{34}H_{53}NO_9Na$ (error in ppm: 0.8). Anal. ($C_{34}H_{53}NO_9$) C, H.

According to the above given experimental conditions, using the appropriate amines or salts thereof, the following steroidal mixed tetraoxane amides can be prepared from their corresponding acids using conventional methods known in the art:

EXAMPLE 25

N-(n-Propyl)-7α,12α-diacetoxy-5β-cholan-24-amide-3-spiro-6'-(1',2',4',5'-tetraoxacyclohexane)-3'-spirocyclohexane (1C20)

Acid 9b (1C15) (311.6 mg, 0.5 mmol) was transformed into amide 11 (1C20) (233 mg, 70%) according to general procedure using 82.1 mL (1 mmol) of n-PrNH2. Column chromatography: eluent EtOAc/heptane (95/5)

Mp=208–210° C. (colorless powder, ether). $[\alpha]_D^{20}$=+40.60 (c=1.00, $CHCl_3$). IR (KBr): 3473, 3402, 3351, 2942, 2878, 1744, 1658, 1551, 1450, 1386, 1250, 1085, 1034, 963 $cm^{-1}$. $^1H$ NMR (200 MHz, $CDCl_3$): 5.50, (bs, $CH_3CH_2CH_2NH$—C(24)), 5.08 (bs, H—C(12)), 4.91 (s, H—C(7)), 3.3–3.1 (m, $CH_3CH_2CH_2NH$—C(24)), 2.10 (s, $CH_3COO$—), 2.07 (s, $CH_3COO$—), 1.40–1.60 (m, $CH_3CH_2CH_2NH$—C(24)), 1.00–0.85 (m, $H_3C$—C(10) and $CH_3CH_2CH_2NH$—C(24)), 0.80 (d, J=6.0 Hz, $H_3C$—C(20), 0.71 (s, $H_3C$—C(13)). $^{13}C$ NMR (50 MHz, $CDCl_3$): 173.22, 170.57, 108.43, 108.32, 75.27, 70.64, 47.46, 45.01, 43.25, 41.12, 37.61, 34.68, 34.62, 33.55, 31.55, 28.37, 27.12, 25.65, 25.27, 22.82, 22.72, 22.03, 21.55, 21.35, 17.53, 12.17, 11.28. Positive ESI-MS (m/z): 1345.85 ([2M+Na]+, 32), 700.40 ([M+K]+, 14), 684.43 ([M+Na]+, 100), 662.44 ([M+H]+, 82). Positive high resolution ESI exact mass measurement: m/z 662.4287 corresponding to a molecular formula $C_{37}H_{60}NO_9$ (error in ppm: 2.8). Anal. ($C_{37}H_{59}NO_9.C_6H_{14}O$) C, H.

EXAMPLE 26

N-(Methyl ethanoate-2-yl)-7α,12α-diacetoxy-5β-cholan-24-amide-3-spiro-6'-(1',2',4',5'-tetraoxacyclohexane)-3'-spirocyclohexane (1C21)

The acid 9b (1C15) (300.9 mg, 0.48 mmol) was transformed into amide 12 (1C21) (216 mg, 64%) according to general procedure using suspension of 6 eq. of $NH_2CH_2CO_2Me.HCl$/6 eq. $Et_3N$ in dry $CH_2Cl_2$ (20 mL). Column chromatography: eluent EtOAc/heptane (95/5).

Mp=114–117° C. (colorless powder, ether/hexane). $[\alpha]_D^{20}$=+36.60 (c=1.00, $CHCl_3$). IR (KBr): 3452, 2950, 2878, 1759, 1737, 1666, 1551, 1450, 1379, 1257, 1207, 1085, 1034, 963 $cm^{-1}$. $^1H$ NMR (200 MHz, $CDCl_3$): 5.96, (bs, $CH_3O_2CCH_2NH$—C(24)), 5.09 (bs, H—C(12)), 4.92 (bs, H—C(7)), 4.04 (d, J=5.2 Hz, $CH_3O_2CCH_2NH$—C(24)), 3.77 (s, $CH_3O_2CCH_2NH$—C(24)), 2.12 (s, $CH_3COO$—), 2.09 (s, $CH_3COO$—), 0.94 (m, $H_3C$—C(10)), 0.82 (d, J=6.0 Hz, $H_3C$—C(20), 0.73 (s, $H_3C$—C(13)). $^{13}C$ NMR (50 MHz, $CDCl_3$): 173.38, 170.58, 108.45, 108.34, 75.27, 70.64, 52.34, 47.41, 45.02, 43.26, 41.12, 37.62, 34.64, 33.03, 31.25, 30.60, 28.38, 27.12, 25.66, 25.28, 22.73, 22.04, 21.58, 21.37, 17.52, 12.18. Positive ESI-MS (m/z): 1405.84 ([2M+Na]+, 9), 730.39 ([M+K]+, 16), 714.42 ([M+Na]+, 100), 692.43([M+H]+, 18). Positive high resolution ESI exact mass measurement: m/z 692.4027 corresponding to a molecular formula $C_{39}H_{62}O_{10}Na$ (error in ppm: 2.4). Anal. ($C_{37}H_{57}NO_{11}$) C, H.

EXAMPLE 27

7α,12α-Diacetoxy-5β-cholan-24-amide-3-spiro-6'-(1',2',4',5'-tetraoxacyclohexane)-3'-spiro-1"-(2"-methyl)cyclohexane (1C22)

The mixture of acids 9d (1C16) (322 mg, 0.50 mmol) was transformed into amide 13 (1C22) (220 mg, 68%) according to general procedure using suspension of 10 eq. NH$_4$Cl/10 eq. Et$_3$N in 20 mL dry CH$_2$Cl$_2$. Column chromatography: eluent EtOAc.

Colorless solid, softens at 131–138° C. $[\alpha]_D^{20}$=+36.69 (c=1.21, CHCl$_3$). IR (KBr): 3444, 2946, 2875, 1745, 1674, 1624, 1454, 1383, 1248, 1077, 1034, 970 cm$^{-1}$. $^1$H NMR (200 MHz, CDCl$_3$): 5.77 and 5.54 (both bs, H$_2$N—C(24)), 5.09 (bs, H—C(12)), 4.92 (bs, H—C(7)), 2.14 (bs, CH$_3$COO—), 2.13 (bs, CH$_3$COO—), 2.11 (bs, CH$_3$COO—), 2.07 (bs, CH$_3$COO—), 1.00 (d, J=6.8 Hz, H$_3$C—C(2'')), 0.94 (s, H$_3$C—C(10)), 0.83 (d, J=5.8 Hz, H$_3$C—C(20)), 0.74 (s, H$_3$C—C(13)). $^{13}$C NMR (50 MHz, CDCl$_3$): 175.97, 170.61, 109.38, 108.31, 75.25, 70.62, 47.38, 45.00, 43.21, 37.57, 34.62, 34.57, 32.64, 31.28, 30.47, 28.33, 27.10, 25.61, 24.44, 22.69, 21.99, 21.49, 21.37, 17.49, 13.54, 12.15. Positive high resolution ESI exact mass measurement: m/z 656.3737 corresponding to a molecular formula C$_{35}$H$_{55}$NO$_9$Na (error in ppm: 5.7) Anal. (C$_{35}$H$_{55}$NO$_9$·C$_6$H$_{14}$O) C, H.

EXAMPLE 28

N-Methyl-7α,12α-diacetoxy-5β-cholan-24-amide-3-spiro-6'-(1',2',4',5'-tetraoxacyclohexane)-3'-spiro-1''-(2''-methyl)cyclohexane (1C23)

The mixture of acids 9d (1C16) (255 mg, 0.40 mmol) was transformed into amide 14 (1C23) (168 mg, 64%) according to general procedure using suspension of 6 eq. MeNH$_2$.HCl/6 eq. Et$_3$N in 20 mL dry CH$_2$Cl$_2$. Column chromatography: eluent EtOAc.

Colorless solid, softens at 122–127° C. $[\alpha]_D^{20}$=+37.05 (c=1.42, CHCl$_3$). IR (KBr): 3437, 2946, 2882, 1745, 1660, 1560, 1447, 1383, 1248, 1077, 1034, 970 cm$^{-1}$. $^1$H NMR (200 MHz, CDCl$_3$): 5.54 (bs, H$_3$CNH—C(24)), 5.09 (bs, H—C(12)), 4.92 (bs, H—C(7)), 2.80 (d, J=4.6 Hz, H$_3$CNH—C(24)), 2.14 (bs, CH$_3$COO—), 2.13 (bs, CH$_3$COO—), 2.11 (bs, CH$_3$COO—), 2.10 (bs, CH$_3$COO—), 1.00 (d, J=6.8 Hz, H$_3$C—C(2'')), 0.94 (s, H$_3$C—C(10)), 0.81 (d, J=6.2 Hz, H$_3$C—C(20)), 0.73 (s, H$_3$C—C(13)). $^{13}$C NMR (50 MHz, CDCl$_3$): 173.90, 170.63, 108.34, 75.29, 70.64, 47.44, 45.01, 43.24, 37.63, 34.70, 34.60, 33.35, 31.48, 30.50, 28.35, 27.11, 26.23, 25.65, 24.50, 22.72, 22.02, 21.51, 21.41, 17.52, 13.55, 12.17. Positive high resolution ESI exact mass measurement: m/z 670.3914 corresponding to a molecular formula C$_{36}$H$_{57}$NO$_9$Na (error in ppm: 2.5). Anal. (C$_{36}$H$_{57}$NO$_9$) C, H.

EXAMPLE 29

N-Ethyl-7α,12α-diacetoxy-5β-cholan-24-amide-3-spiro-6'-(1',2',4',5'-tetraoxacyclohexane)-3'-spiro-1''-(2''-methyl)cyclohexane (1C24)

The mixture of acids 9d (1C16) (246 mg, 0.39 mmol) was transformed into amide 15 (1C24) (179 mg, 96%) according to general procedure using suspension of 6 eq. EtNH$_2$.HCl/6 eq. Et$_3$N in 20 mL dry CH$_2$Cl$_2$. Column chromatography: eluent EtOAc/heptane (95/5).

Colorless solid, softens at 119–125° C. $[\alpha]_D^{20}$=+38.29 (c=1.28, CHCl$_3$). IR (KBr): 3444, 2946, 2882, 1745, 1660, 1553, 1447, 1383, 1248, 1084, 1034, 970 cm$^{-1}$. $^1$H NMR (200 MHz, CDCl$_3$): 5.48 (bs, CH$_3$CH$_2$NH—C(24)), 5.09 (bs, H—C(12)), 4.92 (bs, H—C(7)), 3.36–3.20 (m, CH$_3$CH$_2$NH—C(24)), 2.14 (bs, CH$_3$COO—), 2.13 (bs, CH$_3$COO—), 2.11 (bs, CH$_3$COO—), 2.10 (bs, CH$_3$COO—), 2.06 (bs, CH$_3$COO—), 1.18–1.05 (m, CH$_3$CH$_2$NH—C(24)), 1.00 (d, J=6.6 Hz, H$_3$C—C(2'')), 0.94 (s, H$_3$C—C(10)), 0.82 (d, J=6.0 Hz, H$_3$C—C(20)), 0.73 (s, H$_3$C—C(13)). $^{13}$C NMR (50 MHz, CDCl$_3$): 173.09, 170.62, 170.32, 108.33, 75.29, 70.64, 47.43, 45.01, 43.24, 37.58, 34.68, 34.60, 34.25, 33.49, 31.49, 30.48, 28.34, 27.12, 25.64, 24.49, 22.71, 22.01, 21.51, 21.42, 17.54, 14.83, 13.54, 12.16. Positive high resolution ESI exact mass measurement: m/z 662.4267 corresponding to a molecular formula C$_{37}$H$_{59}$NO$_9$H (error in ppm: 0.2). Anal. (C$_{37}$H$_{59}$NO$_9$) C, H

EXAMPLE 30

N-(n-Propyl)-7α,12α-diacetoxy-5β-cholan-24-amide-3-spiro-6'-(1',2',4',5'-tetraoxacyclohexane)-3'-spiro-1''-(2''-methyl)cyclohexane (1C25)

The mixture of acids 9d (1C16) (258 mg, 0.41 mmol) was transformed into amide 16 (1C25) (193 mg, 70%) according to general procedure using 67 μL (0.81 mmol) n-PrNH$_2$. Colorless solid, softens at 111–116° C. Column chromatography: eluent EtOAc/heptane (95/5).

Colorless solid, softens at 111–116° C. $[\alpha]_D^{20}$=+41.85 (c=1.02, CHCl$_3$). IR (KBr): 3430, 2946, 2875, 1738, 1660, 1553, 1447, 1383, 1248, 1077, 1034, 970 cm$^{-1}$. $^1$H NMR (200 MHz, CDCl$_3$): 5.43 (bs, CH$_3$CH$_2$CH$_2$NH—C(24)), 5.09 (bs, H—C(12)), 4,92 (bs, H—C(7)), 3.30–3.10 (m, CH$_3$CH$_2$CH$_2$NH—C(24)), 2.14 (bs, CH$_3$COO—), 2.13 (bs, CH$_3$COO—), 2.11 (bs, CH$_3$COO—), 2.10 (bs, CH$_3$COO—), 2.06 (bs, CH$_3$COO—), 1.65–1.40 (m, CH$_3$CH$_2$CH$_2$NH—C(24)), 1.00 (d, J=6.8 Hz, H$_3$C—C(2'')), 0.96–0.85 (m, H$_3$C—C(10) and CH$_3$CH$_2$CH$_2$NH—C(24)), 0.82 (d, J=6.2 Hz, H$_3$C—C(21)), 0.73 (s, H$_3$C—C(13)). $^{13}$C NMR (50 MHz, CDCl$_3$): 173.20, 170.67, 108.38, 75.32, 70.66, 47.49, 45.05, 43.27, 41.16, 37.64, 34.72, 34.64, 33.60, 31.58, 30.56, 28.39, 27.15, 25.68, 24.45, 22.86, 22.81, 22.04, 21.54, 17.57, 13.59, 12.20, 11.30. Positive high resolution ESI exact mass measurement: m/z 698.4250 corresponding to a molecular formula C$_{38}$H$_{61}$NO$_9$Na (error in ppm: 0.9). Anal. (C$_{38}$H$_{61}$NO$_9$) C, H

EXAMPLE 31

7α,12α-Diacetoxy-5β-cholan-24-amide-3-spiro-6'-(1',2',4',5'-tetraoxacyclohexane)-3'-spiro-1''-((4''R)-methyl)cyclohexane (1C26)

Acid 9 g (1C17) (322 mg, 0.51 mmol) was transformed into 17 (1C26) (240 mg, 74%) using suspension of 10 eq. NH$_4$Cl/10 eq. Et$_3$N in 20 ml dry CH$_2$Cl$_2$. Column chromatography: Lobar B, LichroPrep Si 60; eluent EtOAc.

Colorless solid, softens at 137–141° C. $[\alpha]_D^{20}$=+44.71 (c=1.04). IR (KBr): 3458, 2946, 2882, 1738, 1681, 1454, 1383, 1255, 1106, 1027, 978, 906 cm$^{-1}$. $^1$H NMR (200 MHz, CDCl$_3$): 5.60–5.40 (m, H$_2$N—C(24), exchangeable with D$_2$O), 5.09 (bs, H—C(12)), 4.91 (bs, H—C(7)), 2.11 (bs, CH$_3$COO—), 2.09 (bs, CH$_3$COO—), 0.94 (s, H$_3$C—C(10)), 0.92 (d, J=6.0 Hz, H$_3$C—C(4'')), 0.83 (d, J=6.0 Hz, H$_3$C—C(20)), 0.73 (s, H$_3$C—C(13)). $^{13}$C NMR (50 MHz, CDCl$_3$): 175.72, 170.54, 108.46, 108.33, 75.26, 70.66, 47.42, 45.04, 43.25, 37.63, 34.66, 34.62, 32.66, 31.55, 31.31, 30.61, 28.37, 27.15, 25.65, 22.80, 22.04, 21.57, 21.33, 17.55. 12.19. Anal. (C$_{35}$H$_{55}$NO$_9$) C, H.

EXAMPLE 32

N-Methyl-7α,12α-diacetoxy-5β-cholan-24-amide-3-spiro-6'-(1',2',4',5'-tetraoxacyclohexane)-3'-spiro-1''-((4''R)-methyl)cyclohexane (1C27)

Acid 9g (1C17) (301 mg, 0.47 mmol) was transformed into 18 (1C27) (252 mg, 82%) according to general procedure using suspension of 6 eq. MeNH$_3$Cl/6 eq. Et$_3$N in 20 ml dry CH$_2$Cl$_2$. Column chromatography: Lobar B, LichroPrep Si 60; eluent EtOAc Colorless solid, softens at 129–134° C. $[\alpha]_D^{20}$=+43.66 (c=1.06). IR (KBr): 3465, 3415, 2953, 2882, 1745, 1653, 1560, 1454, 1390, 1248, 1027, 978, 906 cm$^{-1}$. $^1$H NMR (200 MHz, CDCl$_3$): 5.46 (bs, CH$_3$NH—C(24), exchangeable with D$_2$O), 5.09 (bs, H—C(12)), 4.91 (bs, H—C(7)), 2.80 (d, J=4.8 Hz, CH$_3$HN—C(24)), 2.10 (bs, CH$_3$COO—), 2.08 (bs, CH$_3$COO—), 0.94 (s, H$_3$C—C(10)), 0.92 (d, J=5.8 Hz, H$_3$C—C(4")), 0.81 (d, J=6.0 Hz, H$_3$C—C(20)), 0.73 (s, H$_3$C—C13)). $^{13}$C NMR (50 MHz, CDCl$_3$): 173.89, 170.56, 108.47, 108.33, 75.28, 70.66, 47.46, 45.02, 43.25, 37.63, 34.72, 34.62, 33.39, 31.55, 30.58, 28.37, 27.13, 26.25, 25.64, 22.80, 22.04, 21.57, 21.33, 17.56, 12.19. Anal. (C$_{36}$H$_{57}$NO$_9$) C, H.

EXAMPLE 33

N-Ethyl-7α,12α-diacetoxy-5β-cholan-24-amide-3-spiro-6'-(1',2',4',5'-tetraoxacyclohexane)-3"-spiro-1"-((4"R)-methyl)cyclohexane (1C28)

Acid 9g (1C17) (308 mg, 0.49 mmol) was transformed into 19 (1C28) (288 mg, 90%) according to general procedure using suspension of 6 eq. EtNH$_3$Cl/6 eq. Et$_3$N in 20 ml dry CH$_2$Cl$_2$. Column chromatography: Lobar B, LichroPrep Si 60; eluent EtOAc/heptane (95/5)

Colorless solid, softens at 124–129° C. $[\alpha]_D^{20}$=+43.98 (c=1.06). IR (KBr): 3444, 2953, 2875, 1738, 1653, 1553, 1454, 1383, 1248, 1027, 978, 906 cm$^{-1}$. $^1$H NMR (200 MHz, CDCl$_3$): 5.42 (bs, CH$_3$CH$_2$NH—C(24) exchangeable with D$_2$O), 5.09 (bs, H—C(12)), 4.91 (bs, H—C(7)), 3.40–3.15 (m, CH$_3$CH$_2$NH—C(24)), 2.11 (bs CH$_3$COO—), 2.08 (bs CH$_3$COO—), 1.20–1.05 (m, CH$_3$CH$_2$NH—C(24)), 0.94 (s, H$_3$C—C(10)), 0.92 (d, J=5.6 Hz, H$_3$C—C(4")), 0.82 (d, J=6.0 Hz, H$_3$C—C(20)), 0.73 (s, H$_3$C—C(13)). $^{13}$C NMR (50 MHz, CDCl$_3$): 173.08, 170.56, 108.47, 108.33, 75.28, 70.66, 47.45, 45.02, 43.25, 37.63, 34.70, 34.62, 34.28, 33.52, 31.55, 30.58, 28.37, 27.14, 25.64, 22.80, 22.04, 21.57, 21.33, 17.57, 14.85, 12.18. Anal. (C$_{37}$H$_{59}$NO$_9$) C, H.

EXAMPLE 34

N-(n-Propyl)-7α,12α-diacetoxy-5β-cholan-24-amide-3-spiro-6'-(1',2',4',5'-tetraoxacyclohexane)-3'-spiro-1"-((4"R)-methyl)cyclohexane (1C29)

Acid 9g (1C17) (402 mg, 0.63 mmol) was transformed into 20 (1C29) (315 mg, 74%) according to general procedure using 104.26 μl (1.27 mmol) n-PrNH$_2$. Column chromatography: Lobar B, LichroPrep Si 60; eluent EtOAc/heptane (95/5).

Colorless solid, softens at 117–124° C. $[\alpha]_D^{20}$=+43.40 (c=1.00). IR (KBr): 3437, 2953, 2875, 1738, 1653, 1553, 1454, 1383, 1255, 1027, 978, 907 cm$^{-1}$. $^1$H NMR (200 MHz, CDCl$_3$): 5.60–5.40 (m, CH$_3$CH$_2$CH$_2$NH—C(24) exchangeable with D$_2$O), 5.09 (bs, H—C(12)), 4.92 (bs, H—C(7)), 3.30–3.10 (m, CH$_3$CH$_2$CH$_2$NH—C(24)), 2.11 (bs, CH$_3$COO—), 2.08 (bs, CH$_3$COO—), 1.65–1.40 (m, CH$_3$CH$_2$CH$_2$NH—C(24)), 1.00–0.85 (m, H$_3$C—C(10), H$_3$C—C(4") and CH$_3$CH$_2$CH$_2$NH—C(24)), 0.82 (d, J=6.2 Hz, H$_3$C—C(21)), 0.73 (s, H$_3$C—C(13)). $^{13}$C NMR (50 MHz, CDCl$_3$): 173.23, 170.57, 108.47, 108.33, 75.29, 70.67, 47.47, 45.02, 43.25, 41.15, 37.64, 34.71, 34.62, 33.58, 31.56, 30.58, 28.37, 27.14, 26.74, 22.85, 22.75, 22.04, 21.56, 21.33, 17.56, 12.18, 11.28. Anal. (C$_{39}$H$_{61}$NO$_9$) C, H.

EXAMPLE 35

7α,12α-Diacetoxy-5β-cholan-24-amide-3-spiro-6'-(1',2',4',5'-tetraoxacyclohexane)-3'-spiro-1"-((4"S)-methyl)cyclohexane (1C30)

Acid 9h (1C18), (312 mg, 0.49 mmol) was transformed into 21 (1C30) (237 mg, 78%) using suspension of 10 eq. NH$_4$Cl/10 eq. Et$_3$N in 20 ml dry CH$_2$Cl$_2$. Column chromatography: Lobar B, LichroPrep Si 60; eluent EtOAc Mp=205–206° C. (colorless prisms, ether). $[\alpha]_D^{20}$=+47.23 (c=1.12). IR (KBr): 3458, 2953, 2875, 1738, 1681, 1454, 1383, 1248, 1084, 1027, 978, 906 cm$^{-1}$. $^1$H NMR (200 MHz, CDCl$_3$): 5.60–5.40 (m, H$_2$N—C(24), exchangeable with D$_2$O), 5.09 (bs, H—C(12)), 4.91 (bs, H—C(7)), 2.12 (bs, CH$_3$COO—), 2.08 (bs, CH$_3$COO—), 0.94 (s, H$_3$C—C(10)), 0.92 (d, J=6.8 Hz, H$_3$C—C(4")), 0.83 (d, J=6.0 Hz, H$_3$C—C(20)), 0.73 (s, H$_3$C—C(13)). $^{13}$C NMR (50 MHz, CDCl$_3$): 175.77, 170.60, 108.48, 108.37, 75.26, 70.65, 47.42, 45.04, 43.28, 37.62, 34.64, 32.66, 31.64, 31.03, 30.56, 28.40, 27.14, 25.69, 22.79, 22.04, 21.38, 17.53, 12.20. Anal. (C$_{35}$H$_{55}$NO$_9$) C, H.

EXAMPLE 36

N-Methyl-7α,12α-diacetoxy-5β-cholan-24-amide-3-spiro-6'-(1',2',4',5'-tetraoxacyclohexane)-3'-spiro-1"-((4"S)-methyl)cyclohexane (1C31)

Acid 9h (1C18) (323 mg, 0.51 mmol) was transformed into 22 (1C31) (230 mg, 70%) according to general procedure using suspension of 6 eq. MeNH$_3$Cl/6 eq. Et$_3$N in 20 ml dry CH$_2$Cl$_2$. Column chromatography: Lobar B, LichroPrep Si 60; eluent EtOAc Colorless solid, softens at 130–135° C. $[\alpha]_D^{20}$=+46.02 (c=1.03). IR (KBr): 3422, 2953, 2882, 1738, 1660, 1560, 1454, 1383, 1248, 1169, 1084, 1027, 978, 906 cm$^{-1}$. $^1$H NMR (200 MHz, CDCl$_3$): 5.48 (bs, CH$_3$NH—C(24), exchangeable with D$_2$O), 5.09 (bs, H—C(12)), 4.91 (bs, H—C(7)), 2.80 (d, J=4.8 Hz, CH$_3$NH—C(24)), 2.12 (bs, CH$_3$COO—), 2.08 (bs, CH$_3$COO—), 0.94 (s, H$_3$C—C(10)), 0.92 (d, J=6.6 Hz, H$_3$C—C(4")), 0.81 (d, J=5.8. Hz, H$_3$C—C(20)), 0.73 (s, H$_3$C—C(13)). $^{13}$C NMR (50 MHz, CDCl$_3$): 173.90, 170.62, 108.49, 108.38, 75.29, 70.66, 47.47, 45.04, 43.28, 37.63, 34.72, 34.65, 33.39, 31.65, 31.50, 30.56, 28.40, 27.12, 26.25, 25.69, 22.80, 22.04, 21.57, 21.38, 17.55, 12.20. Anal. (C$_{36}$H$_{57}$NO$_9$) C, H.

EXAMPLE 37

N-Ethyl-7α,12α-diacetoxy-5β-cholan-24-amide-3-spiro-6'-(1',2',4',5'-tetraoxacyclohexane)-3'-spiro-1"-((4"S)-methyl)cyclohexane (1C32)

Acid 9h (1C18) (316 mg, 0.50 mmol) was transformed into 23 (1C32) (288 mg, 90%) according to general procedure using suspension of 6 eq. EtNH$_3$Cl/6 eq. Et$_3$N in 20 ml dry CH$_2$Cl$_2$. Column chromatography: Lobar B, LichroPrep Si 60; eluent EtOAc/heptane (95/5)

Colorless solid, softens at 122–126° C. $[\alpha]_D^{20}$=+44.13 (c=1.06). IR (KBr): 3415, 2946, 2882, 1738, 1653, 1553, 1454, 1383, 1241, 1084, 1027, 970, 907 cm$^{-1}$. $^1$H NMR (200 MHz, CDCl$_3$): 5.41 (bs, CH$_3$CH$_2$NH—C(24) exchangeable with D$_2$O), 5.09 (bs, H—C(12)), 4.91 (bs, H—C(7)), 3.40–3.15 (m, CH$_3$CH$_2$NH—C(24)), 2.12 (bs, CH$_3$COO—), 2.08 (bs, CH$_3$COO—), 1.20–1.05 (m, CH$_3$CH$_2$NH—C(24)), 0.94 (s, H$_3$C—C(10)), 0.92 (d, J=6.4 Hz, H$_3$C—C(4")), 0.81 (d, J=6.2 Hz, H$_3$C—C(20)), 0.73 (s, H$_3$C—C(13)). $^{13}$C NMR (50 MHz, CDCl$_3$): 173.09, 170.62, 108.50, 108.39, 75.31, 70.67, 47.47, 45.06, 43.30, 37.65, 34.66, 34.29, 33.54, 31.66, 31.52, 30.58, 28.42, 27.14, 25.70, 22.81, 22.06, 21.58, 21.40, 17.58, 14.86, 12.20. Anal. ($C_{37}H_{59}NO_9$) C, H.

EXAMPLE 38

N-(n-Propyl)-7α,12α-diacetoxy-5β-cholan-24-amide-3-spiro-6'-(1',2',4',5'-tetraoxacyclohexane)-3'-spiro-1"-((4"S)-methyl)cyclohexane (1C33)

Acid 9g (1C17) (325 mg, 0.51 mmol) was transformed into 24 (1C33) (241 mg, 70%) according to general procedure using 83.74 μl (1.02 mmol) n-PrNH$_2$. Column chromatography: Lobar B, LicnroPrep Si 60; eluent EtOAc/heptane (95/5)

Mp=208–210° C. (colorless prisms, $CH_2Cl_2$/(i-Pr)$_2$O). $[\alpha]_D^{20}$=+44.88 (c=1.05). IR (KBr): 3309, 2953, 2868, 1745, 1653, 1553, 1461, 1383, 1241, 1162, 1084, 1041, 970, 942, 907 cm$^{-1}$. $^1$H NMR (200 MHz, CDCl$_3$): 5.60–5.40 (m, CH$_3$CH$_2$CH$_2$NH—C(24) exchangeable with D$_2$O), 5.09 (bs, H—C(12)), 4.92 (bs, H—C(7)), 3.30–3.10 (m, CH$_3$CH$_2$CH$_2$NH—C(24)), 2.12 (bs, CH$_3$COO—), 2.08 (bs, CH$_3$COO—), 1.60–1.35 (m, CH$_3$CH$_2$CH$_2$NH—C(24)), 1.00–0.85 (m, H$_3$C—C(10), H$_3$C—C(4") and CH$_3$CH$_2$CH$_2$NH—C(24)), 0.81 (d, J=6.2 Hz, H$_3$C—C(21)), 0.73 (s, H$_3$C—C(13)). $^{13}$C NMR (50 MHz, CDCl$_3$): 173.20, 170.60, 108.48, 108.36, 75.29, 70.66, 47.47, 45.03, 43.27, 41.13, 37.62, 34.69, 34.64, 33.57, 31.64, 31.56, 28.39, 27.12, 25.69, 22.84, 22.73, 22.04, 21.55, 21.38, 17.54, 12.19, 11.28. Anal. ($C_{39}H_{61}NO_9$) C, H.

EXAMPLE 39

7α,12α-Diacetoxy-5β-cholan-24-amide-3-spiro-6'-(1',2',4',5'-tetraoxacyclohexane)-3'-spiro-1"-((4"R or S)-ethyl)cyclohexane (1C35)

Acid 9i (1C34) (345 mg, 0.53 mmol) was transformed into 25 (1C35) (294 mg, 85%) using suspension of 10 eq. NH$_4$Cl/10 eq. Et$_3$N in 20 ml dry CH$_2$Cl$_2$. Column chromatography: Lobar B, LichroPrep Si 60; eluent EtOAc.

Colorless solid, softens at 133–136° C. $[\alpha]_D^{20}$=+46.17 (c=1.12, CHCl$_3$). IR (KBr): 3462, 3370, 2945, 2875, 1738, 1678, 1455, 1383, 1248, 1128, 1085, 1030, 970, 938, 905 cm$^{-1}$. $^1$H NMR (200 MHz, CDCl$_3$): 5.84–5.60 (m, H$_2$N—C(24)), 5.09 (bs, H—C(12)), 4.92 (bs, H—C(7)), 2.11 (bs, CH$_3$COO—), 2.09 (bs, CH$_3$COO—), 0.945–0.80 (m, H$_3$C—C(10)), CH$_3$CH$_2$—C(4"), CH$_3$CH$_2$—C(4"), H$_3$C—C(20)), 0.73 (s, H$_3$C—C(13)). $^{13}$C NMR (50 MHz, CDCl$_3$): 176.04, 170.52, 108.52, 108.38, 75.20, 70.61, 47.34, 44.96, 43.16, 38.16, 37.55, 34.60, 34.54, 32.61, 31.25, 30.49, 28.53, 28.29, 27.07, 25.57, 22.66, 21.97, 21.50, 21.26, 17.48, 12.12, 11.46. Anal. ($C_{36}H_{57}NO_9$) C, H

EXAMPLE 40

N-Methyl-7α,12α-Diacetoxy-5β-cholan-24-amide-3-spiro-6'-(1',2',4',5'-tetraoxacyclohexane)-3'-spiro-1"-((4"R or S)-ethyl)cyclohexane (1C36)

Acid 9i (1C34) (326 mg, 0.50 mmol) was transformed into 25 (1C35) (254 mg, 76%) according to general procedure using suspension of 6 eq. MeNH$_3$Cl/6 eq. Et$_3$N in 20 ml dry CH$_2$Cl$_2$. Column chromatography: Lobar B, LichroPrep Si 60; eluent EtOAc Colorless solid, softens at 123–127° C. $[\alpha]_D^{20}$=+46.01 (c=1.15, CHCl$_3$). IR (KBr): 3404, 2952, 2882, 1739, 1664, 1551, 1454, 1378, 1249, 1169, 1082, 1028, 969, 937, 904 cm$^{-1}$. $^1$H NMR (200 MHz, CDCl$_3$): 5.70–5.60 (HN—C(24)), 5.08 (bs, H—C(12)), 4.91 (bs, H—C(12)), 2.78 (d, J=4.80 Hz, H$_3$C—NH), 2.10 (bs, CH$_3$COO—), 2.08 (bs, CH$_3$COO—), 0.94–0.79 (m, H$_3$C—C(10), CH$_3$CH$_2$—C(4"), CH$_3$CH$_2$—C(4"), H$_3$C—C(20)), 0.73 (s, H$_3$C—C13)). $^{13}$C NMR (50 MHz, CDCl$_3$): 173.94, 170.47, 108.48, 108.34, 75.18, 70.57, 47.36, 44.91, 43.13, 38.12, 37.51, 34.63, 34.51, 33.24, 31.41, 28.50, 28.26, 27.02, 26.13, 25.53, 22.64, 21.94, 21.46, 17.45, 12.09, 11.42. Anal. ($C_{37}H_{59}NO_9 \cdot 0.5H_2O$) C, H.

EXAMPLE 41

N-Ethyl-7α,12α-Diacetoxy-5β-cholan-24-amide-3-spiro-6'-(1',2',4',5'-tetraoxacyclohexane)-3'-spiro-1"-((4"R or S)-ethyl)cyclohexane (1C37)

Acid 9i (1C34) (301 mg, 0.48 mmol) was transformed into 26 (1C36) (265 mg, 82%) according to general procedure using suspension of 6 eq. EtNH$_3$Cl/6 eq. Et$_3$N in 20 ml dry CH$_2$Cl$_2$. Column chromatography: Lobar B, LichroPrep Si 60; eluent EtOAc/heptane (95/5).

Colorless solid, softens at 115–118° C. $[\alpha]_D^{20}$=+46.09 (c=1.06, CHCl$_3$). IR (KBr): 3343, 2951, 2880, 1743, 1656, 1542, 1455, 1378, 1242, 1161, 1085, 1030, 970, 938, 905 cm$^{-1}$. $^1$H NMR (200 MHz, CDCl$_3$): 5.75–5.60 (HN—C(24)), 5.09 (bs, H—C(12)), 4.92 (bs, H—C(7)), 3.40–3.15 (m, CH$_3$CH$_2$—NH—), 2.11 (bs CH$_3$COO—), 2.08 (bs CH$_3$COO—), 1.20–1.05 (m, CH$_3$CH$_2$—NH—), 0.94–0.80 (m, H$_3$C—C(10), CH$_3$CH$_2$—C(4"), CH$_3$CH$_2$—C(4"), H$_3$C—C(20)), 0.73 (s, H$_3$C—C(13)). $^{13}$C NMR (50 MHz, CDCl$_3$): 173.09, 170.46, 108.48, 108.35, 75.19, 70.57, 47.35, 44.91, 43.14, 38.13, 37.52, 34.61, 34.51, 34.16, 33.39, 31.42, 28.50, 28.26, 27.03, 25.53, 22.64, 21.94, 21.46, 21.23, 17.46, 14.74, 12.08, 11.42. Anal. ($C_{38}H_{61}NO_9$) C, H.

EXAMPLE 42

N-(n-Propyl)-7α,12α-Diacetoxy-5β-cholan-24-amide-3-spiro-6'-(1',2',4',5'-tetraoxacyclohexane)-3'-spiro-1"-((4"R or S)-ethyl)cyclohexane (1C38)

Acid 9i (1C34) (304 mg, 0.47 mmol) was transformed into 28 (1C38) (245 mg, 79%) according to general procedure using 75.95 μl (0.94 mmol) n-PrNH$_2$. Column chromatography: Lobar B, LichroPrep Si 60; eluent EtOAc/heptane (95/5).

Colorless solid, softens at 112–116° C. $[\alpha]_D^{20}$=+45.44 (c=1.01, CHCl$_3$). IR (KBr): 3321, 2962, 2935, 2875, 1738, 1655, 1547, 1455, 1378, 1248, 1161, 1085, 1031, 965, 938, 905 cm$^{-1}$. $^1$H NMR (200 MHz, CDCl$_3$): 5.60–5.40 (m, HN—C(24)), 5.09 (bs, H—C(12)), 4,92 (bs, H—C(7)), 3.30–3.10 (m, CH$_3$CH$_2$CH$_2$—NH—), 2.11 (bs, CH$_3$COO—), 2.08 (bs, CH$_3$COO—), 1.65–1.35 (m, CH$_3$CH$_2$CH$_2$—NH—), 1.00–0.80 (m, H$_3$C—C(10), CH$_3$CH$_2$—C(4"), CH$_3$CH$_2$—C(4"), CH$_3$CH$_2$CH$_2$—NH—), H$_3$C—C(21)), 0.73 (s, H$_3$C—C(13)). $^{13}$C NMR (50 MHz, CDCl$_3$): 173.20, 170.52, 108.55, 108.42, 75.25, 70.63, 47.43, 44.98, 43.20, 41.11, 38.19, 37.59, 34.67, 34.57, 33.52, 31.53 30.53, 28.56, 28.33, 27.11, 25.60, 22.80, 22.70, 22.00, 21.53, 21.30, 17.52, 12.14, 11.49, 11.27. Anal. ($C_{39}H_{63}NO_{10}$) C, H

EXAMPLE 43

7α,12α-Diacetoxy-5β-cholan-24-amide-3-spiro-6'-(1',2',4',5'-tetraoxacyclohexane)-3'-spiro-1"-((4"S or R)-ethyl)cyclohexane (1C40)

Acid 9j (1C39) (356 mg 0.55 mmol) was transformed into 29 (1C40) (269 mg, 76%) using suspension of 10 eq.

NH$_4$Cl/10 eq. Et$_3$N in 20 ml dry CH$_2$Cl$_2$. Column chromatography: Lobar B, LichroPrep Si 60; eluent EtOAc Colorless solid, softens at 131–134° C. [α]$_D^{20}$=+45.43 (c=1.12, CHCl$_3$). IR (KBr): 3457, 3364, 2950, 2880, 1743, 1683, 1455, 1384, 1248, 1128, 1166, 1085, 1057, 1030, 970, 938, 905 cm$^{-1}$. $^1$H NMR (200 MHz, CDCl$_3$): 5.85–5.40 (m, H$_2$N—C(24)), 5.09 (bs, H—C(12)), 4.92 (bs, H—C(7)), 2.12 (bs, CH$_3$COO—), 2.08 (bs, CH$_3$COO—), 0.95–0.80 (m, H$_3$C—C(10)), CH$_3$CH$_2$—C(4"), CH$_3$CH$_2$—C(4"), H$_3$C—C(20)), 0.73 (s, H$_3$C—C(13)). $^{13}$C NMR (50 MHz, CDCl$_3$): 175.97, 170.59, 108.59, 108.42, 75.23, 70.62, 47.37, 44.00, 43.24, 38.28, 37.57, 34.60, 32.63, 31.27, 28.64, 28.35, 27.10, 25.64, 22.68, 22.00, 21.54, 21.35, 17.49, 12.16, 11.50. Anal. (C$_{36}$H$_{57}$NO$_9$) C, H

EXAMPLE 44

N-Methyl-7α,12α-Diacetoxy-5β-cholan-24-amide-3-spiro-6'-(1',2',4',5'-tetraoxacyclohexane)-3'-spiro-1"-((4"S or R)-ethyl)cyclohexane (1C41)

Acid 9j (1C39) (316 mg, 0.49 mmol) was transformed into 30 (1C41) (247 mg, 77%) according to general procedure using suspension of 6 eq. MeNH$_3$Cl/6 eq. Et$_3$N in 20 ml dry CH$_2$Cl$_2$. Column chromatography: Lobar B, LichroPrep Si 60; eluent EtOAc.

Colorless solid, softens at 122–125° C. [α]$_D^{20}$=+43.78 (c=0.98, CHCl$_3$). IR (KBr): 3356, 2962, 2935, 2876, 1739, 1659, 1551, 1454, 1378, 1249, 1163, 1082, 1044, 969, 932, 909 cm$^{-1}$. $^1$H NMR (200 MHz, CDCl$_3$): 5.75–5.60 (m, HN—C(24)), 5.08 (bs, H—C(12)), 4.91 (bs, H—C(12)), 2.79 (d, J=4.80 Hz, H$_3$C—NH), 2.12 (bs, CH$_3$COO—), 2.08 (bs, CH$_3$COO—), 1.00–0.79 (m, H$_3$C—C(10), CH$_3$CH$_2$—C(4"), CH$_3$CH$_2$—C(4"), H$_3$C—C(20)), 0.73 (s, H$_3$C—C(13)). $^{13}$C NMR (50 MHz, CDCl$_3$): 173.95, 170.54, 108.54, 108.38, 75.21, 70.58, 47.38, 44.94, 43.19, 38.24, 37.52, 34.64, 34.55, 33.26, 31.43, 28.59, 28.31, 27.03, 26.16, 25.60, 22.65, 21.96, 21.49, 21.31, 17.46, 12.11, 11.46. Anal. (C$_{37}$H$_{59}$NO$_9$) C, H.

EXAMPLE 45

N-Ethyl-7α,12α-Diacetoxy-5β-cholan-24-amide-3-spiro-6'-(1',2',4',5'-tetraoxacyclohexane)-3'-spiro-1"-((4"S or R)-ethyl)cyclohexane (1C42)

Acid 9j (1C39) (316 mg, 0.49 mmol) was transformed into 31 (1C42) (248 mg, 75%) according to general procedure using suspension of 6 eq. EtNH$_3$Cl/6 eq. Et$_3$N in 20 ml dry CH$_2$Cl$_2$. Column chromatography: Lobar B, LichroPrep Si 60; eluent EtOAc/heptane (95/5)

Colorless solid, softens at 115–119° C. [α]$_D^{20}$=+42.72 (c=1.03, CHCl$_3$). IR (KBr): 3392, 2956, 2934, 2875, 1743, 1656, 1536, 1460, 1378, 1242, 1166, 1085, 1030, 970, 938, 905 cm$^{-1}$. $^1$H NMR (200 MHz, CDCl$_3$): 5.5–5.35 (m, HN—C(24)), 5.09 (bs, H—C(12)), 4.91 (bs, H—C(7)), 3.40–3.10 (m, CH$_3$CH$_2$—NE—), 2.12 (bs CH$_3$COO—), 2.08 (bs CH$_3$COO—), 1.20–1.05 (m, CH$_3$CH$_2$—NH—), 1.00–0.75 (m, H$_3$C—C(10), CH$_3$CH$_2$—C(4"), CH$_3$CH$_2$—C(4"), H$_3$C—C(20)), 0.73 (s, H$_3$C—C(13)). $^{13}$C NMR (50 MHz, CDCl$_3$): 173.07, 170.50, 108.52, 108.36, 75.19, 70.56, 47.36, 44.93, 43.18, 38.22, 37.51, 34.60, 34.53, 34.16, 33.39, 31.42, 28.58, 28.29, 27.03, 25.59, 22.64, 21.94, 21.47, 21.29, 17.46, 14.74, 12.10, 11.44. Anal. (C$_{38}$H$_{61}$NO$_9$·⅔H$_2$O) C, H

EXAMPLE 46

N-(n-Propyl)-7α,12α-Diacetoxy-5β-cholan-24-amide-3-spiro-6'-(1',2',4',5'-tetraoxacyclohexane)-3'-spiro-1"-((4"S or R)-ethyl)cyclohexane (1C43)

Acid 9j (1C39) (305 mg, 0.47 mmol) was transformed into 32 (1C43) (251 mg, 77%) according to general procedure using 77.17 μl (0.94 mmol) n-PrNH$_2$. Column chromatography: Lobar B, LichroPrep Si 60; eluent EtOAc/heptane (95/5).

Colorless solid, softens at 113–117° C. [α]$_D^{20}$=+44.32 (c=1.06, CHCl$_3$). IR (KBr): 3408, 2962, 2939, 2875, 1743, 1661, 1547, 1449, 1378, 1242, 1166, 1079, 1031, 970, 938, 905 cm$^{-1}$. $^1$H NMR (200 MHz, CDCl$_3$): 5.60–5.40 (m, HN—C(24)), 5.09 (bs, H—C(12)), 4,91 (bs, H—C(7)), 3.30–3.10 (m, CH$_3$CH$_2$CH$_2$—NH—), 2.12 (bs, CH$_3$COO—), 2.08 (bs, CH$_3$COO—), 1.65–1.35 (m, CH$_3$CH$_2$CH$_2$—NH—), 1.00–0.80 (m, H$_3$C—C(10), CH$_3$CH$_2$—C(4"), CH$_3$CH$_2$—C(4"), CH$_3$CH$_2$CH$_2$—NH—), H$_3$C—C(21)), 0.73 (s, H$_3$C—C(13)). $^{13}$C NMR (50 MHz, CDCl$_3$): 173.20, 170.59, 108.61, 108.45, 75.27, 70.64, 47.45, 45.01, 43.26, 41.12, 38.31, 37.60, 34.67, 34.63, 33.54, 31.55 28.65, 28.37, 27.12, 25.67, 22.82, 22.71, 22.02, 21.54, 21.37, 17.53, 12.17, 11.51, 11.28. Anal. (C$_{39}$H$_{63}$NO$_9$) C, H

EXAMPLE 47

7α,12α-Diacetoxy-5β-cholan-24-amide-3-spiro-6'-(1',2',4',5'-tetraoxacyclohexane)-3'-spiro-1"-((4"R or S)-phenyl)cyclohexane (1C45)

A suspension of 10 eq. NH$_4$Cl and 10 eq. Et$_3$N in dry CH$_2$Cl$_2$ (20 mL) was added to 36 to obtain 38 (1C45). Column chromatography: eluent EtOAc.

Yield 209 mg (79%). Colorless foam softens at 142–146° C. [α]$_D^{20}$=+35.79 (c=1.08, CHCl$_3$). IR (KBr): 3458, 2946, 2876, 1739, 1675, 1621, 1448, 1378, 1243, 1131, 1082, 1034, 969, 937 cm$^{-1}$. $^1$H NMR (200 MHz, CDCl$_3$): 7.40–7.00 (m, Ph—C(4")), 5.80–5.40 (m, H$_2$N—C(24)), 5.10 (bs, H—C(12)), 4.93 (bs, H—C(7)), 2.12 (bs, CH$_3$COO—), 2.10 (bs, CH$_3$COO—), 0.95 (s, H$_3$C—C(10)), 0.83 (d, J=5.6 Hz, H$_3$C—C(20)), 0.74 (s, H$_3$C—C(13)). $^{13}$C NMR (50 MHz, CDCl$_3$): 175.90, 170.57, 145.72, 128.43, 126.75, 126.28, 108.63, 107.83, 75.24, 70.65, 47.40, 45.01, 43.41, 43.23, 37.60, 34.61, 32.66, 31.29, 29.59, 28.34, 27.14, 25.64, 22.73, 22.04, 21.58, 21.34, 17.53, 12.18. Anal. (C$_{40}$H$_{57}$NO$_9$·0.5H$_2$O) C, H.

EXAMPLE 48

N-Methyl-7α,12α-Diacetoxy-5β-cholan-24-amide-3-spiro-6'-(1',2',4',5'-tetraoxacyclohexane)-3'-spiro-1"-((4"R or S)-phenyl)cyclohexane (1C46)

Acid 36 (263,7 mg 0,38 mmol) was transformed into 40 (1C46) (210 mg, 78%) according to general procedure using suspension of 6 eq. MeNH$_3$Cl/6 eq. Et$_3$N in 20 ml dry CH$_2$Cl$_2$. Column chromatography: Lobar B, LichroPrep Si 60; eluent EtOAc Colorless foam softens at 133–137° C. [α]$_D^{20}$=+28.03 (c=1.09, CHCl$_3$). IR (KBr): 3353, 2945, 2880, 1738, 1656, 1553, 1455, 1378, 1253, 1128, 1079, 1030, 965, 943 cm$^{-1}$. $^1$H NMR (200 MHz, CDCl$_3$): 7.40–7.10 (m, Ph-C(4")), 5.60–5.40 (m, HN—C(24)), 5.10 (bs, H—C(12)), 4.92 (bs, H—C(12)), 2.80 (d, J=4.80 Hz, H$_3$C—NH), 2.12 (bs, CH$_3$COO—), 0.95 (s, H$_3$C—C(10)), 0.82 (d, J=5.80 Hz, H$_3$C—C(20)), 0.73 (s, H$_3$C—C(13)). $^{13}$C NMR (50 MHz, CDCl$_3$): 173.93, 170.58, 145.71, 128.42, 126.74, 126.26, 108.62, 107.82, 75.25, 70.64, 47.42, 44.98, 43.40, 43.21, 37.59, 34.69, 34.60, 33.35, 31.47, 30.54, 29.55, 28.34, 27.12, 26.25, 25.62, 22.72, 22.04, 21.58, 21.33, 17.52, 12.17. Anal. (C$_{41}$H$_{59}$NO$_9$·0.5H$_2$O) C, H

EXAMPLE 49

N-Ethyl-7α,12α-Diacetoxy-5β-cholan-24-amide-3-spiro-6'-(1',2',4', 5'-tetraoxacyclohexane)-3'-spiro-1"-((4"R or S)-phenyl)cyclohexane (1C47)

Acid 36 (261,3 mg, 0,37 mmol) was transformed into 42 (216 mg, 80%) according to general procedure using suspension of 6 eq. EtNH₃Cl/6 eq. Et₃N in 20 ml dry CH₂Cl₂. Column chromatography: Lobar B, LichroPrep Si 60; eluent EtOAc/heptane (95/5).

Colorless foam, softens at 128–131° C. $[\alpha]_D^{20}$=+34.36 (c=1.04, CHCl₃). IR (KBr): 3326, 2951, 2880, 1738, 1656, 1547, 1455, 1379, 1248, 1128, 1085, 1030, 965, 938 cm⁻¹. ¹H NMR (200 MHz, CDCl₃): 7.40–7.10 (m, Ph-C(4")), 5.60–5.40 (m, HN—C(24)), 5.10 (bs, H—C(12)), 4.92 (bs, H—C(7)), 3.40–3.10 (m, CH₃CH₂—NH—), 2.12 (bs CH₃COO—), 2.09 (bs CH₃COO—), 1.13 (t, J=7.2 Hz, CH₃CH₂—NH—)), 0.95 (s, H₃C—C(10)), 0.82 (d, J=6 Hz, H₃C—C(20)), 0.73 (s, H₃C—C(13)). ¹³C NMR (50 MHz, CDCl₃): 173.11, 170.58, 145.72, 128.42, 126.74, 126.28, 108.63, 107.82, 75.25, 70.63, 47.42, 44.98, 43.40, 43.22, 37.58, 34.67, 34.60, 34.25, 33.49, 31.48, 30.53, 29.43, 28.34, 27.12, 25.61, 22.71, 22.04, 21.56, 21.33, 17.54, 14.83, 12.16. Anal. (C₄₂H₆₁NO₉.0.5H₂O) C, H

EXAMPLE 50

N-(n-Propyl)-7α,12α-Diacetoxy-5β-cholan-24-amide-3-spiro-6'-(1',2',4',5'-tetraoxacyclohexane)-3'-spiro-1"-((4"R or S)-phenyl)cyclohexane (1C48)

Acid 36 (259.2 mg, 0.37 mmol) was transformed into 44 (210 mg, 76%) according to general procedure using 60.24 μL, (0.74 mmol) n-PrNH₂. Column chromatography: Lobar B, LichroPrep Si 60; eluent EtOAc/heptane (95/5).

Colorless foam, softens at 125–127° C. $[\alpha]_D^{20}$=+32.25 (c=1.10, CHCl₃). IR (KBr): 3413, 3326, 2945, 2875, 1738, 1656, 1547, 1455, 1378, 1248, 1128, 1078, 1030, 965, 943 cm⁻¹. ¹H NMR (200 MHz, CDCl₃): 7.40–7.10 (m, Ph-C(4")), 5.60–5.40 (m, HN—C(24)), 5.10 (bs, H—C(12)), 4.93 (bs, H—C(7)), 3.40–3.10 (m, CH₃CH₂CH₂—NH—), 2.12 (bs, CH₃COO—), 1.70–1.20 (m, CH₃CH₂CH₂—NH—), 1.00–0.80 (m, H₃C—C(10), CH₃CH₂CH₂—NH—)), 0.82 (d, J=6.0 Hz, H₃C—C(21)), 0.73 (s, H₃C—C(13)). ¹³C NMR (50 MHz, CDCl₃): 173.21, 170.59, 145.73, 128.43, 126.76, 126.28, 108.64, 107.83, 75.27, 70.65, 47.45, 44.99, 43.41, 43.23, 41.13, 37.59, 34.61, 33.55, 31.54, 29.55, 28.34, 27.13, 25.62, 22.83, 22.04, 21.57, 21.34, 17.54, 12.17, 11.30. Anal. (C₄₃H₆₃NO₉.0.5H₂O) C, H

EXAMPLE 51

7α,12α-Diacetoxy-5β-cholan-24-amide-3-spiro-6'-(1',2',4',5'-tetraoxacyclohexane)-3'-spiro-1"-((4"S or R)-phenyl)cyclohexane (1C50)

Acid 37, (273.5 mg, 0.39 mmol) was transformed into 39 (236 mg, 86%) using suspension of 10 eq. NH₄Cl/10 eq. Et₃N in 20 ml dry CH₂Cl₂. Column chromatography: Lobar B, LichroPrep Si 60; eluent EtOAc.

Colorless foam, softens at 141–144° C. $[\alpha]_D^{20}$=+41.37 (c=1.02, CHCl₃). IR (KBr): 3463, 3356, 2952, 2876, 1739, 1675, 1621, 1448, 1384, 1249, 1131, 1061, 1028, 969, 942 cm⁻¹. ¹H NMR (200 MHz, CDCl₃): 7.40–7.10 (m, Ph-C(4")), 5.70–5.30 (m, H₂N—C(24)), 5.13 (bs, H—C(12)), 4.95 (bs, H—C(7)), 2.16 (bs, CH₃COO—), 2.12 (bs, CH₃COO—), 0.99 (s, H₃C—C(10)), 0.86 (d, J=5.8 Hz, H₃C—C(20)), 0.77 (s, H₃C—C(13)). ¹³C NMR (50 MHz, CDCl₃): 175.83, 170.63, 145.74, 128.43, 126.80, 126.29, 108.66, 107.89, 75.28, 70.66, 47.43, 45.06, 43.56, 43.30, 37.63, 34.67, 32.70, 31.31, 29.56, 28.42, 27.15, 25.71, 22.75, 22.06, 21.59, 21.43, 17.55, 12.21. Anal. (C₄₀H₅₇NO₉.0.5H₂O) C, H

EXAMPLE 52

N-Methyl-7α,12α-Diacetoxy-5β-cholan-24-amide-3-spiro-6'-(1',2',4',5'-tetraoxacyclohexane)-3'-spiro-1"-((4"S or R)-phenyl)cyclohexane (1C51)

Acid 37 (256.7 mg, 0.37 mmol) was transformed into 41 (217 mg, 83%) according to general procedure using suspension of 6 eq. MeNH₃Cl/6 eq. Et₃N in 20 ml dry CH₂Cl₂. Column chromatography: Lobar B, LichroPrep Si 60; eluent EtOAc Colorless foam, softens at 137–140° C. $[\alpha]_D^{20}$=+47.15 (c=0.90, CHCl₃). IR (KBr): 3402, 3343, 2945, 2875, 1738, 1661, 1553, 1449, 1378, 1248, 1169, 1128, 1063, 1030, 970, 938 cm⁻¹. ¹H NMR (200 MHz, CDCl₃): 7.40–7.10 (m, Ph-C(4")), 5.60–5.30 (m, HN—C(24)), 5.09 (bs, H—C(12)), 4.92 (bs, H—C(12)), 2.80 (d, J=5.0 Hz, H₃C—NH), 2.13 (bs, CH₃COO—), 2.08 (bs, CH₃COO—), 0.96 (s, H₃C—C(10)), 0.81 (d, J=6.0 Hz, H₃C—C(20)), 0.73 (s, H₃C—C13)). ¹³C NMR (50 MHz, CDCl₃): 173.90, 170.63, 145.74, 128.43, 126.79, 126.28, 108.67, 107.88, 75.29, 70.65, 47.47, 45.04, 43.56, 43.29, 37.63, 34.67, 33.39, 31.50, 30.58, 29.60, 28.42, 27.13, 26.27, 25.70, 22.75, 22.06, 21.59, 21.41, 17.55, 12.21. Anal. (C₄₁H₅₉NO₉.0.5H₂O) C, H.

EXAMPLE 53

N-Ethyl-7α,12α-Diacetoxy-5β-cholan-24-amide-3-spiro-6'-(1',2',4',5'-tetraoxacyclohexane)-3'-spiro-1"-((4"S or R)-phenyl)cyclohexane (1C52)

Acid 37 (256.5 mg, 0.37 mmol) was transformed into 43 (224 mg, 84%)) according to general procedure using suspension of 6 eq. EtNH₃Cl/6 eq. Et₃N in 20 ml dry CH₂Cl₂. Column chromatography: Lobar B, LichroPrep Si 60; eluent EtOAc/heptane (95/5).

Colorless foam, softens at 129–132° C. $[\alpha]_D^{20}$=+46.12 (c=0.97, CHCl₃). IR (KBr): 3440, 2951, 2880, 1738, 1655, 1547, 1449, 1378, 1248, 1128, 1063, 1030, 970, 943 cm⁻¹. ¹H NMR (200 MHz, CDCl₃): 7.40–7.10 (m, Ph-C(4")), 5.60–5.40 (m, HN—C(24)), 5.10 (bs, H—C(12)), 4.92 (bs, H—C(7)), 3.40–3.10 (m, CH₃CH₂—NH—), 2.13 (bs CH₃COO—), 2.09 (bs CH₃COO—), 1.30–1.10 (m, CH₃CH₂—NH—)), 0.96 (s, H₃C—C(10)), 0.82 (d, J=5.8 Hz, H₃C—C(20)), 0.73 (s, H₃C—C(13)). ¹³C NMR (50 MHz, CDCl₃): 173.15, 170.60, 170.40, 145.69, 128.39, 126.76, 126.25, 108.62, 107.84, 75.26, 70.62, 47.42, 45.00, 43.51, 43.26, 37.58, 34.63, 34.24, 33.49, 31.48, 30.53, 29.48, 28.38, 27.11, 25.67, 22.70, 22.03, 21.54, 21.38, 17.53, 14.82, 12.17. Anal. (C₄₂H₆₁NO₉.0.5H₂O) C, H

EXAMPLE 54

N-(n-Propyl)-7α,12α-Diacetoxy-5β-cholan-24-amide-3-spiro-6'-(1',2',4',5'-tetraoxacyclohexane)-3'-spiro-1"-((4"S or R)-phenyl)cyclohexane (1C53)

Acid 37 (258.1 mg, 0.37 mmol) was transformed into 45 (214 mg, 78%) according to general procedure using 59.92 μL (0.74 mmol) n-PrNH₂. Column chromatography: Lobar B, LichroPrep Si 60; eluent EtOAc/heptane (95/5).

Colorless foam, softens at 127–131° C. $[\alpha]_D^{20}$=+45.23 (c=1.07, CHCl₃). IR (KBr): 3402, 3321, 2945, 2880, 1738, 1656, 1547, 1449, 1378, 1248, 1128, 1063, 1030, 970, 938 cm⁻¹. ¹H NMR (200 MHz, CDCl₃): 7.40–7.10 (m, Ph-C(4")), 5.50–5.30 (m, HN—C(24)), 5.10 (bs, H—C(12)), 4.92 (bs, H—C(7)), 3.40–3.10 (m, CH₃CH₂CH₂—NH—), 2.13 (bs, CH₃COO—), 2.08 (bs, CH₃COO—), 1.70–1.30 (m, CH₃CH₂CH₂—NH—), 1.00–0.80 (m, H₃C—C(10), CH₃CH₂CH₂—NH—)), 0.82 (d, J=6.0 Hz, H₃C—C(21)), 0.73 (s, H₃C—C(13)). ¹³C NMR (50 MHz, CDCl₃): 173.21, 170.62, 145.73, 128.42, 126.78, 126.28, 108.65, 107.87, 75.29, 70.64, 47.47, 45.03, 43.55, 43.28, 41.13, 37.61, 34.66, 33.58, 31.56, 29.53, 28.41, 27.13, 25.70, 22.85, 22.05, 21.57, 21.41, 17.55, 12.20, 11.30. Anal. (C₄₃H₆₃NO₉) C, H

EXAMPLE 55

N-(n-Propyl)-7α,12α-diacetoxy-5β-cholan-24-amide-3-spiro-6'-(1',2',4',5'-tetraoxacyclohexane)-3'-spirocyclohexane (1C20)

In this additional example for preparation of 1C20, as an exception of all other examples in Section C, but not limiting only to this one, the title compound was prepared directly from ketone of the structural formula 3, wherein R1 is H, R2 is H, R3 is H, R4 is H, and gem-dihydroperoxide 2A03, under the same conditions as given in Example 4.

Mp=208–209° C. (colorless powder, ether). $[\alpha]_D^{20}$=+ 40.39 (c 0.87, $CHCl_3$).

Anal. ($C_{37}H_{59}NO_9$) C, H.

D. ANTIMALARIAL DRUG SUSCEPTIBILITY ASSAY

EXAMPLE 56

The activity of the compounds of the present invention against parasite clones of chloroquine-susceptible malaria strain (Sierra Leone, D6), and chloroquine-resistant malaria strain (Indochina, W2) exhibited strong, in vitro measurable growth inhibition, as set forth in Table 2.

The in vitro antimalarial drug susceptibility assay used to screen the compounds of the present invention is a modification of the procedures first published by Desjardins et al., with modifications developed by Milhous et al. See Desjardins, R. E., et al. (1979) Antimicrob. Agents Chemother. 16:710–718; and Milhous, W. K., et al. (1985) Antimicrob. Agents Chemother. 27:525–530, which are herein incorporated by reference.

In brief, the assay relies on the incorporation of radiolabeled hypoxanthine by the parasites and inhibition of isotope incorporation is attributed to activity of known or candidate antimalarials. For each assay, proven antimalarials, were used as controls. The incubation period was 66 hours and the starting parasitemia was 0.2% with a 1% hematocrit. The media used was an RPMI-1640 culture media with no folate or p-aminobenzoic acid (PABA) and 10% normal heat inactivated human plasma.

For quantitative in vitro drug susceptibility testing, two well-characterized *P. falciparum* malaria clones were used, W2 and D6. See Oduola, A. M. J., et al. (1988) Exp. Parasitol. 67:354–360, which is herein incorporated by reference. W2 is a clone of the Indochina I isolate and is resistant to chloroquine and pyrimethamine, but susceptible to mefloquine. D6 is a clone from the Sierra I/UNC isolates and is susceptible to chloroquine and pyrimethamine, but has reduced susceptibilities to mefloquine and halofantrine.

The compounds of the present invention were dissolved directly in dimethylsulfoxide (DMSO) and diluted 400 fold with complete culture media. The compounds were then diluted 2-fold, 11 times, to give a concentration range of 1,048-fold. These dilutions were performed automatically by a Biomek 1000 or 2000 Liquid Handling System into 96-well microtiter plates. The diluted compounds were then transferred (25 µl) to test plates, 200 µl of parasitized erythrocytes (0.2% parasitemia and 1% hematocrit) were added, and incubated at 37° C. in a controlled environment of 5% $CO_2$, 5% $O_2$ and 90% $N_2$. After 42 hours, 25 µl of 3H-hypoxanthine was added and the plates were incubated for an additional 24 hours. At the end of the 66-hour incubation period, the plates were frozen at −70° C. to lyse the red cells and which were later thawed and harvested onto glass fiber filter mats by using a 96-well cell harvester. The filter mats were then counted in a scintillation counter and the data was recorded. For each compound, the concentration response profile was determined and 50% inhibitory concentrations ($IC_{50}$) were determined by using a nonlinear, logistic dose response analysis program. [WKM: What program? Please provide vendor name, city and state.]

Table 2 shows that the mixed tetraoxanes of the present invention are more potent against W2 than against D6 clone, with exception of the inactive mixture 8e, and 4"-ethyl substituted compounds: 9i, 9j, 25, 26, 32, 1B12a, 1B12b, 8i (1B13a), 8j (1B13b), 20 (1C29), 9i (1C34), 1C45, 1C47, 1C48, and 1C53.

E. ANTIBACTERIAL ASSAY

EXAMPLE 57

The activity of the compounds of the present invention against *Mycobacterium tuberculosis* was determined using the following assays conducted by the National Institute of Allergy and Infectious Diseases (NIAID) supports a TB drug acquisition and screening program, the TAACF.

1. In Vitro Evaluation of Anti-*Mycobacterium tuberculosis* Activity

To determine the percent inhibition the following assay was conducted. Primary screening was conducted at 6.25 µg/ml (or the molar equivalent of highest molecular weight compound in a given series of congeners) against *Mycobacterium tuberculosis* $H_{37}Rv$ (ATCC 27294) in BACTEC 12B medium using the Microplate Alamar Blue Assay (MABA). See Collins, L. and S. G. Franzblau. 1997. Microplate alamar blue assay versus BACTEC 460 system for high-throughput screening of compounds against *Mycobacterium tuberculosis* and *Mycobacterium avium*. Antimicrob Agents Chemother 41:1004–9, which is herein incorporated by reference.

Compounds exhibiting fluorescence are tested in the BACTEC 460-radiometric system. Compounds effecting less than about 90% inhibition in the primary screen (MIC>6.25 µg/ml) were not generally evaluated further. Minimum compound requirements: 1.0 mg.

2. Minimum Inhibitory Concentration (MIC)

Compounds that demonstrated at least about 90% inhibition in the primary screen were re-tested at lower concentrations against *M. tuberculosis* H37Rv to determine the actual minimum inhibitory concentration (MIC) in the MABA. The MIC is defined as the lowest concentration effecting a reduction in fluorescence of 90% relative to controls. Minimum compound requirements: 1.0 mg.

3. Cytotoxicity

Concurrent with the determination of MICs, compounds are tested for cytotoxicity ($IC_{50}$) in VERO cells at concentrations less than or equal to 62.5 µg/ml or 10 times the MIC for *M. tuberculosis* $H_{37}Rv$. After 72 hours exposure, viability was assessed on the basis of cellular conversion of MTT into a formazan product using the Promega CellTiter 96 Non-radioactive Cell Proliferation Assay. Minimum compound requirements: 2.0 mg.

The results of the above experiments are summarized in Table 5 as follows:

TABLE 5

Activity Against *M. tuberculosis*

| Compd | Structural formula | Assay | % Inhib | MIC (μg/mL) | IC$_{50}$ (μg/mL) | Si |
|---|---|---|---|---|---|---|
| 8a/1B04 | | Alamar | 0 | >6.25 | — | — |
| 8c/1B11 | | Alamar | 0 | >6.25 | — | — |
| 8e/1B07 | | Alamar | 0 | >6.25 | — | — |
| 8f/1B10 | | Alamar | 0 | >6.25 | — | — |

TABLE 5-continued

Activity Against *M. tuberculosis*

| Compd | Structural formula | Assay | % Inhib | MIC (μg/mL) | IC$_{50}$ (μg/mL) | Si |
|---|---|---|---|---|---|---|
| 8g 1B09a | | Alamar | 32 | >6.25 | — | — |
| 8l 1B09b | | Alamar | 0 | >6.25 | — | — |
| 8d/1B06 | | Alamar | 29 | >6.25 | — | — |
| 9d/1C16 | | Alamar | 0 | >6.25 | — | — |

TABLE 5-continued

Activity Against *M. tuberculosis*

| Compd | Structural formula | Assay | % Inhib | MIC (μg/mL) | IC$_{50}$ (μg/mL) | Si |
|---|---|---|---|---|---|---|
| 13/1C22 | | Alamar | 100 | 0.2 | | |
| | | *M. avium;* strain 100; Microtiter | — | >32 | MIC dilution: 0.25, 0.5, 1, 2, 4, 8, 16, 32 | |
| | | *M. avium;* strain 101; Microtiter | — | >32 | MIC dilution: 0.25, 0.5, 1, 2, 4, 8, 16, 32 | |
| | | *M. avium;* strain 108; Microtiter | — | >32 | MIC dilution: 0.25, 0.5, 1, 2, 4, 8, 16, 32 | |
| | | *M. avium;* strain 109; Microtiter | — | >32 | MIC dilution: 0.25, 0.5, 1, 2, 4, 8, 16, 32 | |
| | | *M. avium;* strain 116; Microtiter | — | >32 | MIC dilution: 0.25, 0.5, 1, 2, 4, 8, 16, 32 | |
| 14/1C23 | | Alamar | 99 | 3.13 | 5.63 | 1.8 |
| 15/1C24 | | Alamar | 98 | 3.13 | 7.02 | 2.24 |

TABLE 5-continued

Activity Against *M. tuberculosis*

| Compd | Structural formula | Assay | % Inhib | MIC (μg/mL) | IC$_{50}$ (μg/mL) | Si |
|---|---|---|---|---|---|---|
| 16/1C25 | (structure with AcO, CONHPr, OAc, peroxide-cyclohexane) | Alamar | 87 | >6.25 | — | — |
| 8b/1B05 | (structure with AcO, CO$_2$Me, OAc, peroxide-cyclohexane) | Alamar | 0 | >6.25 | — | — |
| 9b/1C15 | (structure with AcO, CO$_2$H, OAc, peroxide-cyclohexane) | Alamar | 33 | >6.25 | — | — |
| 10/1C19 | (structure with AcO, CONH$_2$, OAc, peroxide-cyclohexane) | Alamar | 99 | 6.25 | 4.94 | 0.79 |

TABLE 5-continued

Activity Against *M. tuberculosis*

| Compd | Structural formula | Assay | % Inhib | MIC ($\mu$g/mL) | IC$_{50}$ ($\mu$g/mL) | Si |
|---|---|---|---|---|---|---|
| 11/1C20 | | Alamar | 88 | >6.25 | — | — |
| 12/1C21 | | Alamar | 99 | 6.25 | 5.42 | 0.87 |
| 8g  (4"R) 1B08a | | Alamar | 29 | >6.25 | — | — |
| 9g/1C17 | | Alamar | 21 | >6.25 | — | — |

TABLE 5-continued

Activity Against *M. tuberculosis*

| Compd | Structural formula | Assay | % Inhib | MIC (µg/mL) | IC$_{50}$ (µg/mL) | Si |
|---|---|---|---|---|---|---|
| 17/1C26 | | Alamar | 99 | 3.13 | 3.49 | 1.1 |
| 18/1C27 | | Alamar | 98 | 6.25 | 5.69 | 0.91 |
| 19/1C28 | | Alamar | 98 | 3.13 | 5.37 | 1.7 |
| 20/1C29 | | Alamar | 94 | 6.25 | 8.34 | 1.3 |

TABLE 5-continued

Activity Against *M. tuberculosis*

| Compd | Structural formula | Assay | % Inhib | MIC (µg/mL) | IC$_{50}$ (µg/mL) | Si |
|---|---|---|---|---|---|---|
| 8h 1B08b | (4"S) | Alamar | 38 | >6.25 | — | — |
| 9h/1C18 | | Alamar | 34 | >6.25 | — | — |
| 21/1C30 | | Alamar | 99 | 6.25 | 2.43 | 0.39 |
| 22/1C31 | | Alamar | 99 | 6.25 | 1.83 | 0.29 |

TABLE 5-continued

Activity Against *M. tuberculosis*

| Compd | Structural formula | | Assay | % Inhib | MIC (μg/mL) | IC$_{50}$ (μg/mL) | Si |
|---|---|---|---|---|---|---|---|
| 23/1C32 | | | Alamar | 21 | >6.25 | — | — |
| 24/1C33 | | | Alamar | 0 | >6.25 | — | — |
| 8i 1B13a | (4″R or S) | | Alamar | 62 | >6.25 | — | — |
| 9i/1C34 | | | Alamar | 80 | >6.25 | — | — |

TABLE 5-continued

*Activity Against M. tuberculosis*

| Compd | Structural formula | Assay | % Inhib | MIC (μg/mL) | IC$_{50}$ (μg/mL) | Si |
|---|---|---|---|---|---|---|
| 25/1C35 | | Alamar | 100 | 3.13 | 4.65 | 1.48 |
| 26/1C36 | | Alamar | 99 | 1.56 | 1.83 | 1.17 |
| 27/1C37 | | Alamar | 96 | 1.56 | 1.91 | 1.22 |
| 28/1C38 | | Alamar | 92 | 6.25 | 2.28 | 0.36 |

TABLE 5-continued

Activity Against *M. tuberculosis*

| Compd | Structural formula | Assay | % Inhib | MIC (μg/mL) | IC$_{50}$ (μg/mL) | Si |
|---|---|---|---|---|---|---|
| 8j / 1B13b | (4"S or R) | Alamar | 65 | >6.25 | — | — |
| 9j/1C39 | | Alamar | 95 | 6.25 | 0.95 | 0.15 |
| 29/1C40 | | Alamar | 100 | 3.13 | — | — |
| 30/1C41 | | Alamar | 99 | 3.13 | 1.59 | 0.50 |

TABLE 5-continued

Activity Against *M. tuberculosis*

| Compd | Structural formula | Assay | % Inhib | MIC (µg/mL) | IC$_{50}$ (µg/mL) | SI |
|---|---|---|---|---|---|---|
| 31/1C42 | | Alamar | 83 | >6.25 | — | — |
| 32/1C43 | | Alamar | 71 | >6.25 | — | — |
| 1B14a (4"R or S) | | Alamar | 37 | >6.25 | — | — |
| 1C44 | | Alamar | 94 | 6.25 | 1.07 | 0.17 |

TABLE 5-continued

Activity Against *M. tuberculosis*

| Compd | Structural formula | Assay | % Inhib | MIC (μg/mL) | IC$_{50}$ (μg/mL) | Si |
|---|---|---|---|---|---|---|
| 1C45 | | Alamar | 93 | 6.25 | | |
| 1C46 | | Alamar | 71 | >6.25 | — | — |
| 1C47 | | Alamar | 50 | >6.25 | — | — |
| 1C48 | | Alamar | 46 | >6.25 | — | — |

TABLE 5-continued

Activity Against *M. tuberculosis*

| Compd | Structural formula | | Assay | % Inhib | MIC (μg/mL) | IC$_{50}$ (μg/mL) | Si |
|---|---|---|---|---|---|---|---|
| 1B14b | (4"S or R) | | Alamar | 46 | >6.25 | — | — |
| 1C49 | | | Alamar | 89 | >6.25 | — | — |
| 1C50 | | | Alamar | 87 | >6.25 | — | — |
| 1C51 | | | Alamar | 61 | >6.25 | — | — |

TABLE 5-continued

Activity Against *M. tuberculosis*

| Compd | Structural formula | Assay | % Inhib | MIC ($\mu$g/mL) | IC$_{50}$ ($\mu$g/mL) | SI |
|---|---|---|---|---|---|---|
| 1C52 | [structure with AcO, CONHEt, OAc, Ph] | Alamar | 62 | >6.25 | — | — |
| 1C53 | [structure with AcO, CONHPr, OAc, Ph] | Alamar | 59 | >6.25 | — | — |

MIC of RMP = 0.125 $\mu$g/mL.
MIC of INH = 0.05 $\mu$g/mL.
IC$_{50}$ = INH > 1000;
RMP = 110.67;
DMSO at 1:50 > 1000

As shown in Table 5, compounds were considered active if inhibition was greater than about 50%. Compounds that were selected for the MIC Assay were those that exhibited about 90% or more inhibition. MIC Assay Data. As shown in Table 5, the column labeled MIC lists the measured minimum inhibitory concentration. The significance of this value depends on several factors such as compound structure, novelty, toxicity, and potential mechanism of action. MIC values for control drugs: INH (0.025 to 0.05 $\mu$g/mL) & RMP (0.015 to 0.125 $\mu$g/mL). Some compounds were screened by serial dilution to assess toxicity to a VERO cell line, generally beginning at 10× the MIC if sample solubility in culture media permited. The column labled SI indicates the selectivity index is defined as the ratio of the measured IC$_{50}$ in VERO cells to the MIC described above. IC$_{50}$ & SI values for control drugs: INH (IC$_{50}$>1000 $\mu$g/mL/SI>40,000) & RMP (IC$_{50}$>100 $\mu$g/mL/SI>800).

4. In Vivo Evaluation of Anti-*Mycobacterium tuberculosis* Activity

The in vivo activity of the compounds of the present invention may be determined using conventional methods known in the art. For example, activity against *Mycobacterium avium* (ATCC 25291) and the maxium tolerated dose (MTD) may be determined as follows:

C57BL/6 female mice (6–8 weeks in age) are administered a one-time dose (oral gavage) of the compound at concentrations of 100, 300 or 1000 mg/Kg. The compounds are dissolved in an appropriate vehicle (ETOH, DMSO or methylcellulose), administered in a solution if necessary. There are 3 animals per dose and they are observed post-administration for 4 hours again 6 hours later then twice daily for the duration of the study (1 week). If an animal exhibits obvious signs of distress (hunched posture, ruffled fur etc.), it is euthanized. The surviving mice are sacrificed day 7 post-administration and the critical organs are observed for evidence of drug toxicity. If abnormalities exist or there were other animals in the same group which did not survive to day 7, the tissues from the liver, heart, and kidneys are extracted and placed into 10% formalin solution. These fixed tissues are sectioned and examined for abnormalities resulting from drug toxicity. The MTD (mg/Kg) is the highest dose that results in no lethality/tissue abnormality.

E. ANTIPROLIFERATIVE SCREENING ASSAY

EXAMPLE 58

DTP Human Tumor Cell Line Screen

The activity of numerous compounds of the present invention against various cancer cell lines was submitted to the Developmental Therapeutics Program (DTP) at the National Cancer Institute (NCI) of the National Institutes of Health (NIH) for screening.

The DTP Human Tumor Cell Line Screen utilizes 60 different human tumor cell lines, representing leukemia, melanoma and cancers of the lung, colon, brain, ovary, breast, prostate, and kidney according to conventional methods known in the art. See e.g. Alley, M. C., et al. (1988) Cancer Research 48:589–601; Grever, M. R., et al. (1992) Seminars in Oncology 19(6):622–638; and Boyd, M. R., and Paull, K. D. (1995) Drug Development Research 34:91–109, which are herein incorporated by reference.

Generally, the human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µl at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 hours prior to addition of the compounds to be tested.

After 24 hours, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Additional four, 10-fold or ½ log serial dilutions are made to provide a total of five drug concentrations plus control. Aliquots of 100 µl of these different drug dilutions are added to the appropriate microtiter wells already containing 100 µl of medium, resulting in the required final drug concentrations.

Following drug addition, the plates are incubated for an additional 48 hours at 37° C., 5% $CO_2$, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the(plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements (time zero, (Tz), control growth, (C), and test growth in the presence of drug at the five concentration levels (Ti)), the percentage growth is calculated at each of the drug concentrations levels. Percentage growth inhibition is calculated as:

$((Ti-Tz)/(C-Tz)) \times 100$ for concentrations for which $Ti >/= Tz$ $((Ti-Tz)/Tz) \times 100$ for concentrations for which $Ti < Tz$.

Three dose response parameters are calculated for each experimental agent.

Growth inhibition of 50% ($GI_{50}$) is calculated from $((Ti-Tz)/(C-Tz)) \times 100 = 50$, which is the drug concentration resulting in a 50% reduction in the net protein increase (as measured by SRB staining) in control cells during the drug incubation. The drug concentration resulting in-total growth inhibition (TGI) is calculated from $Ti=Tz$. The $LC_{50}$ (concentration of drug resulting in a 50% reduction in the measured protein at the end of the drug treatment as compared to that at the beginning) indicating a net loss of cells following treatment is calculated from $((Ti-Tz)/Tz) \times 100 = -50$. Values are calculated for each of these three parameters if the level of activity is reached; however, if the effect is not reached or is exceeded, the value for that parameter is expressed as greater or less than the maximum or minimum concentration tested.

Figure 1B:
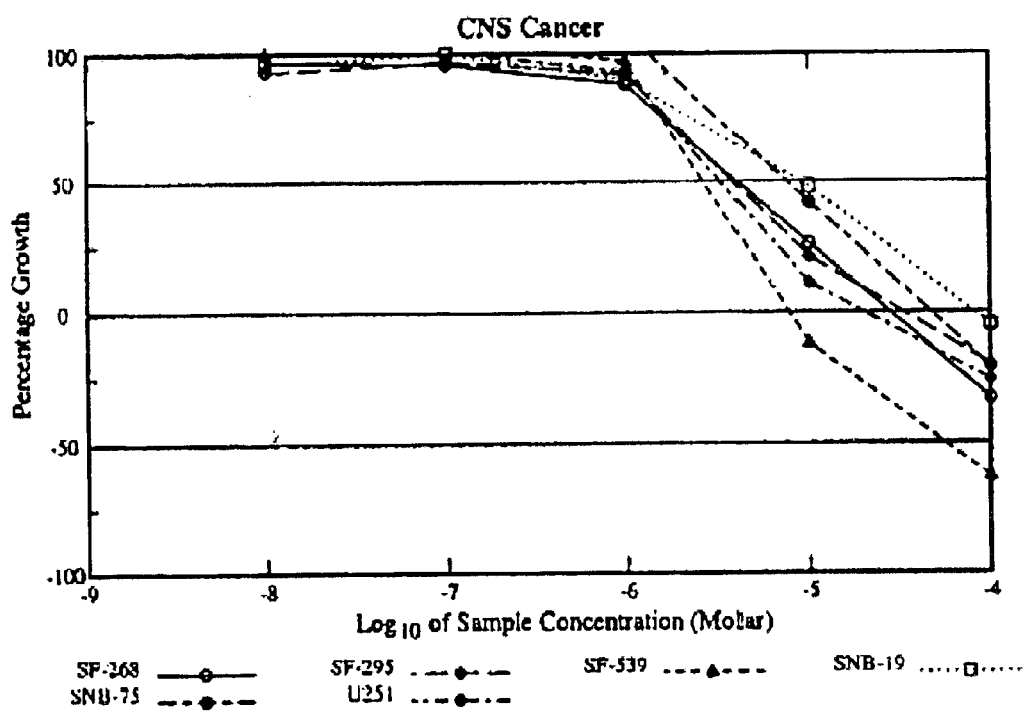
FIG. 1B shows the CNS cancer cell lines.
Figure 1C:
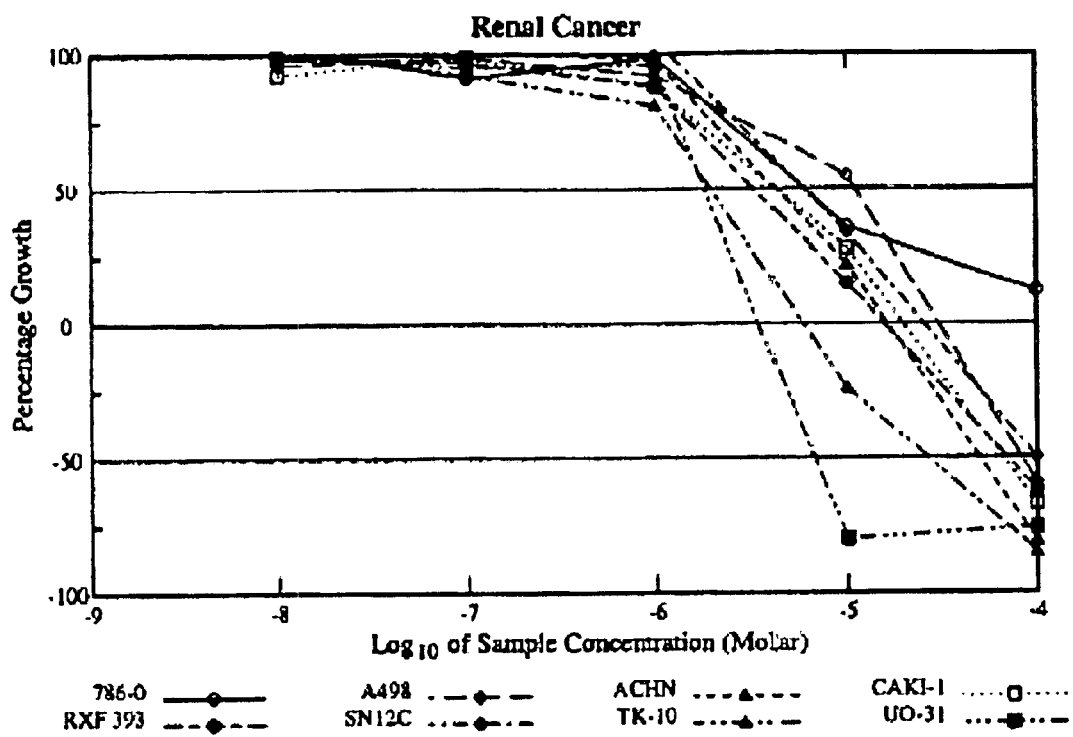
FIG. 1C shows the renal cancer cell lines.
Figure 1D:
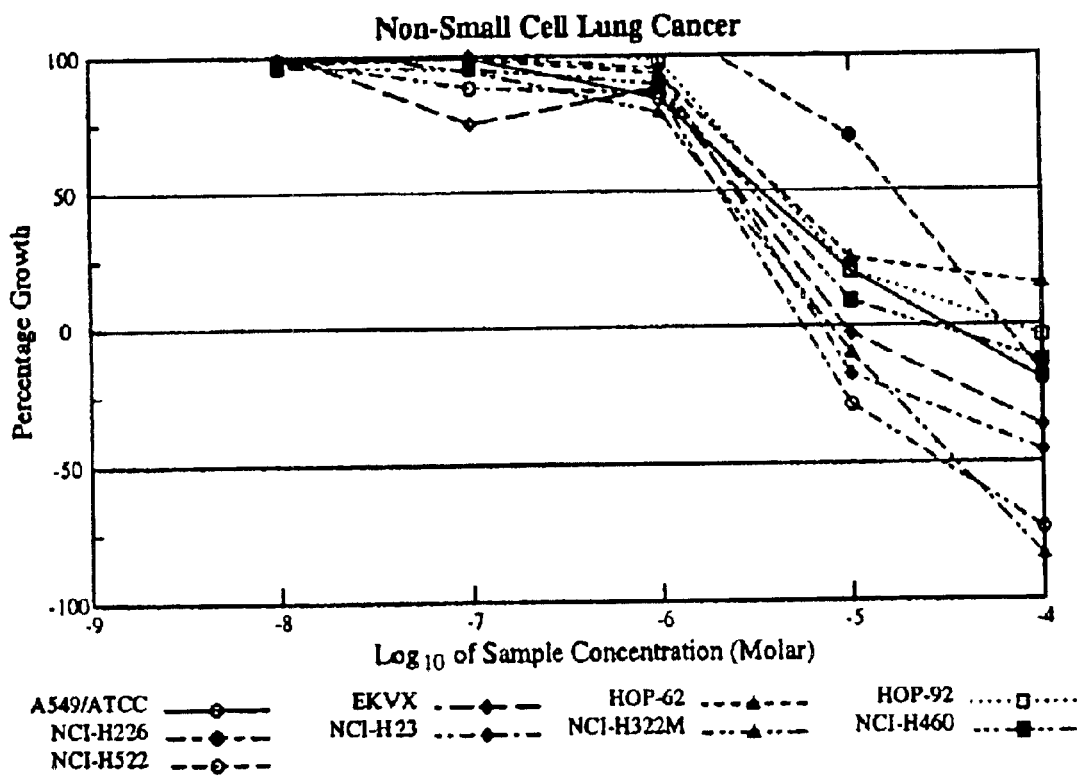
FIG. 1D shows the non-small cell lung cancer cell lines.
Figure 1E:
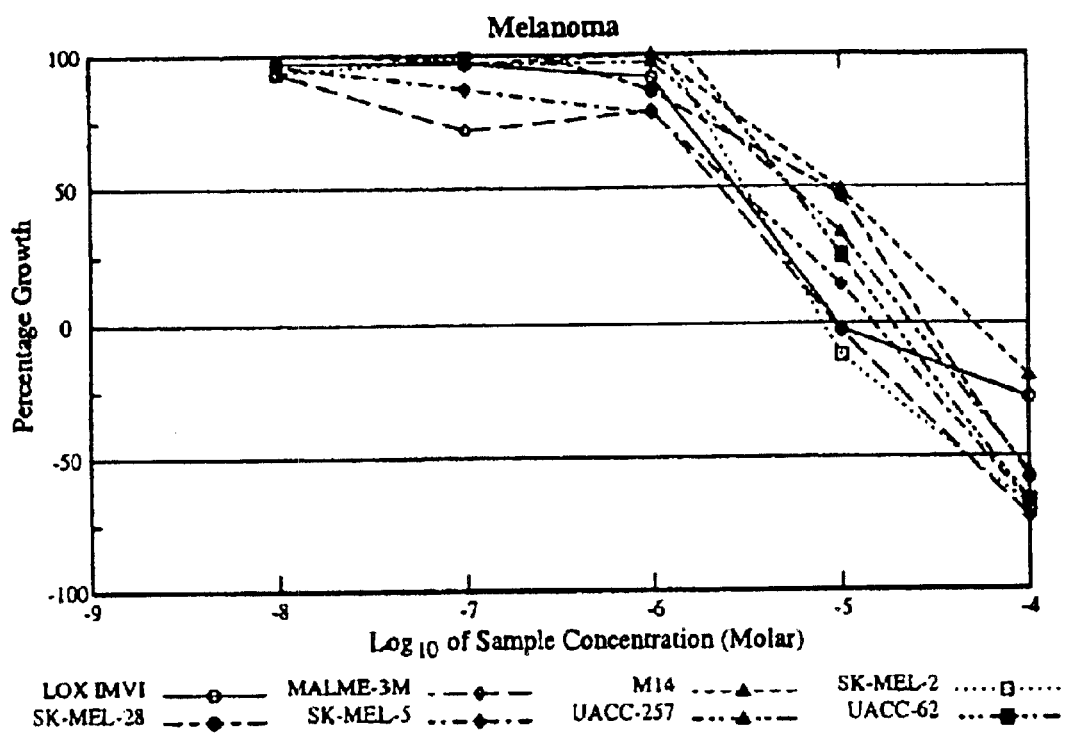
FIG. 1E shows the melanoma cell lines.
Figure 1F:
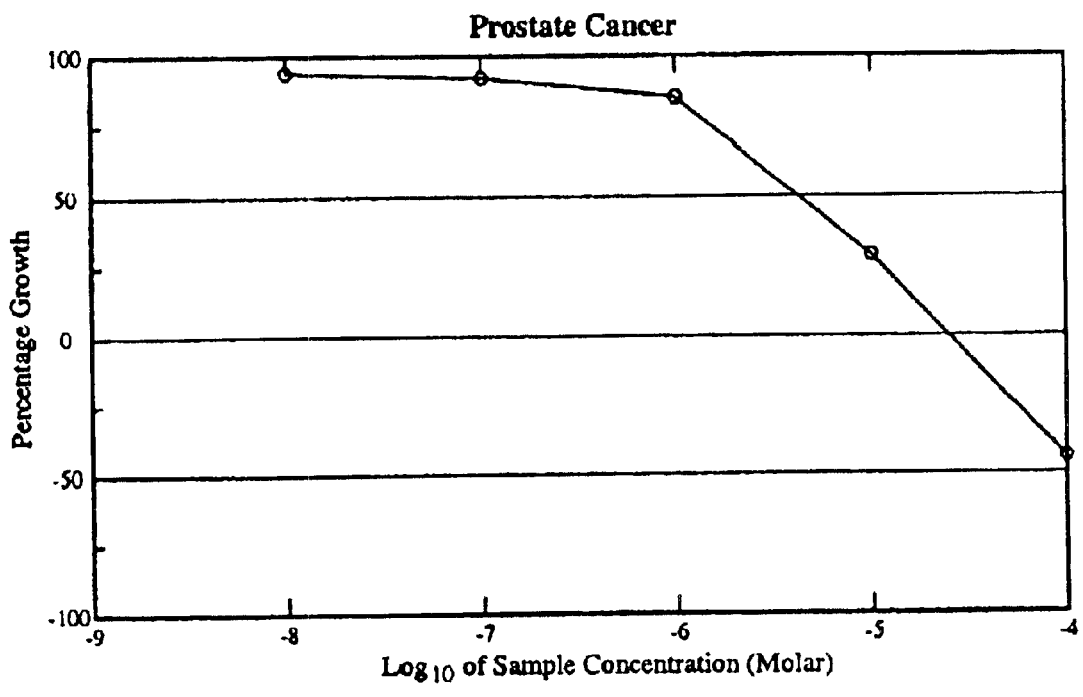
FIG. 1F shows the prostate cancer cell lines.
Figure 1G:
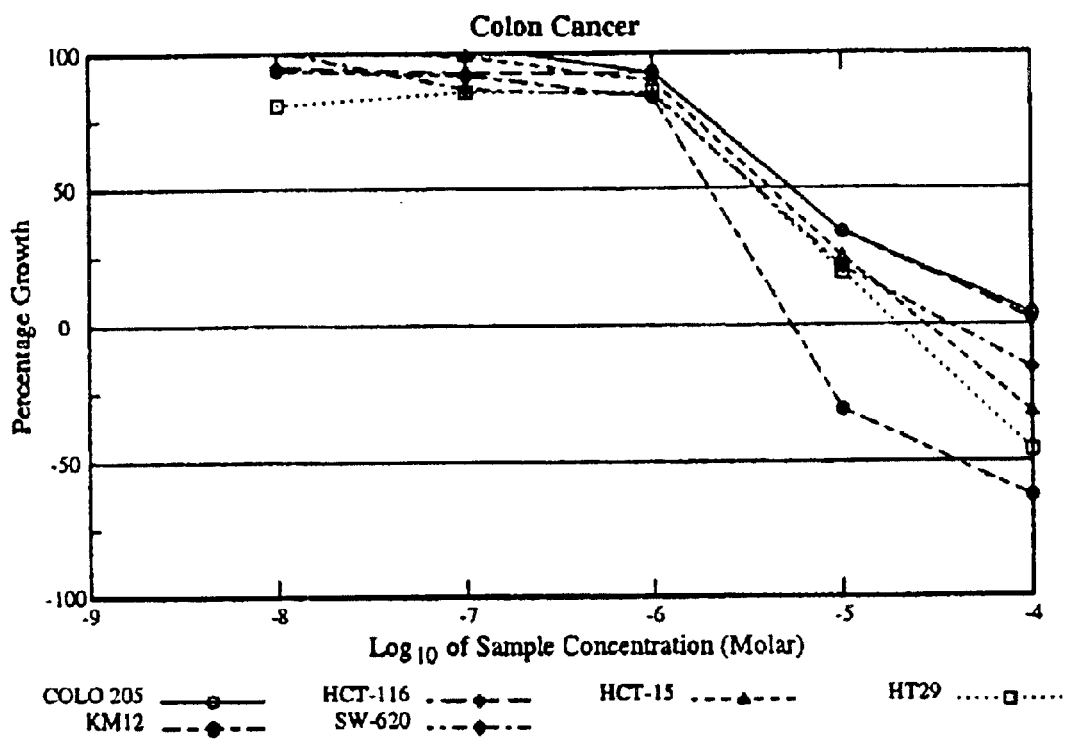
FIG. 1G shows the colon cancer cell lines.
Figure 1H:
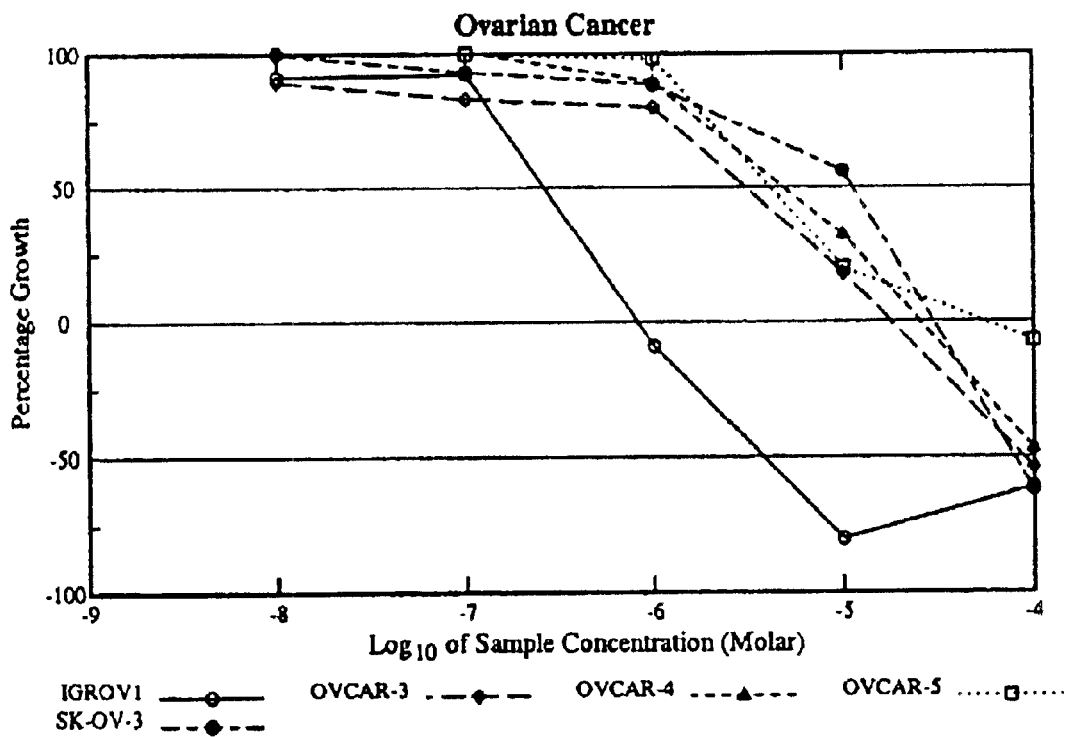
FIG. 1H shows the ovarian cancer cell lines.
Figure 1I:
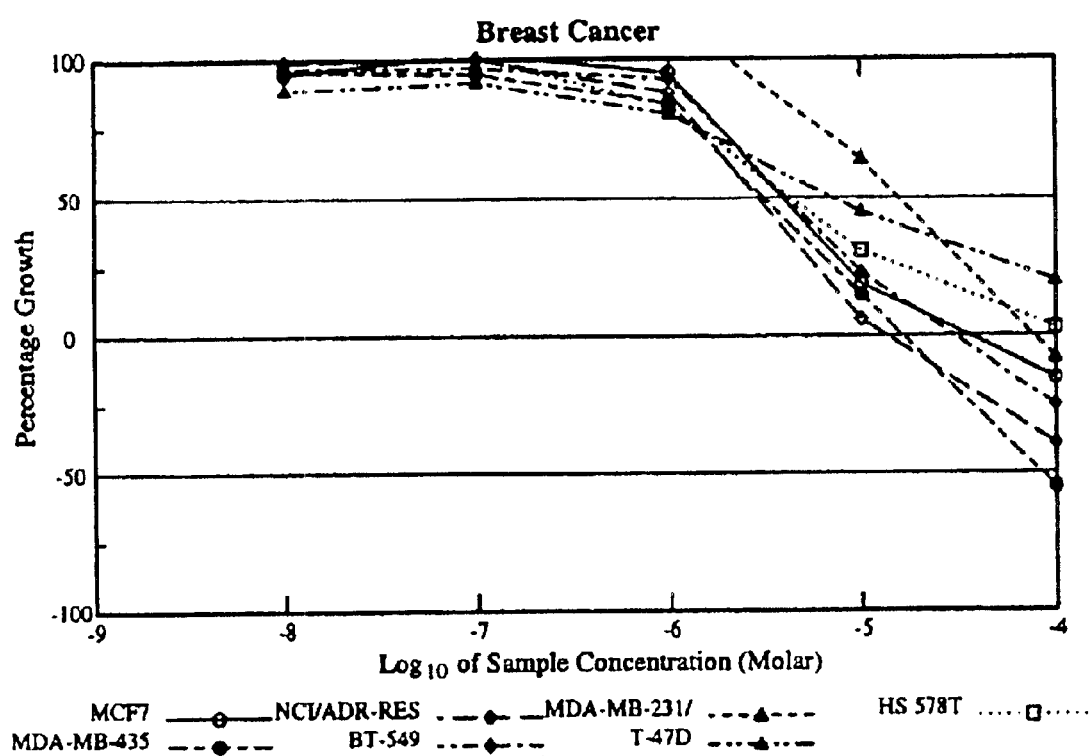
FIG. 1I shows the breast cancer. cell lines.

FIG. 1 is an example of the dose response curves obtained for the various cancer cell lines screened for compound 1C44. FIG. 2 provides an example table listing the various cell lines tested for compound 1C44 and the $GI_{50}$, TGI, and $LC_{50}$ for each. It is noted that each of the compounds listed in Table 6 were screened for activity against each cancer cell line provided in FIG. 2. The results of the assay are summarized in Table 6 as follows:

TABLE 6

In vitro Antiproliferative Activity* of Mixed Steroidal Tetraoxanes
(60 cell lines, range; after 48 h; Conc. Units: Molar)

| Compound | $GI_{50}$ | TGI | $LC_{50}$ |
|---|---|---|---|
| 8a/1B04 | >1.00E−04–2.47E−06 | >1.00E−04–9.44E−06 | >1.00E−04–7.68E−05 |
| 8b/1B05 | >1.00E−04–1.02E−06 | >1.00E−04–6.34E−06 | >1.00E−04–3.68E−05 |
| 8g/1B08a | >1.00E−04–<1.00E−08 | >1.00E−04–1.29E−06 | >1.00E−04–4.07E−05 |
| 8h/1B08b | >1.00E−04–3.15E−06 | >1.00E−04–1.72E−05 | >1.00E−04–7.39E−05 |
| 8k/1B09a | >1.00E−04–3.91E−06 | >1.00E−04–2.90E−05 | >1.00E−04–6.80E−05 |
| 8c/1B11 | >1.00E−04–1.37E−06 | >1.00E−04–6.21E−06 | >1.00E−04 |
| 9b/1C15 | 1.64E−05–1.86E−06 | 5.16E−05–3.90E−06 | >1.00E−04–8.17E−06 |
| 9g/1C17 | 2.21E−05–1.63E−06 | >1.00E−04–3.82E−06 | >1.00E−04–8.92E−06 |
| 9h/1C18 | 1.30E−05–1.40E−06 | 3.81E−05–2.76E−06 | >1.00E−04–5.43E−06 |
| 10/1C19 | 1.24E−05–<1.00E−08 | 2.29E−05–1.39E−08 | >1.00E−04–3.97E−08 |
| 11/1C20 | >1.00E−04–<1.00E−08 | >1.00E−04–<1.00E−08 | >1.00E−04–1.67E−08 |
| 12/1C21 | 2.37E−05–5.80E−07 | 5.42E−05–1.73E−06 | >1.00E−04–4.38E−06 |
| 17/1C26 | 1.43E−05–1.01E−06 | 2.93E−05–2.35E−06 | >1.00E−04–5.49E−06 |
| 19/1C28 | >1.00E−04–5.74E−07 | >1.00E−04–2.38E−06 | >1.00E−04–5.59E−06 |
| 21/1C30 | 1.17E−05–4.91E−07 | 2.44E−05–1.84E−06 | >1.00E−04–4.95E−06 |
| 23/1C32 | 2.56E−05–6.89E−07 | >1.00E−04–2.09E−06 | >1.00E−04–5.08E−06 |
| 24/1C33 | 8.98E−05–3.76E−08 | >1.00E−04–1.98E−06 | >1.00E04–5.98E−06 |
| 9i/1C34 | 2.02E−05–6.70E−07 | >1.00E−04–3.80E−06 | >1.00E−04–8.01E−06 |
| 25/1C35 | 1.62E−05–1.08E−06 | >1.00E−04–3.09E−06 | >1.00E−04–6.28E−06 |
| 1C44 | 1.69E−05–2.60E−07 | >1.00E−04–8.18E−07 | >1.00E−04–3.76E−06 |
| 1C45 | 1.82E−05–2.03E−08 | >1.00E−04–1.11E−06 | >1.00E−04–4.57E−06 |

*activities are presented as ranges over all cell lines tested per compound.

EXAMPLE 59

Hollow Fiber Assay

Generally, as a preliminary in vivo screening tool, the following assay is conducted. A standard panel of 12 tumor cell lines were used for the routine hollow fiber screening of the in vitro activities. These include NCI-H23, NCI-H522, MDA-MB-231, MDA-MB-435, SW-620, COLO 205, LOX, UACC-62, OVCAR-3, OVCAR-5, U251 and SF-295 according to conventional methods known in the art. See e.g. Hollingshead, M., et al. (1995) Life Sciences 57:131–141, which is herein incorporated by reference. The cell lines are cultivated in RPMI-1640 containing 10% FBS and 2 mM glutamine. On the day preceeding hollow fiber preparation, the cells are given a supplementation of fresh medium to maintain log phase growth. For fiber preparation, the cells are harvested by standard trypsinization technique and resuspended at the desired cell density (($2$–$10\times10^6$ cells/ml). The cell suspension is flushed into 1 mm (internal diameter) polyvinylidene fluoride hollow fibers with a molecular weight exclusion of 500,000 Da. The hollow fibers are heat-sealed at 2 cm intervals and the samples generated from these seals are placed into tissue culture medium and incubated at 37° C. in 5% $CO_2$ for 24 to 48 hours prior to implantation. A total of 3 different tumor lines are prepared for each experiment so that each mouse receives 3 intraperitoneal implants (1 of each tumor line) and 3 subcutaneous implants (1 of each tumor line). On the day of implantation, samples of each tumor cell line preparation are quantitated for viable cell mass by a stable endpoint MTT assay so that the time zero cell mass is known. Mice are treated with experimental agents starting on day 3 or 4 following fiber implantation and continuing daily for 4 days. Each agent is administered by intraperitoneal injection at 2 dose levels. The fibers are collected from the mice on the day following the fourth compound treatment and subjected to the stable endpoint MTT assay. The optical density of each sample is determined spectrophotometrically at 540 nm and the mean of each treatment group is calculated. The percent net growth for each cell line in each treatment group is calculated and compared to the percent net growth in the vehicle treated controls.

A 50% or greater reduction in percent net growth in the treated samples compared to the vehicle control samples is considered a positive result. Each positive result is given a score of 2 and all of the scores are totaled for a given compound. The maximum possible score for an agent is 96 (12 cell lines×2 sites×2 dose levels×2 (score)). A compound is referred for xenograft testing if it has a combined IP+SC score of 20 or greater, a SC score of 8 or greater, or produces cell kill of any cell line at either dose level evaluated.

Compound 1C20 was tested and the results are as follows: IP 18, SC 2, Total Score 20, and Cell Kill N. Thus, compound 1C20 will be evaluated evaluated further by NCI as a potential cancer therapeutic.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A compound of the following structural formula 1

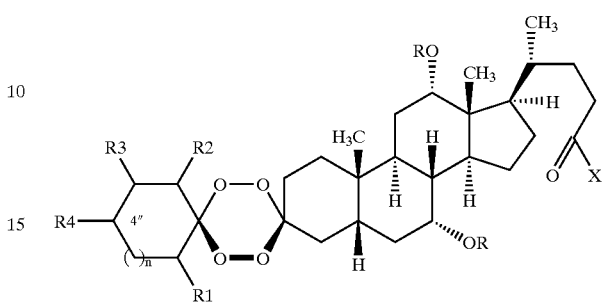

or an epimer at C("4)

wherein n is 0, 1, 2 or 3;

R is H; ethanoyl, propanoyl, or benzoyl;

R1 is H, methyl, ethyl, or isopropyl;

R2 is H, methyl, or ethyl;

R3 is H, methyl, or ethyl;

R4 is H, methyl, ethyl, tert-butyl, phenyl, p-hydroxyphenyl, p-methoxyphyl, or p-nitrophonyl, or

wherein Y is a $C_1$–$C_4$ straight or branched-chain alkoxy, hydroxyl or

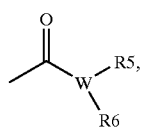

wherein W is N, R5 is hydrogen, methyl, ethyl, n-propyl, isopropyl, or methyl ethanoate 2-yl, and R6 is hydrogen, methyl, ethyl, or n-propyl, or R5 and R6 together with the N to which they are attached form a pyrrolidino or piperidine ring;

X is OH, a $C_1$–$C_4$ straight or branched-chain alkoxy, a primary amino, a N-alkylamino wherein the alkyl is a straight-chain alkyl groups containing from 1 to 4 carbon atoms, methyl ethanoate-2-yl, N-phenylamino, p-nitrophenyl, N,N-dimethylamino, N,N-diethylamino, N,N-di(n-propyl)amino, N-pyrrolidino, or N-piperidino.

2. The compound of claim 1 wherein n is 0.
3. The compound of claim 1 wherein n is 1.
4. The compound of claim 1 wherein n is 2.
5. The compound of claim 1 wherein n is 3.
6. The compound of claim 1 wherein R is ethanoyl.
7. The compound of claim 1 wherein R1 is H, R2 is H, and R3 is H.
8. The compound of claim 1 wherein R4 is attached to ring carbon of (R)-configuration.
9. The compound of claim 1 wherein R4 is attached to ring carbon of (S)-configuration.

10. The compound of claim 1 wherein R4 is H, methyl, ethyl, phenyl, tert-butyl, n-propyl, or ethoxycarbonyl.

11. The compound of claim 1 wherein X is hydroxyl, methoxy, primary amino, N-methylamino, N-ethylamino, N-(n-propyl)amino, or N-(methyl ethanoate-2-yl)amino.

12. A composition comprising two or more compounds of claim 1.

13. The composition of claim 12, and further comprising at least one epimer of one of the compounds in the composition.

14. The composition of claim 12 wherein n is 0 for at least one of the compounds.

15. The composition of claim 12 wherein n is 1 for at least one of the compounds.

16. The composition of claim 12 wherein n is 2 for at least one of the compounds.

17. The composition of claim 12 wherein n is 3 for at least one of the compounds.

18. The composition of claim 12 wherein R is ethanoyl for at least one of the compounds.

19. The composition of claim 12 wherein R1 is H, R2 is H, and R3 is H for at least one of the compounds.

20. The composition of of claim 12 wherein R4 is attached to the ring carbon of (R)-configuration for at least one of the compounds.

21. The composition of claim 12 wherein R4 is attached to the ring carbon of (S)-configuration for at least one of the compounds.

22. The composition of claim 12 wherein R4 is, methyl, ethyl, phenyl, tert-butyl, n-propyl, or ethoxycarbonyl for at least one of the compounds.

23. The composition of claim 12 wherein X is hydroxyl, methoxy, primary amino, N-methylamino, N-ethylamino, N-(n-propyl)amino, or N-(methyl ethanoate-2-yl)amino for at least one of the compounds.

24. A pharmaceutical composition comprising at least one compound of claim 1 and a pharmaceutically acceptable carrier.

25. A pharmaceutical composition comprising the composition of claim 12 and a pharmaceutically acceptable carrier.

26. A method of treating a *Plasmodium* parasite mycobacteria infection or cancer selected from the group consisting of ovarian cancer, renal cancer, leukemia, colon cancer, melanoma, non-small lung cancer, CNS cancer, prostate cancer, and breast cancer in a subject which comprises administering to the subject a therapeutically effect amount of at least one compound of claim 1.

27. A method of treating a *Plasmodium* parasite or mycobacteria infection or cancer selected from the group consisting of ovarian cancer, renal cancer, leukemia, colon cancer, melanoma, non-small lung cancer, CNS cancer, prostate cancer, and breast cancer in a subject which comprises administering to the subject a therapeutically effect amount of the mixture of claim 12.

28. The method of claim 26, wherein the infection is caused by *Mycobacterium tuberculosis*.

29. The method of claim 26, wherein the infection is caused by *P. falciparum, P. vivax, P. ovale*, or *P. malariae*.

30. The method of claim 27, wherein the infection is caused by *Mycobacterium tuberculosis*.

31. The method of claim 27, wherein the infection is caused by *P. falciparum. P. vivax, P. ovale*, or *P. malariae*.

32. The method of claim 26, wherein the compound is an amide.

33. A method of inhibiting the growth of at least one *Plasmodium* parasite in vivo or in vitro which comprises contacting the *Plasmodium* parasite with at least one compound of claim 1.

34. The method of claim 33, wherein the *Plasmodium* parasite is *P. falciparum, P. vivax, P. ovale*, or *P. malariae*.

35. The method of claim 34, wherein the *Plasmodium* parasite is resistant to an antimalarial drug.

36. A method for making the compound of claim 1 which comprises reacting a compound having the following structural formula 2

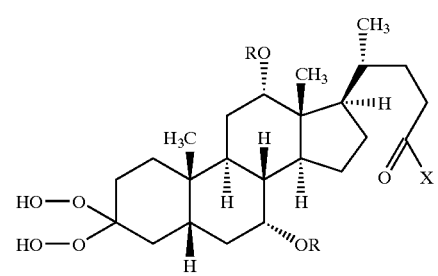

wherein

R is H, ethanoyl, propanoyl, or benzoyl;

X is a $C_1$–$C_4$ straight or branched-chain alkoxy, primary amino, N-alkylamino wherein the alkyl is a straight-chain alkyl group containing from 1 to 4 carbon atoms, methyl ethanoate-2-yl, N-phenylamino, p-nitropbenyl, N,N-dimethylamino, N,N-diethylamino, N,N-di(n-propyl)amino, N-pyrrolidino, or N-piperidino with a compound having the structural formula 3

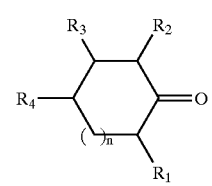

wherein n is 0, 1, 2, or 3;

R1 is H;

R2 is H;

R3 is H;

R4 is a straight or branched-chain alkyl containing from 1 to 3 carbon atoms, phenyl which may be substituted by one or more substituents selected from the group consisting of halogen, hydroxyl, $C_1$–$C_2$ alkoxy, $C_1$–$C_2$ alkyl, nitro or $CF_3$; or

wherein Y is a $C_1$–$C_4$ straight or branched-chain alkoxy, or

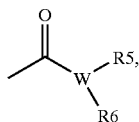

wherein W is N, R5 is hydrogen, a $C_1$–$C_4$ straight or branched-chain alkyl, a $C_1$–$C_4$ straight or branched-chain alkyl ethanoate 2-yl, ethanoic acid 2-yl, phenyl which may be substituted by one or more substituents selected from the group consisting of halogen, $C_1$–$C_2$ alkoxy, $C_1$–$C_2$ alkyl or $CF_3$; and R6 is hydrogen, a $C_1$–$C_4$ straight or branched-chained alkyl, or R5 and R6 together with the N to which they are attached form a pyrrolidine or piperidine ring, in a solvent.

37. The method of claim 36, wherein the solvent is toluene, benzene, ether, THF, $CH_3CN$, $CH_2Cl_2$, or mixtures thereof.

38. The method of claim 36, wherein the solvent is $CH_2Cl_2$.

39. The method of claim 36, wherein the reaction is conducted at a temperature range of about –35° C. to about 10° C. for about 3 to about 240 minutes.

40. The method of claim 36, wherein the reaction is conducted at a temperature of about 0° C. for about 15 minutes.

41. The method claim 36, wherein a catalyst is used.

42. The method claim 41, wherein the catalyst is sulfuric acid dissolved in $CH_3CN$.

43. A method for making the compound of claim 1 which comprises reacting compound having the following structural formula 4

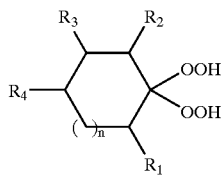

wherein n is 0, 1, 2, or 3;

R1 is H;

R2 is H;

R3 is H;

R4 is H, a straight or branched-chain alkyl group containing from 1 to 3 carbon atoms, phenyl which may be substituted by one or more substituents selected from the group consisting of halogen, hydroxyl, $C_1$–$C_2$ alkoxy, $C_1$–$C_2$ alkyl, nitro or $CF_3$; or

wherein Y is a $C_1$–$C_4$ straight or branched-chain alkoxy, or

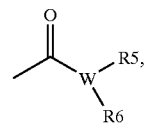

wherein W is N, R5 is hydrogen, a $C_1$–$C_4$ straight or branched-chain alkyl, a $C_1$–$C_4$ straight or branched-chain alkyl ethanoate 2-yl, ethanoic acid 2-yl, or phenyl which may be substituted by one or more substituents selected from the group consisting of halogen, $C_1$–$C_2$ alkoxy, $C_1$–$C_2$ alkyl or $CF_3$; and R6 is hydrogen, a $C_1$–$C_4$ straight or branched-chain alkyl, or R5 and R6 together with the N to which they are attached form a pyrrolidine or piperidine ring with a compound of the structural formula 5

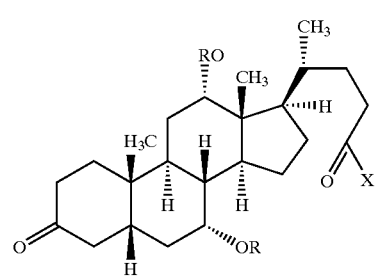

wherein R are each independently H, ethanoyl, propanoyl, or benzoyl;

X is a $C_1$–$C_4$ straight or branched-chain alkoxy, primary amino, N-alkylamino wherein the alkyl is a straight-chain alkyl group containing from 1 to 4 carbon atoms, methyl ethanoate-2-yl, N-phenyl amino, p-nitrophenyl, N,N-dimethylamino, N,N-diethylamino, N,N-di(n-propyl)amino, N-pyrrolidino, or N-piperidino, in a solvent.

44. The method of claim 43, wherein the solvent is toluene, benzene, ether, THF, $CH_3CN$, $CH_2Cl_2$, or mixtures thereof.

45. The method of claim 43, wherein the solvent is $CH_2Cl_2$.

46. The method of claim 43, wherein the reaction is conducted at a temperature range of about –35° C. to about 10° C. for about 3 to about 240 minutes.

47. The method of claim 43, wherein the reaction is conducted at a temperature about 0° C. for about 15 minutes.

48. The method of claim 43, wherein a catalyst is used.

49. The method of claim 48, wherein the catalyst is sulfuric acid dissolved in $CH_3CN$.

50. A method for making the compound of claim 1, wherein X and Y are OH, which comprises reacting the compound of claim 1, wherein X and Y are a $C_1$–$C_4$ alkoxy, with LiOH, NaOH, or KOH in a solvent mixture of $CH_2Cl_2$-MeOH, or $CH_2Cl_2$-EtOH at about 20 to about 25° C., or in a solvent mixture of t-PrOH—$H_2O$ (1-9:9-1, v/v) at about 79° C. for about 10 to about 60 minutes, cooling to room temperature, diluting with water and a non-reacting organic solvent, and water layer acidifying to pH 2 with diluted HCl.

51. The method of claim 50, wherein the non-reacting organic solvent is $CH_2Cl_2$.

52. A method for making the compound of claim 1 which comprises reacting the acid of the compound of claim 1, which acid comprises OH for X and Y, with organic base and $ClCO_2Et$ and then adding ammonia, primary amine, secondary amine, or an ammonium salt thereof together with a tertiary amine.

53. The method of claim 52, wherein the organic base is $Et_3N$, in $CH_2Cl_2$.

54. The method of claim 26, wherein the infection is caused by *P. falciparum*.

55. The method of claim 27, wherein the infection is caused by *P. falciparum*.

56. A method of inhibiting the growth of *Plasmodium falciparum* in vivo or in vitro which comprises contacting the *Plasmodium falciparum* with at least one compound of claim 1.

57. The method of claim 56, wherein the *Plasmodium falciparum* is resistant to an antimalarial drug.

* * * * *